United States Patent
Gu et al.

(10) Patent No.: US 7,504,220 B2
(45) Date of Patent: Mar. 17, 2009

(54) METHOD OF REVERSE TRANSCRIPTION

(75) Inventors: Trent Gu, Madison, WI (US); Fen Huang, Madison, WI (US); James Robert Hartnett, Madison, WI (US)

(73) Assignee: Promega Corporation, Madison, WI (US)

( * ) Notice: Subject to any disclaimer, the term of this patent is extended or adjusted under 35 U.S.C. 154(b) by 204 days.

(21) Appl. No.: 11/475,663

(22) Filed: Jun. 27, 2006

(65) Prior Publication Data

US 2006/0240468 A1 Oct. 26, 2006

Related U.S. Application Data

(63) Continuation of application No. 10/178,673, filed on Jun. 24, 2002, now Pat. No. 7,094,539, which is a continuation of application No. 09/517,871, filed on Mar. 2, 2000, now Pat. No. 6,436,677.

(51) Int. Cl.
 *C12Q 1/68* (2006.01)
(52) U.S. Cl. .......................... 435/6; 435/91.1; 435/91.2
(58) Field of Classification Search .................. None
 See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,707,235 A | 11/1987 | Englert et al. | |
| 4,889,818 A | 12/1989 | Gelfand et al. | |
| 4,965,188 A | 10/1990 | Mullis et al. | |
| 5,075,216 A | 12/1991 | Innis et al. | |
| 5,079,352 A | 1/1992 | Gelfand et al. | |
| 5,096,815 A | 3/1992 | Ladner et al. | |
| 5,198,346 A | 3/1993 | Ladner et al. | |
| 5,210,036 A | 5/1993 | Comb et al. | |
| 5,223,409 A | 6/1993 | Ladner et al. | |
| 5,322,770 A * | 6/1994 | Gelfand ........................ 435/6 | |
| 5,322,785 A | 6/1994 | Comb et al. | |
| 5,324,637 A | 6/1994 | Thompson et al. | |
| 5,352,600 A | 10/1994 | Gelfand et al. | |
| 5,436,149 A | 7/1995 | Barnes | |
| 5,747,298 A | 5/1998 | Hong et al. | |
| 5,830,714 A | 11/1998 | Swaminathan et al. | |
| 5,834,253 A | 11/1998 | Hong et al. | |
| 5,866,395 A | 2/1999 | Mathur | |
| 5,874,282 A | 2/1999 | Riggs et al. | |
| 5,912,155 A | 6/1999 | Chatterjee et al. | |
| 5,939,301 A | 8/1999 | Hughes, Jr. et al. | |
| 5,948,663 A | 9/1999 | Mathur | |
| 5,968,799 A | 10/1999 | Gelfand et al. | |
| 6,001,645 A | 12/1999 | Slater et al. | |
| 6,008,025 A | 12/1999 | Komatsubara et al. | |

| | | |
|---|---|---|
| 6,013,451 A | 1/2000 | Wong et al. |

FOREIGN PATENT DOCUMENTS

| | | |
|---|---|---|
| EP | 258017 | 3/1988 |
| EP | 0 870 832 A1 | 10/1998 |
| JP | 9 140376 | 6/1997 |
| WO | WO8906691 | 7/1989 |
| WO | WO9109944 | 7/1991 |
| WO | WO9109950 | 7/1991 |
| WO | WO9202909 | 2/1992 |
| WO | WO9203556 | 3/1992 |
| WO | WO9206188 | 4/1992 |
| WO | WO9206200 | 4/1992 |
| WO | WO9209689 | 6/1992 |
| WO | WO9209690 | 6/1992 |
| WO | WO9416107 | 7/1994 |
| WO | WO9426766 | 11/1994 |
| WO | WO9527067 | 10/1995 |
| WO | WO9814588 | 4/1998 |
| WO | WO9967037 | 12/1999 |

OTHER PUBLICATIONS

J.G. Black, Microbiology Principles and Applications 2d edition Prentice Hall New Jersey. (1993) p. 145-146.
T.D. Brock, "Introduction: An overview of the thermophiles," in T.D. Brock (ed.), Thermophiles: General, Molecular and Applied Microbiology. John Wiley & Sons New York (1986). pp. 1-16.
T.K. Ng and William R. Kenealy, "Industrial Applications of Thermostable Enzymes," in T.D. Brock (ed.), Thermophiles: General, Molecular, and Applied Microbiology. John Wiley & Sons New York (1986) pp. 197-215.
Bessman et al. 1. Biol. Chem.(1957) 223:171.
Buttin and Kornberg J. Biol. Chem.(1966) 241:5419.
Joyce and Steitz, Trends Biochem. Sci. (1987)12:288-292.
Stenesh and McGowan, Biochim. Biophys. Acta (1977) 475:32-44.

(Continued)

*Primary Examiner*—Gary Benzion
*Assistant Examiner*—Heather G Calamita
(74) *Attorney, Agent, or Firm*—Casimir Jones, S.C.

(57) ABSTRACT

The present invention relates to reverse transcription of RNA, and in particular to reverse transcription by thermostable DNA polymerases. *Thermoactinomyces vulgaris* and *Bacillus stearothermophilus* possess reverse transcriptase activity in the presence of magnesium or manganese ions. Methods, compositions, and kits for reverse transcription and RT-PCR are also provided.

6 Claims, 10 Drawing Sheets

OTHER PUBLICATIONS

Stenesh and Roe, Biochim. Biophys. Acta (1972) 272:156-166.
Low et al. J. Biol. Chem. (1976) 251: 1311.
Ott et al. J. Bacterial. (1986) 165:951.
Harwood et al. J. Biol. Chem. (1970) 245:5614.
Hamilton and Grossman, Biochem. (1974) 13: 1885.
Lonez et al. J. Biol. Chem.(1989) 264:4255.
Engler and Bessman, Cold Springs Harbor Symp. (1979) 43:929.
Barr et al. Biotechniques (1986) 4:428.
Kaledin et al. Biochem. 45:494-501 (1980): Biokhimiya 45:644-651 (1980).
Chien et al. J. Bacteriol. (1976) 127:1550.
A Chien, University of Cincinnati Master's thesis—"Purification and Characterization of DNA Polymerase from *Thermus aquaticus*" (1976).
D. B. Edgar, University of Cincinnati Master's thesis "DNA Polymerase From an Extreme Thermophile: *Thermus aquaticus*" (1974).
Simpson et al. Biochem. Cell Biol.(1990) 68: 1292-1296.
Myers and Gelfand, Biochem. (1991) 30:7661.
Bechtereva et al. Nucleic Acids Res. (1989) 17: I0507.
Glukhov et al. Mol. Cell. Probes (1990) 4:435-443.
Carbakkeira et al. BioTech. (1990) 9:276-281.
Ruttiman et al. Eur. J. Biochem. (1985) 149:41-46.
Oshima et al. J. Biochem. (1974) 75:179-183.
Sakaguchi and Yajima Fed. Proc. (1974) 33:1492 (abstract).
Kaledin et at. Biochem. 46:1247-1254 (1981): Biokhimiya (1981) 46:1576-1584.
Mizusawa et al. Nucl. Acids Res. (1986) 14:1319.
Kaledin et al. Biochem. 47:1515-1521 (1982): Biokhimiya (1982) 47:1785-1791.
Sanger et al. Proc. Natl. Acad. Sci. USA (1977) 74:5463.
Hamal et al. Eur. J. Biochem. (1990) 190:517-521.
Salhi et al. Biochem. Biophys. Res. Comm. (1990) 167:1341-1347.
Salhi et al. J. Mol. Biol. (1989) 209:635-641.
Rella et al. Ital. J. Biochem. (1990) 39:83-99.
Forterre et al. Can. J. Microbiol. (1989) 35:228-233.
Rossi et al. System. Appl. Microbiol. (1986) 7:337-341.
Klimczak et al. Nucleic Acids Res. (1985) 13:5269-5282.
Elie et al. Biochim. Biophys. Acta (1988) 951 :261-267.
Sellmann et al. J. Bacteriol.(1992) 174:4350-4355.
Kaboev et al. J. Bacteriol. (1981)145:21-26.
Klimczak et al. Biochem. (1986) 25:4850-4855.
Kong et. al. J. Biol. Chem.(1993) 268: 1965.
Lundberg et al. Gene (1991) 108:1.
A.T. Bankier, "Dideoxy sequencing reactions using Klenow fragment DNA polymerase I," in H. and A Griffin (eds.), Methods in Molecular Biology;: DNA Sequencing Protocols Humana Press Totowa NJ 1993 pp. 83-90.
Lawyer et al., J. Biol. Chem., (1989) 264:6427-6437.
Lawyer et al. PCR Meth. Appl. (1993) 2:275-287.
Sambrook et al. 1989 Nucleic Acid Hybridization A Practical Approach IRL Press Washington D.C. (1985).
Anderson and Young. Quantitative Filter Hybridization in Nucleic Acid Hybridization (1985).
C.R. Newton et al. PCR 2nd Ed. Springer-Verlag (1997), D. 24.
Maniatis et al. Science (1987) 236:1237.
Voss et al. Trends Biochem. Sci. (1986) 11:287.
Diikema et al. EMBO J.(1985) 4:761.
Uetsuki et al. J. Biol. Chem. (1989) 264:5791.
Mizushima and Nagata, Nuc. Acids. Res. (1990) 18:5322.
Gorman et al. Proc. Natl. Acad. Sci. USA (1982) 79:6777.
Boshart et al. Cell (1985) 41:521.
Kim etal. Gene (1990) 91:217.
Sambrook et al. Molecular Cloning: A Laboratory Manual 2nd ed. Cold Spring Harbor Laboratoy Press New York (1989) pp. 16.7-16.8.
Kornberg, DNA Replication W.H. Freeman and Co. San Francisco, (1980) pp. 127-139.
Tindall and Kunkell Biochem (1988) 27:6008.
Brutlag. Biochem. Biopys. Res. Commun. (1969) 37:982.
Erlich et al. Science (1991) 252: 1643.
Bebenek et al. J. Biol. Chem. (1990) 265:13878.
Barnes, Gene (1992) 112:29.
Bernad et al. Cell (1989) 59:219.
Wahl et al. Methods Enzymol. (1987) 152:399-407.
Davis et al. Basic Methods in Molecular Biology (1986).
Ben-Bassat et al. J. Bacteriol. (1987) 169:751-757.
Miller, PNAS (1990) 84:2718-1722.
Stryer ed. Biochemistry. 2nd ed WH Freeman and Co. (1981) p. 17-21.
Narang, Tetrahedron (1983) 39:39.
Itakura et al. Recombinant DNA Proc 3rd Cleveland Sympos. Macromol. Walton ed. Elsevier Amsterdam (1981) pp. 273-289.
Itakura et al. Annu. Rev. Biochem. (1984) 53:323.
Ike et al. Nucleic Acid Res. (1983) I 1:477.
Scott et al. Science (1980) 249:386-390.
Roberts et al. PNAS (1992) 89:2429-2433.
Devlin et al., Science (1990) 249: 404-406.
Cwirla et al., PNAS (1990) 87: 6378-6382.
Marks et al., J. Biol. Chem., (1992) 267:16007-16010.
Griffiths et al., EMBO (1993) 1., 12:725-734.
Clackson et al., Nature, (1991)352:624-628.
Barbas et al., PNAS (1992) 89:4457-4461.
Ruf et al., Biochem., (1994) 33: 1565-1572.
Wang et al., 1. Biol. Chem., (1994) 269:3095-3099.
Balint et al. Gene (1993) 137:109-118.
Grodbergetal, Eur. J. Biochem., (1993) 218:597-601.
Nagashima et al., J. Biol. Chem., (1993) 268:2888-2892.
Lowman et al., Biochem.,(1991) 30: 10832-10838.
Cunningham et al., Science, (1989) 244:1081-1085.
Gustin et al., Virol., (1993) 193:653-660.
Brown et al., Mol. Cell. Biol., (1992) 12:2644-2652.
Meyers et al., Science, (1986) 232:613.
Caruthers et al., Nuc. Acids Res. Symp. Ser., (1980) 7:215-233.
Crea and Hom, Nuc. Acids Res., (1980) 9:2331.
Matteucci and Caruthers, Tetrahedron Lett., (1980) 21 :719.
Chow and Kempe, Nuc.Acids Res., (1981) 9:2807-2817.
Creighton, Proteins Structures and Molecular Principles, W H Freeman and Co, New York N.Y. (1983).
Roberge et al., Science (1995) 269:202-204.
Innis et al., Proc. Natl. Acad. Sci USA(1988) 85:9436.
Maxam and Gilbert, Proc. Natl. Acad. Sci. USA (1977) 74:560.
Itakura et al., Science (1984) 198: I056.
Riley et al., Thermophiles Science Technology (1992) pp. I-II.

* cited by examiner

FIGURE 1

Nucleotide sequence of full-length *Tvu* DNA polymerase (SEQ ID NO: 1)

```
TTGAAAAACA AGCTCGTCTT AATTGACGGC AACAGCGTGG CGTACCGCGC    50
CTTTTTCGCG TTGCCGCTTT TGCATAACGA TAAAGGGATT CATACGAACG   100
CAGTCTACGG GTTTACGATG ATGTTAAACA AAATTTTGGC GGAAGAGCAG   150
CCGACCCACA TTCTCGTGGC GTTTGACGCC GGGAAAACGA CGTTCCGCCA   200
TGAAACGTTC CAAGACTATA AAGGCGGGCG GCAGCAGACG CCGCCGGAAC   250
TGTCGGAACA GTTTCCGCTG CTGCGCGAAT TGCTCAAGGC GTACCGCATC   300
CCCGCCTATG AGCTCGACCA TTACGAAGCG GACGATATTA TCGGAACGAT   350
GGCGGCGCGG GCTGAGCGGG AAGGGTTTGC AGTGAAAGTC ATTTCCGGCG   400
ACCGCGATTT AACCCAGCTT GCTTCCCCGC AAGTGACGGT GGAGATTACG   450
AAAAAAGGGA TTACCGACAT CGAGTCGTAC ACGCCGGAGA CGGTCGCGGA   500
AAAATACGGC CTCACCCCGG AGCAAATTGT CGACTTGAAA GGATTGATGG   550
GCGACAAATC CGACAACATC CCCGGCGTGC CCGGCATCGG GGAAAAAACA   600
GCCGTCAAGC TGCTCAAGCA ATTCGGCACG GTCGAAAACG TACTGGCATC   650
GATCGATGAG ATCAAAGGGG AGAAGCTGAA AGAAAATTTG CGCCAATACC   700
GGGATTTGGC GCTTTTAAGC AAACAGCTGG CCGCCATTCG CCGCGACGCC   750
CCAGTTGAGC TGACGCTCGA TGACATTGTC TACAAAGGAG AAGACCGGGA   800
AAAAGTGGTC GCCTTATTTA AGGAGCTCGG GTTCCAGTCG TTTCTCGACA   850
AGATGGCCGT CCAAACGGAT GAAGGCGAGA AGCCGCTCGC CGGGATGGAC   900
TTTGCGATCG CCGACGGCGT CACGGACGAA ATGCTCGCCG ACAAGGCGGC   950
CCTCGTCGTG GAGGTGGTGG GCGACAACTA TCACCATGCC CCGATTGTCG  1000
GGATCGCCTT GGCCAACGAA CGCGGGCGGT TTTTCCTGCG CCCGGAGACG  1050
GCGCTCGCCG ATCCGAAATT TCTCGCTTGG CTTGGCGATG AGACGAAGAA  1100
AAAAACGATG TTTGATTCAA AGCGGGCGGC CGTCGCGTTA AAATGGAAAG  1150
GAATCGAACT GCGCGGCGTC GTGTTCGATC TGTTGCTGGC CGCTTACTTG  1200
CTCGATCCGG CGCAGGCGGC GGGCGACGTT GCCGCGGTGG CGAAAATGCA  1250
TCAGTACGAG GCGGTGCGGT CGGATGAGGC GGTCTATGGA AAAGGAGCGA  1300
AGCGGACGGT TCCTGATGAA CCGACGCTTG CCGAGCATCT CGCCCGCAAG  1350
GCGGCGGCCA TTTGGGCGCT TGAAGAGCCG TTGATGGACG AACTGCGCCG  1400
CAACGAACAA GATCGGCTGC TGACCGAGCT CGAACAGCCG CTGGCTGGCA  1450
TTTTGGCCAA TATGGAATTT ACTGGAGTGA AAGTGGACAC GAAGCGGCTT  1500
GAACAGATGG GGGCGGAGCT CACCGAGCAG CTGCAGGCGG TCGAGCGGCG  1550
CATTTACGAA CTCGCCGGCC AAGAGTTCAA CATTAACTCG CCGAAACAGC  1600
TCGGGACGGT TTTATTTGAC AAGCTGCAGC TCCCGGTGTT GAAAAAGACA  1650
AAAACCGGCT ATTCGACTTC AGCCGATGTG CTTGAGAAGC TTGCACCGCA  1700
CCATGAAATC GTCAACATA TTTTGCATTA CCGCCAACTC GGCAAGCTGC  1750
AGTCAACGTA TATTGAAGGG CTGCTGAAAG TGGTGCACCC CGTGACGGGC  1800
AAAGTGCACA CGATGTTCAA TCAGGCGTTG ACGCAAACCG GCGCCTCAG   1850
CTCCGTCGAA CCGAATTTGC AAAACATTCC GATTCGGCTT GAGGAAGGGC  1900
GGAAAATCCG CCAGGCGTTC GTGCCGTCGG AGCCGGACTG GCTCATCTTT  1950
GCGGCCGACT ATTCGCAAAT CGAGCTGCGC GTCCTCGCCC ATATCGCGGA  2000
AGATGACAAT TTGATTGAAG CGTTCCGGCG CGGGTTGGAC ATCCATACGA  2050
AAACAGCCAT GGACATTTTC CATGTGAGCG AAGAAGACGT GACAGCCAAC  2100
ATGCGCCGCC AAGCGAAGGC CGTCAATTTT GGCATCGTGT ACGGCATTAG  2150
TGATTACGGT CTGGCGCAAA ACTTGAACAT TACGCGCAAA GAAGCGGCTG  2200
AATTTATTGA GCGATATTTT GCCAGTTTTC CAGGTGTAAA GCAATATATG  2250
GACAACACTG TGCAAGAAGC GAAACAAAAA GGGTATGTGA CGACGCTGCT  2300
GCATCGGCGC CGCTATTTGC CCGATATTAC AAGCCGCAAC TTCAACGTCC  2350
GCAGCTTCGC CGAGCGGACG GCGATGAACA CACCGATTCA AGGGAGCGCC  2400
GCTGATATTA TTAAAAAAGC GATGATCGAT CTAAGCGTGA GGCTGCGCGA  2450
AGAACGGCTG CAGGCGCGCC TGTTGCTGCA AGTGCATGAC GAACTCATTT  2500
TGGAGGCGCC GAAAGAGGAA ATCGAGCGGC TGTGCCGCCT CGTTCCAGAG  2550
GTGATGGAGC AAGCCGTCGC ACTCCGCGTG CCGCTGAAAG TCGATTACCA  2600
TTACGGTCCG ACGTGGTACG ACGCCAAATA A                      2631
```

Figure 2

Amino Acid Sequence of Full-length *Tvu* DNA Polymerase (SEQ ID NO: 2)

```
LKNKLVLIDG NSVAYRAFFA LPLLHNDKGI HTNAVYGFTM MLNKILAEEQ    50
PTHILVAFDA GKTTFRHETF QDYKGGRQQT PPELSEQFPL LRELLKAYRI   100
PAYELDHYEA DDIIGTMAAR AEREGFAVKV ISGDRDLTQL ASPQVTVEIT   150
KKGITDIESY TPETVAEKYG LTPEQIVDLK GLMGDKSDNI PGVPGIGEKT   200
AVKLLKQFGT VENVLASIDE IKGEKLKENL RQYRDLALLS KQLAAIRRDA   250
PVELTLDDIV YKGEDREKVV ALFKELGFQS FLDKMAVQTD EGEKPLAGMD   300
FAIADGVTDE MLADKAALVV EVVGDNYHHA PIVGIALANE RGRFFLRPET   350
ALADPKFLAW LGDETKKKTM FDSKRAAVAL KWKGIELRGV VFDLLLAAYL   400
LDPAQAAGDV AAVAKMHQYE AVRSDEAVYG KGAKRTVPDE PTLAEHLARK   450
AAAIWALEEP LMDELRRNEQ DRLLTELEQP LAGILANMEF TGVKVDTKRL   500
EQMGAELTEQ LQAVERRIYE LAGQEFNINS PKQLGTVLFD KLQLPVLKKT   550
KTGYSTSADV LEKLAPHHEI VEHILYRQL  GKLQSTYIEG LLKVVHPVTG   600
KVHTMFNQAL TQTGRLSSVE PNLQNIPIRL EEGRKIRQAF VPSEPDWLIF   650
AADYSQIELR VLAHIAEDDN LIEAFRRGLD IHTKTAMDIF HVSEEDVTAN   700
MRRQAKAVNF GIVYGISDYG LAQNLNITRK EAAEFIERYF ASFPGVKQYM   750
DNTVQEAKQK GYVTTLLHRR RYLPDITSRN FNVRSFAERT AMNTPIQGSA   800
ADIIKKAMID LSVRLREERL QARLLLQVHD ELILEAPKEE IERLCRLVPE   850
VMEQAVALRV PLKVDYHYGP TWYDAK                            876
```

Figure 3

Nucleotide Sequence of M285 (SEQ ID NO: 3)

```
ATGGCCGTCC AAACGGATGA AGGCGAGAAG CCGCTCGCCG GGATGGACTT    50
TGCGATCGCC GACGGCGTCA CGGACGAAAT GCTCGCCGAC AAGGCGGCCC   100
TCGTCGTGGA GGTGGTGGGC GACAACTATC ACCATGCCCC GATTGTCGGG   150
ATCGCCTTGG CCAACGAACG CGGGCGGTTT TTCCTGCGCC GGAGACGGC    200
GCTCGCCGAT CCGAAATTTC TCGCTTGGCT TGGCGATGAG ACGAAGAAAA   250
AAACGATGTT TGATTCAAAG CGGGCGGCCG TCGCGTTAAA ATGGAAAGGA   300
ATCGAACTGC GCGGCGTCGT GTTCGATCTG TTGCTGGCCG CTTACTTGCT   350
CGATCCGGCG CAGGCGGCGG CGACGTTGC CGCGGTGGCG AAAATGCATC    400
AGTACGAGGC GGTGCGGTCG GATGAGGCGG TCTATGGAAA AGGAGCGAAG   450
CGGACGGTTC CTGATGAACC GACGCTTGCC GAGCATCTCG CCCGCAAGGC   500
GGCGGCCATT TGGGCGCTTG AAGAGCCGTT GATGGACGAA CTGCCCGCA    550
ACGAACAAGA TCGGCTGCTG ACCGAGCTCG AACAGCCGCT GGCTGGCATT   600
TTGGCCAATA TGGAATTTAC TGGAGTGAAA GTGGACACGA AGCGGCTTGA   650
ACAGATGGGG GCGGAGCTCA CCGAGCAGCT GCAGGCGGTC GAGCGGCGCA   700
TTTACGAACT CGCCGGCCAA GAGTTCAACA TTAACTCGCC GAAACAGCTC   750
GGGACGGTTT TATTTGACAA GCTGCAGCTC CCGGTGTTGA AAAAGACAAA   800
AACCGGCTAT TCGACTTCAG CCGATGTGCT TGAGAAGCTT GCACCGCACC   850
ATGAAATCGT CGAACATATT TTGCATTACC GCCAACTCGG CAAGCTGCAG   900
TCAACGTATA TTGAAGGGCT GCTGAAAGTG GTGCACCCCG TGACGGGCAA   950
AGTGCACACG ATGTTCAATC AGGCGTTGAC GCAAACCGGG CGCCTCAGCT  1000
CCGTCGAACC GAATTTGCAA AACATTCCGA TTCGGCTTGA GGAAGGGCGG  1050
AAAATCCGCC AGGCGTTCGT GCCGTCGGAG CCGGACTGGC TCATCTTTGC  1100
GGCCGACTAT TCGCAAATCG AGCTGCGCGT CCTCGCCCAT ATCGCGGAAG  1150
ATGACAATTT GATTGAAGCG TTCCGGCGCG GGTTGGACAT CCATACGAAA  1200
ACAGCCATGG ACATTTTCCA TGTGAGCGAA GAAGACGTGA CAGCCAACAT  1250
GCGCCGCCAA GCGAAGGCCG TCAATTTTGG CATCGTGTAC GGCATTAGTG  1300
ATTACGGTCT GGCGCAAAAC TTGAACATTA CGCGCAAAGA AGCGGCTGAA  1350
TTTATTGAGC GATATTTTGC CAGTTTTCCA GGTGTAAAGC AATATATGGA  1400
CAACACTGTG CAAGAAGCGA AACAAAAAGG GTATGTGACG ACGCTGCTGC  1450
ATCGGCGCCG CTATTTGCCC GATATTACAA GCCGCAACTT CAACGTCCGC  1500
AGCTTCGCCG AGCGGACGGC GATGAACACA CCGATTCAAG GGAGCGCCGC  1550
TGATATTATT AAAAAAGCGA TGATCGATCT AAGCGTGAGG CTGCGCGAAG  1600
AACGGCTGCA GGCGCGCCTG TTGCTGCAAG TGCATGACGA ACTCATTTTG  1650
GAGGCGCCGA AAGAGGAAAT CGAGCGGCTG TGCCGCCTCG TTCCAGAGGT  1700
GATGGAGCAA GCCGTCGCAC TCCGCGTGCC GCTGAAAGTC GATTACCATT  1750
ACGGTCCGAC GTGGTACGAC GCCAAATAA                         1779
```

Figure 4

Amino Acid Sequence of M285 (SEQ ID NO: 4)

```
MAVQTDEGEK PLAGMDFAIA DGVTDEMLAD KAALVVEVVG DNYHHAPIVG    50
IALANERGRF FLRPETALAD PKFLAWLGDE TKKKTMFDSK RAAVALKWKG   100
IELRGVVFDL LLAAYLLDPA QAAGDVAAVA KMHQYEAVRS DEAVYGKGAK   150
RTVPDEPTLA EHLARKAAAI WALEEPLMDE LRRNEQDRLL TELEQPLAGI   200
LANMEFTGVK VDTKRLEQMG AELTEQLQAV ERRIYELAGQ EFNINSPKQL   250
GTVLFDKLQL PVLKKTKTGY STSADVLEKL APHHEIVEHI LHYRQLGKLQ   300
STYIEGLLKV VHPVTGKVHT MFNQALTQTG RLSSVEPNLQ NIPIRLEEGR   350
KIRQAFVPSE PDWLIFAADY SQIELRVLAH IAEDDNLIEA FRRGLDIHTK   400
TAMDIFHVSE EDVTANMRRQ AKAVNFGIVY GISDYGLAQN LNITRKEAAE   450
FIERYFASFP GVKQYMDNTV QEAKQKGYVT TLLHRRRYLP DITSRNFNVR   500
SFAERTAMNT PIQGSAADII KKAMIDLSVR LREERLQARL LLQVHDELIL   550
EAPKEEIERL CRLVPEVMEQ AVALRVPLKV DYHYGPTWYD AK           592
```

Figure 5

Nucleotide Sequence of T289M (SEQ ID NO: 5)

```
ATGGATGAAG GCGAGAAGCC GCTCGCCGGG ATGGACTTTG CGATCGCCGA    50
CGGCGTCACG GACGAAATGC TCGCCGACAA GGCGGCCCTC GTCGTGGAGG   100
TGGTGGGCGA CAACTATCAC CATGCCCCGA TTGTCGGGAT CGCCTTGGCC   150
AACGAACGCG GCGGTTTTT  CCTGCGCCCG GAGACGGCGC TCGCCGATCC   200
GAAATTTCTC GCTTGGCTTG GCGATGAGAC GAAGAAAAA  ACGATGTTTG   250
ATTCAAAGCG GCGGCCGTC  GCGTTAAAAT GGAAAGGAAT CGAACTGCGC   300
GGCGTCGTGT TCGATCTGTT GCTGGCCGCT TACTTGCTCG ATCCGGCGCA   350
GGCGGCGGGC GACGTTGCCG CGGTGGCGAA AATGCATCAG TACGAGGCGG   400
TGCGGTCGGA TGAGGCGGTC TATGGAAAAG GAGCGAAGCG GACGGTTCCT   450
GATGAACCGA CGCTTGCCGA GCATCTCGCC CGCAAGGCGG CGGCCATTTG   500
GGCGCTTGAA GAGCCGTTGA TGGACGAACT GCGCCGCAAC GAACAAGATC   550
GGCTGCTGAC CGAGCTCGAA CAGCCGCTGG CTGGCATTTT GGCCAATATG   600
GAATTTACTG GAGTGAAAGT GGACACGAAG CGGCTTGAAC AGATGGGGGC   650
GGAGCTCACC GAGCAGCTGC AGGCGGTCGA GCGGCGCATT TACGAACTCG   700
CCGGCCAAGA GTTCAACATT AACTCGCCGA ACAGCTCGG  ACGGTTTTA    750
TTTGACAAGC TGCAGCTCCC GGTGTTGAAA AAGACAAAAA CCGGCTATTC   800
GACTTCAGCC GATGTGCTTG AGAAGCTTGC ACCGCACCAT GAAATCGTCG   850
AACATATTTT GCATTACCGC CAACTCGGCA AGCTGCAGTC AACGTATATT   900
GAAGGGCTGC TGAAAGTGGT GCACCCCGTG ACGGGCAAAG TGCACACGAT   950
GTTCAATCAG GCGTTGACGC AAACCGGGCG CCTCAGCTCC GTCGAACCGA  1000
ATTTGCAAAA CATTCCGATT CGGCTTGAGG AAGGGCGGAA AATCCGCCAG  1050
GCGTTCGTGC CGTCGGAGCC GGACTGGCTC ATCTTTGCGG CCGACTATTC  1100
GCAAATCGAG CTGCGCGTCC TCGCCCATAT CGCGGAAGAT GACAATTTGA  1150
TTGAAGCGTT CCGGCGCGGG TTGGACATCC ATACGAAAAC AGCCATGGAC  1200
ATTTTCCATG TGAGCGAAGA AGACGTGACA GCCAACATGC GCCGCCAAGC  1250
GAAGGCCGTC AATTTTGGCA TCGTGTACGG CATTAGTGAT TACGGTCTGG  1300
CGCAAAACTT GAACATTACG CGCAAGAAG  CGGCTGAATT TATTGAGCGA  1350
TATTTTGCCA GTTTTCCAGG TGTAAAGCAA TATATGGACA ACACTGTGCA  1400
AGAAGCGAAA CAAAAAGGGT ATGTGACGAC GCTGCTGCAT CGGCGCCGCT  1450
ATTTGCCCGA TATTACAAGC CGCAACTTCA ACGTCCGCAG CTTCGCCGAG  1500
CGGACGGCGA TGAACACACC GATTCAAGGG AGCGCCGCTG ATATTATTAA  1550
AAAAGCGATG ATCGATCTAA GCGTGAGGCT GCGCGAAGAA CGGCTGCAGG  1600
CGCGCCTGTT GCTGCAAGTG CATGACGAAC TCATTTTGGA GGCGCCGAAA  1650
GAGGAAATCG AGCGGCTGTG CCGCCTCGTT CCAGAGGTGA TGGAGCAAGC  1700
CGTCGCACTC CGCGTGCCGC TGAAAGTCGA TTACCATTAC GGTCCGACGT  1750
GGTACGACGC CAAATAA                                     1767
```

Figure 6

Amino Acid Sequence of T289M (SEQ ID NO: 6)

```
TDEGEKPLAG MDFAIADGVT DEMLADKAAL VVEVVGDNYH HAPIVGIALA  50
NERGRFFLRP ETALADPKFL AWLGDETKKK TMFDSKRAAV ALKWKGIELR 100
GVVFDLLLAA YLLDPAQAAG DVAAVAKMHQ YEAVRSDEAV YGKGAKRTVP 150
DEPTLAEHLA RKAAAIWALE EPLMDELRRN EQDRLLTELE QPLAGILANM 200
EFTGVKVDTK RLEQMGAELT EQLQAVERRI YELAGQEFNI NSPKQLGTVL 250
FDKLQLPVLK KTKTGYSTSA DVLEKLAPHH EIVEHILHYR QLGKLQSTYI 300
EGLLKVVHPV TGKVHTMFNQ ALTQTGRLSS VEPNLQNIPI RLEEGRKIRQ 350
AFVPSEPDWL IFAADYSQIE LRVLAHIAED DNLIEAFRRG LDIHTKTAMD 400
IFHVSEEDVT ANMRRQAKAV NFGIVYGISD YGLAQNLNIT RKEAAEFIER 450
YFASFPGVKQ YMDNTVQEAK QKGYVTTLLH RRRYLPDITS RNFNVRSFAE 500
RTAMNTPIQG SAADIIKKAM IDLSVRLREE RLQARLLLQV HDELILEAPK 550
EEIERLCRLV PEVMEQAVAL RVPLKVDYHY GPTWYDAK            588
```

Figure 7

SEQ ID NO: 19, complete coding sequence for *Bacillus stearothermophilus* DNA polymerase 1, Genbank Accession No. U33536.

```
   1 atgaagaaga agctagtact aattgatggc aacagtgtgg cataccgcgc cttttttgcc
  61 ttgccacttt tgcataacga caaaggcatt catacgaatg cggtttacgg gtttacgatg
 121 atgttgaaca aaattttggc ggaagaacaa ccgacccatt tacttgtagc gtttgacgcc
 181 ggaaaaacga cgttccggca tgaaacgttt caagagtata aaggcggacg gcaacaaact
 241 cccccggaac tgtccgagca gtttccgctg ttgcgcgagc tattaaaagc gtaccgcatt
 301 cccgcttatg aacttgatca ttacgaagcg gacgatatta tcgggacgct cgctgcccgc
 361 gctgagcaag aagggtttga agtgaaaatc atttccggcg accgcgattt aacccagctc
 421 gcctccgtc atgtgacggt cgatattacg aaaaaaggga ttaccgacat tgagccgtat
 481 acgccagaga ccgttcgcga aaaatacggc ctgactccgg agcaaatagt ggatttaaaa
 541 ggattgatgg gcgataaatc cgacaacatc ccgggcgtgc ccggcatcgg ggaaaaaacg
 601 gcggtcaagc tgctgaagca atttggtacg gtggaaaatg tgctcgcatc gattgatgag
 661 gtgaagggg aaaaactgaa agaaacttg cgccaacacc gggatttagc tctcttgagc
 721 aaacagctgg cgtccatttg ccgcgacgcc ccggttgagc tgtcgttaga tgacattgtc
 781 tacgaaggac aagaccgcga aaaagtcatc gcgttattta agaactcgg gtttcagtcg
 841 ttcttggaaa aaatggccgc gccggcagcc gaaggggaga accgcttga ggagatggag
 901 tttgccatcg ttgacgtcat taccgaagag atgcttgccg acaaggcagc gcttgtcgtt
 961 gaggtgatgg aagaaaacta ccacgatgcc ccgattgtcg gaatcgcact agtgaacgag
1021 catgggcgat tttttatgcg cccggagacc gcgctggctg attcgcaatt tttagcatgg
1081 cttgccgatg aaacgaagaa aaaaagcatg tttgacgcca agcgggcagt cgttgcctta
1141 aagtggaaag gaattgagct tcgcggcgtc gcctttgatt tattgctcgc tgcctatttg
1201 ctcaatccgg ctcaagatgc cggcgatatc gctgcggtgg cgaaaatgaa acaatatgaa
1261 gcggtgcggt cggatgaagc ggtctatggc aaaggcgtca agcggtcgct gccggacgaa
1321 cagacgcttg ctgagcatct cgttcgcaaa gcggcagcca tttgggcgct tgagcagcg
1381 tttatggacg atttgcggaa caacgaacaa gatcaattat taacgaagct tgagcagccg
1441 ctggcggcga tttttggctga aatggaattc actggggtga acgtggatac aaagcggctt
1501 gaacagatgg gttcggagct cgccgaacaa ctgcgtgcca tcgagcagcg catttacgag
1561 ctagccggcc aagagttcaa cattaactca ccaaaacagc tcggagtcat tttatttgaa
1621 aagctgcagc taccggtgct gaagaagacg aaaacaggct attcgacttc ggctgatgtg
1681 cttgagaagc ttgcgccgca tcatgaaatc gtcgaaaaca ttttgcatta ccgccagctt
1741 ggcaaactgc aatcaacgta tattgaagga ttgttgaaag ttgtgcgccc tgataccggc
1801 aaagtgcata cgatgttcaa ccaagcgctg acgcaaactg ggcggctcag ctcggccgag
1861 ccgaacttgc aaaacattcc gattcggctc gaagaggggc ggaaaatccg ccaagcgttc
1921 gtcccgtcag agccggactg gctcattttc gccgccgatt actcacaaat tgaattgcgc
1981 gtcctcgccc atatcgccga tgacgacaat ctaattgaag cgttccaacg cgatttggat
2041 attcacacaa aaacggcgat ggacattttc catgtgagcg aagaggaagt cacgccaac
2101 atgcgccgcc aggcaaaggc cgttaacttc ggtatcgttt acggaattag cgattacgga
2161 ttggcgcaaa acttgaacat tacgcgcaaa gaagctgccg aatttatcga acgttacttc
2221 gccagctttc cgggcgtaaa gcagtatatg gaaaacattg tgcaagaagc gaaacagaaa
2281 ggatatgtga caacgctgtt gcatcggcgc cgctatttgc ctgatattac aagccgcaat
2341 ttcaacgtcc gcagttttgc agagcggacg gccatgaaca cgccaattca aggaagcgcc
2401 gctgacatta ttaaaaaagc gatgattgat ttagcggcac ggctgaaaga agagcagctt
2461 caggctcgtc ttttgctgca agtgcatgac gagctcattt tggaagcgcc aaaagaggaa
2521 attgagcgat tatgtgagct tgttccggaa gtgatggagc aggccgttac gctccgcgtg
2581 ccgctgaaag tcgactacca ttacggccca acatggtatg atgccaaata a
```

Figure 8

SEQ ID NO: 20, amino acid sequence encoded by SEQ ID NO. 19.

MKKKLVLIDGNSVAYRAFFALPLLHNDKGIHTNAVYGFTMMLNK

ILAEEQPTHLLVAFDAGKTTFRHETFQEYKGGRQQTPPELSEQFPLLRELLKAYRIPA

YELDHYEADDIIGTLAARAEQEGFEVKIISGDRDLTQLASRHVTVDITKKGITDIEPY

TPETVREKYGLTPEQIVDLKGLMGDKSDNIPGVPGIGEKTAVKLLKQFGTVENVLASI

DEVKGEKLKENLRQHRDLALLSKQLASICRDAPVELSLDDIVYEGQDREKVIALFKEL

GFQSFLEKMAAPAAEGEKPLEEMEFAIVDVITEEMLADKAALVVEVMEENYHDAPIVG

IALVNEHGRFFMRPETALADSQFLAWLADETKKKSMFDAKRAVVALKWKGIELRGVAF

DLLLAAYLLNPAQDAGDIAAVAKMKQYEAVRSDEAVYGKGVKRSLPDEQTLAEHLVRK

AAAIWALEQPFMDDLRNNEQDQLLTKLEQPLAAILAEMEFTGVNVDTKRLEQMGSELA

EQLRAIEQRIYELAGQEFNINSPKQLGVILFEKLQLPVLKKTKTGYSTSADVLEKLAP

HHEIVENILHYRQLGKLQSTYIEGLLKVVRPDTGKVHTMFNQALTQTGRLSSAEPNLQ

NIPIRLEEGRKIRQAFVPSEPDWLIFAADYSQIELRVLAHIADDDNLIEAFQRDLDIH

TKTAMDIFHVSEEEVTANMRRQAKAVNFGIVYGISDYGLAQNLNITRKEAAEFIERYF

ASFPGVKQYMENIVQEAKQKGYVTTLLHRRRYLPDITSRNFNVRSFAERTAMNTPIQG

SAADIIKKAMIDLAARLKEEQLQARLLLQVHDELILEAPKEEIERLCELVPEVMEQAV

TLRVPLKVDYHYGPTWYDAK

Figure 9

SEQ ID NO: 21, coding sequence for *Bacillus stearothermophilus* DNA polymerase 1 lacking 5' to 3' exonuclease activity, Genbank Accession No.: AR053713.

```
   1 gccgaagggg agaaaccgct tgaggagatg gagtttgcca tcgttgacgt cattaccgaa
  61 gagatgcttg ccgacaaggc agcgcttgtc gttgaggtga tggaagaaaa ctaccacgat
 121 gccccgattg tcggaatcgc actagtgaac gagcatgggc gattttttat gcgcccggag
 181 accgcgctgg ctgattcgca atttttagca tggcttgccg atgaaacgaa gaaaaaaagc
 241 atgtttgacg ccaagcgggc agtcgttgcc ttaaagtgga aaggaattga gcttcgcggc
 301 gtcgcctttg atttattgct cgctgcctat ttgctcaatc cggctcaaga tgccggcgat
 361 atcgctgcgg tggcgaaaat gaaacaatat gaagcggtgc ggtcggatga agcggtctat
 421 ggcaaaggcg tcaagcggtc gctgccggac gaacagacgc ttgctgagca tctcgttcgc
 481 aaagcggcag ccatttgggc gcttgagcag ccgtttatgg acgatttgcg gaacaacgaa
 541 caagatcaat tattaacgaa gcttgagcac gcgctggcgg cgatttggc tgaaatggaa
 601 ttcactgggg tgaacgtgga tacaaagcgg cttgaacaga tgggttcgga gctcgccgaa
 661 caactgcgtg ccatcgagca gcgcatttac gagctagccg gccaagagtt caacattaac
 721 tcaccaaaac agctcggagt cattttattt gaaaagctgc agctaccggt gctgaagaag
 781 acgaaaacag gctattcgac ttcggctgat gtgcttgaga agcttgcgcc gcatcatgaa
 841 atcgtcgaaa acatttgca ttaccgccag cttggcaaac tgcaatcaac gtatattgaa
 901 ggattgttga agttgtgcg ccctgatacc ggcaaagtgc atacgatgtt caaccaagcg
 961 ctgacgcaaa ctgggcggct cagctcggcc gagccgaact tgcaaaacat tccgattcgg
1021 ctcgaagagg ggcggaaaat ccgccaagcg ttcgtcccgt cagagccgga ctggctcatt
1081 ttcgccgccg attactcaca aattgaattg cgcgtcctcg cccatatcgc cgatgacgac
1141 aatctaattg aagcgttcca acgcgatttg gatattcaca caaaaacggc gatggacatt
1201 ttccagttga gcgaagagga agtcacggcc aacatgcgcc gccaggcaaa ggccgttaac
1261 ttcggtatcg tttacggaat tagcgattac ggattggcgc aaaacttgaa cattacgcgc
1321 aaagaagctg ccgaatttat cgaacgttac ttcgccagct ttccgggcgt aaagcagtat
1381 atggaaaaca tagtgcaaga agcgaaacag aaaggatatg tgacaacgct gttgcatcgg
1441 cgccgctatt tgcctgatat tacaagccgc aatttcaacg tccgcagttt tgcagagcgg
1501 acggccatga acacgccaat tcaaggaagc gccgctgaca ttattaaaaa agcgatgatt
1561 gatttagcgg cacggctgaa agaagagcag cttcaggctc gtctttgct gcaagtgcat
1621 gacgagctca ttttggaagc gccaaaagag gaattgagc gattatgtga gcttgttccg
1681 gaagtgatgg agcaggccgt tacgctccgc gtgccgctga aagtcgacta ccattacggc
1741 ccaacatggt atgatgccaa ataa
```

Figure 10

SEQ ID NO: 22, amino acid sequence encoded by SEQ ID NO: 21, Genbank Accession No. AAE15301.

```
  1 aegekpleem efaivdvite emladkaalv vevmeenyhd apivgialvn ehgrffmrpe
 61 taladsqfla wladetkkks mfdakravva lkwkgielrg vafdlllaay llnpaqdagd
121 iaavakmkqy eavrsdeavy gkgvkrslpd eqtlaehlvr kaaaiwaleq pfmddlrnne
181 qdqlltkleh alaailaeme ftgvnvdtkr leqmgselae qlraieqriy elagqefnin
241 spkqlgvilf eklqlpvlkk tktgystsad vleklaphhe ivenilhyrq lgklqstyie
301 gllkvvrpdt gkvhtmfnqa ltqtgrlssa epnlqnipir leegrkirqa fvpsepdwli
361 faadysqiel rvlahiaddd nlieafqrdl dihtktamdi fqlseeevta nmrrqakavn
421 fgivygisdy glaqnlnitr keaaefiery fasfpgvkqy menivqeakq kgyvttllhr
481 rrylpditsr nfnvrsfaer tamntpiqgs aadiikkami dlaarlkeeq lqarlllqvh
541 delileapke eierlcelvp evmeqavtlr vplkvdyhyg ptwydak
```

METHOD OF REVERSE TRANSCRIPTION

The present application is a Continuation of U.S. application Ser. No. 10/178,673, filed Jun. 24, 2002, now U.S. Pat. No. 7,094,539, which in turn is a Continuation of U.S. application Ser. No. 09/517,871, filed Mar. 2, 2000, now U.S. Pat. No. 6,436,677, both of which are herein incorporated by reference.

FIELD OF THE INVENTION

The present invention relates to reverse transcription of RNA, and in particular to thermostable DNA polymerases that have reverse transcriptase activity.

BACKGROUND

Many ribonucleic acid (RNA) molecules contain secondary structure that results from hybridization between complementary regions within the RNA molecule. A variety of secondary structures can be formed, including hairpins and cruciforms. RNA molecules containing secondary structure are often difficult to reverse transcribe because polymerases cannot readily process through the secondary structure.

Because of the difficulty of reverse transcribing RNA molecules with secondary structure, many techniques dependent upon reverse transcription yield anomalous results. For example, RNA molecules with secondary structure may be poorly represented in cDNA libraries. Populations of RNA with secondary structure may also yield cDNA libraries with a short insert size. Furthermore, RNA molecules containing secondary structure may be difficult to detect in assays such as reverse transcription-polymerase chain reaction (RT-PCR).

Traditionally, reverse transcription has been performed with reverse transcriptases encoded by retroviruses (e.g., avian myoblastosis virus (AMV) reverse transcriptase and Moloney murine leukemia virus (MMLV) reverse transcriptase). Several mesophillic DNA polymerases (e.g., *E. coli* DNA polymerase I) have also been shown to possess reverse transcriptase activity. However, these enzymes are generally used at temperatures of between about 37° C. to 42° C., a temperature range where secondary structure can be a significant problem.

Several thermophilic DNA polymerases (e.g., *Thermus aquaticus* DNA polymerase and *Thermus thermophilus* DNA polymerase) also have reverse transcriptase activity. These enzymes are useful for reverse transcription, because at the high temperatures where such enzymes are stable, secondary structure in RNA molecules is reduced. Furthermore, such enzymes can be used to directly synthesize second strand DNA and potentially even to directly amplify an RNA target. However, the utility of these thermostable enzymes is limited because they require manganese as a co-factor for reverse transcriptase activity (e.g., U.S. Pat. No. 5,322,770) resulting in deleterious effects. In some cases, the fidelity of the polymerase is reduced as compared to the fidelity of the enzyme in the presence of other cofactors, such as magnesium ions. Therefore, it is not desirable to amplify the template in the same reaction mixture in which reverse transcription reaction is conducted. This necessitates extra time consuming steps when performing RT-PCR. In other cases, the presence of manganese ions may also cause degradation of the RNA template.

Accordingly, what is needed in the art are alternative thermostable polymerases that have reverse transcriptase activity. Preferably, such thermostable polymerases should have reverse transcriptase activity in the presence of magnesium so that high-fidelity cDNAs may be obtained and so that both reverse transcription and amplification in RT-PCR reactions may conducted in the same reaction mixture.

SUMMARY OF THE INVENTION

The present invention relates to reverse transcription of RNA templates, and in particular to reverse transcription by thermostable DNA polymerases. The present invention is not limited to any particular RNA template. Indeed, a variety of RNA templates are contemplated. Examples of RNA templates include, but are not limited to, mRNA, rRNA, purified RNA, mixtures of mRNA, mixtures of rRNA and mRNA, and purified preparations of these various RNAs.

The present invention is not limited to the use of a particular thermostable DNA polymerase. Indeed, the use of a variety of thermostable DNA polymerases is contemplated. In some embodiments, the thermostable DNA polymerase is selected from *Thermoactinomyces vulgaris* (Tvu) and *Bacillus stearothermophilus* (Bst) DNA polymerases. In some embodiments, the thermostable DNA polymerase is purified from natural sources, while in other embodiments, the DNA polymerase is generated by recombinant techniques. In still other embodiments, the thermostable DNA polymerase lacks significant 5' exonuclease activity. In some embodiments, the Tvu polymerase is encoded by an amino acid sequence selected from SEQ ID NO: 2, SEQ ID NO: 4, and SEQ ID NO 6, and variants or portions thereof. In other embodiments, the Bst polymerase is encoded by an amino acid sequence selected from SEQ ID NO: 19 and SEQ ID NO: 21, and variants or portions thereof. In some embodiments, the present invention provides methods for reverse transcribing template RNA (i.e., making cDNA copies of the template RNA). In some embodiments, the method comprises a) providing: i) a polymerase selected from *T. vulgaris* and *B. stearothermophilus* DNA polymerases; ii) template RNA; iii) at least one primer; and iv) a reaction buffer comprising magnesium ions; b) combining the polymerase, template RNA, at least one primer, and reaction buffer to form a reaction mixture; and c) reacting said reaction mixture under conditions such that the template RNA is reverse transcribed, producing cDNA. The method is not limited by the order in which the polymerase, template RNA, at least one primer, and reaction buffer are combined. In some embodiments, the reaction buffer is substantially free of manganese ions. In other embodiments, the reacting step is performed at about 50 degrees Celsius to about 80 degrees Celsius, preferably at about 60 degrees Celsius to about 75 degrees Celsius. The method is not limited to a particular type of primer. Indeed a variety of primers may be used, including, but not limited to, oligonucleotides complementary to the 5' untranslated region of an mRNA, the coding region of an mRNA, or the 3' untranslated region of an mRNA, oligo(dT), and random primers (e.g., random hexamers or octamers). In still further embodiments, the method comprises the additional step d) amplifying the cDNA produced by the reverse transcription reaction.

The present invention also provides methods for detecting the presence of an RNA molecule in a sample by reverse transcription PCR (RT-PCR). In some embodiments, the reverse transcription and amplification reactions are conducted in the same reaction buffer (i.e., a single pot reaction is performed). In other embodiments, reverse transcription and amplification are performed in separate reactions (i.e., a two pot reaction is performed). Accordingly, in some embodiments, the method comprises: a) providing: i) a polymerase selected from *T. vulgaris* and *B. stearothermophilus* DNA polymerases; ii) a sample suspected of containing a target RNA; iii) at least a first primer and a second primer, wherein the first primer is complementary to the target RNA and the second primer is complementary to a cDNA copy of the target RNA; and iv) a reaction buffer comprising magnesium ions; b) mixing the polymerase, target RNA, reaction buffers, and primers to form a reaction mixture; c) reacting the reaction mixture under conditions such that the polymerase reverse transcribes the target RNA to produce first strand DNA; and d) reacting the first strand DNA with the second primer under conditions such that second strand DNA is produced; and e) reacting the first strand DNA, second strand DNA, first primer, and second primer under conditions such that a DNA molecule comprising a third strand and a fourth strand is produced, the third strand having a region of complementarity to the first strand and the fourth strand having a region of complementarity to the second strand. In some embodiments, the reaction mixture further comprises an additional thermostable polymerase (e.g., Taq DNA polymerase, Tne DNA polymerase, Pfu DNA polymerase, and the like). In some embodiments, the conditions further comprise heating the reaction mixture. In other embodiments, the conditions further comprise cooling the mixture to a temperature at which the thermostable DNA polymerase can conduct primer extension. In still further embodiments, the heating and cooling is repeated one or more times.

In still further embodiments, the present invention provides mixtures and kits for performing reverse transcription. In some embodiments, the mixture comprises a polymerase selected from *T. vulgaris* and *B. stearothermophilus* DNA polymerases, purified RNA, and magnesium ions. In other embodiments, the concentration of magnesium is from about 0.1 to 10 mM, preferably 1 to 5 mM. In another embodiment, the mixture further comprises a buffer. In still other embodiments, the mixture comprises a surfactant. In further embodiments, the mixture has a pH of about 6 to 10, preferably a pH of about 7 to 9. In some embodiments, the reaction mixture further comprises an additional thermostable polymerase (e.g., Taq DNA polymerase, Tne DNA polymerase, Pfu DNA polymerase, and the like)

In other embodiments of the present invention, a kit is provided. In some embodiments, the kit comprises a polymerase selected from *T. vulgaris* and *B. stearothermophilus* DNA polymerases, purified RNA as a control template, and a buffer comprising magnesium ions. In some embodiments, the kit contains instructions for performing reverse transcription. In other embodiments, the buffer further comprises a surfactant. In some embodiments, the pH of the buffer is from about 6 to 10, preferably a pH of about 7 to 9. In some embodiments, the kit comprises an additional thermostable polymerase (e.g., Taq DNA polymerase, Tne DNA polymerase, Pfu DNA polymerase, and the like)

The present invention also provides methods for amplifying a double stranded DNA molecule, comprising the steps of: a) providing: i) a first DNA molecule comprising a first strand and a second strand, wherein the first and second strands are complementary to one another; ii) a first primer and a second primer, wherein the first primer is complementary to the first DNA strand, and the second primer is complementary to the second DNA strand; and iii) a first thermostable DNA polymerase derived from *T. vulgaris*; and b) mixing the first DNA molecule, first primer, second primer, and polymerase to form a reaction mixture under conditions such that a second DNA molecule comprising a third strand and a fourth strand are synthesized, with the third strand having a region complementary to the first strand and the fourth strand having a region complementary to the second strand. In some embodiments, the reaction mixture further comprises an additional thermostable polymerase (e.g., Taq DNA polymerase, Tne DNA polymerase, Pfu DNA polymerase, and the like). The method of the present invention is not limited by the source of the first DNA molecule. In a preferred embodiment, the first DNA molecule is present in a genomic DNA mixture (e.g., in genomic DNA extracted from an organism, tissue or cell line). In alternative embodiments, the first DNA molecule is derived from an RNA molecule using reverse transcriptase-PCR (RT-PCR). The newly synthesized DNA molecule (cDNA) then serves as substrate in the subsequent amplification reaction. The conditions that permit the primer to hybridize to the DNA molecule, and allow the DNA polymerase to conduct primer extension may comprise the use of a buffer.

In one embodiment, the method comprises heating the mixture. In an alternative embodiment, the method further comprises cooling the mixture to a temperature at which the thermostable DNA polymerase can conduct primer extension. In a particularly preferred embodiment, the method comprises repeating the heating and cooling steps one or more times.

It is also contemplated that the polymerase of the method will have various useful properties. It is therefore contemplated that in one embodiment of the method, the Tvu polymerase lacks significant 5'-3' exonuclease activity. In other embodiments, the polymerase has reverse transcriptase activity in the presence of either magnesium or manganese ions. In still other embodiments, the reverse transcriptase activity in presence of magnesium ions is substantially manganese ion independent.

BRIEF DESCRIPTION OF THE DRAWINGS

FIG. 1 provides the single letter code nucleotide for the DNA sequence encoding full-length Tvu DNA polymerase (SEQ ID NO: 1).

FIG. 2 provides the predicted amino acid sequence of full-length Tvu DNA polymerase (SEQ ID NO: 2).

FIG. 3 provides the DNA sequence encoding the 5' to 3' exonuclease deletion mutant form of Tvu DNA polymerase called M285. This DNA sequence encodes the enzyme beginning at the nucleotides encoding the methionine amino acid at position 285 of wild type Tvu DNA polymerase and ending at the termination codon of the wild type enzyme (SEQ ID NO: 3).

FIG. 4 provides the predicted amino acid sequence of M285 Tvu DNA polymerase (SEQ ID NO: 4).

FIG. 5 provides the DNA sequence encoding the 5' to 3' exonuclease deletion mutant form of Tvu DNA polymerase called T289M. This DNA sequence encodes the enzyme beginning at amino acid 289 of the wild type Tvu DNA polymerase, mutated to encode a methionine instead of threonine that appears at this position in wild type, and ending at the termination codon of the wild type enzyme (SEQ ID NO: 5).

FIG. 6 provides the predicted amino acid sequence of T289M Tvu DNA polymerase (SEQ ID NO: 6).

FIG. 7 provides the complete coding sequence for *Bacillus stearothermophilus* DNA polymerase 1, Genbank Accession No. U33536 (SEQ ID NO: 18).

FIG. 8 provides the amino acid sequence (SEQ ID NO: 19) encoded by SEQ ID NO. 18.

FIG. 9 provides the coding sequence for *Bacillus stearothermophilus* DNA polymerase 1 lacking 5' to 3' exonuclease activity, Genbank Accession No.: AR053713 (SEQ ID NO: 20).

FIG. 10 provides the amino acid sequence (SEQ ID NO: 21, Genbank Accession No. AAE15301) encoded by SEQ ID NO: 20.

DEFINITIONS

To facilitate understanding of the invention, a number of terms are defined below.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside", as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product. The wild-type form of the coding region for the Tvu DNA polymerase is shown in SEQ ID NO: 1; the wild-type form of the Tvu DNA polymerase protein is shown in SEQ ID NO: 2. Tvu DNA polymerase proteins encoded by "mutant" genes are referred to as "variant" Tvu DNA polymerases. Tvu DNA polymerase proteins encoded by "modified" or "mutant" genes are referred to as "non-naturally occurring" or "variant" Tvu DNA polymerases. Tvu DNA polymerase proteins encoded by the wild-type Tvu DNA polymerase gene (i.e., SEQ ID NO:1) are referred to as "naturally occurring" Tvu DNA polymerases.

As used herein, the term "sample template" refers to a nucleic acid originating from a sample which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "primer" refers to an oligonucleotide, whether occurring naturally (e.g., as in a purified restriction digest) or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

A primer is said to be "capable of hybridizing to a DNA molecule" if that primer is capable of annealing to the DNA molecule; that is the primer shares a degree of complementarity with the DNA molecule. The degree of complementarity can be, but need not be, complete (i.e., the primer need not be 100% complementary to the DNA molecule). Indeed, when mutagenic PCR is to be conducted, the primer will contain at least one mismatched base which cannot hybridize to the DNA molecule. Any primer which can anneal to and support primer extension along a template DNA molecule under the reaction conditions employed is capable of hybridizing to a DNA molecule.

As used herein, the terms "complementary" or "complementarity" are used in reference to a sequence of nucleotides related by the base-pairing rules. For example, for the sequence 5' "A-G-T" 3', is complementary to the sequence 3' "T-C-A" 5'. Complementarity may be "partial," in which only some of the nucleic acids' bases are matched according to the base acids. The degree of complementarity between nucleic acid strands has significant effects on pairing rules. Or, there may be "complete" or "total" complementarity between the nucleic the efficiency and strength of hybridization between nucleic acid strands. This is of particular importance in amplification reactions, as well as detection methods which depend upon hybridization of nucleic acids.

As used herein, the term "probe" refers to an oligonucleotide (i.e., a sequence of nucleotides), whether occurring naturally (e.g., as in a purified restriction digest) or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. In addition to probes, primers and deoxynucleoside triphosphates may contain labels; these labels may comprise, but are not limited to, $^{32}P$, $^{33}P$, $^{35}S$, enzymes, or fluorescent molecules (e.g., fluorescent dyes).

As used herein, the term "target," when used in reference to the polymerase chain reaction, refers to the region of nucleic acid of interest bounded by the primers. In PCR, this is the region amplified and/or identified. Thus, the "target" is sought to be isolated from other nucleic acid sequences. A "segment" is defined as a region of nucleic acid within the target sequence.

As used herein, the term "polymerase chain reaction" ("PCR") refers to the method described in U.S. Pat. Nos. 4,683,195, 4,889,818, and 4,683,202, all of which are hereby incorporated by reference. These patents describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase (e.g., Taq). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (i.e., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the terms "PCR product" and "PCR fragment" refer to the resultant mixture of compounds after two or more cycles of the PCR steps of denaturation, annealing and extension are complete. These terms encompass the case where there has been amplification of one or more segments of one or more target sequences.

A DNA polymerase is said herein to be "derived from the eubacterium *T. vulgaris*" if that polymerase comprises all or a portion of the amino acid sequence of the Tvu DNA polymerase of SEQ ID NO: 2 and maintains DNA synthesis activity. DNA polymerases derived from *T. vulgaris* include the native Tvu DNA polymerase isolated from *T. vulgaris* cells, as well as recombinant Tvu DNA polymerases encoded by the wild-type Tvu DNA polymerase gene (SEQ ID NO: 1) or mutant or variants thereof which maintain DNA synthesis activity (including those containing amino acid analogs).

The term "full-length thermostable Tvu DNA polymerase" as used herein, refers to a DNA polymerase that encompasses essentially every amino acid encoded by the Tvu DNA polymerase gene (SEQ ID NO: 1). One skilled in the art knows there are subtle modifications of some proteins in living cells so that the protein is actually a group of closely related proteins with slight alterations. For example, some but not all proteins: a) have amino acids removed from the amino-terminus; and/or b) have added chemical groups (e.g., glycosylation groups). These modifications may result in molecular weight increase or decrease. These types of modifications are typically heterogenous. Thus, not all modifications occur in every molecule. Thus, the natural "full-length" molecule may actually be a family of molecules that start from the same amino acid sequence but have small differences in their modifications. The term "full-length thermostable Tvu DNA polymerase" encompasses such a family of molecules. The Tvu DNA polymerase gene encodes a protein of 876 amino acids having a predicted molecular weight of 96.3 kilodaltons (kD). As shown in the examples below, the full-length polymerase migrates with an apparent molecular weight of about 97 kD on a 4-20% gradient Tris-glycine PAGE.

The term "high fidelity polymerase" refers to DNA polymerases with error rates of $5 \times 10^{-6}$ per base pair or lower. Examples of high fidelity DNA polymerases include the Tli DNA polymerase derived from *Thermococcus litoralis* (Promega, NEB), Pfu DNA polymerase derived from *Pyrococcus furiosus* (Stratagene), and Pwo DNA polymerase derived from *Pyrococcus woesii* (BM). The error rate of a DNA polymerase may be measured using assays known to the art.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein. The term "rTvu" is used to designate a recombinant form of Tvu polymerase. The term "nTvu" is used to designate the native form of Tvu polymerase. Tvu polymerase encompasses both nTvu and rTvu polymerase.

As used herein in reference to an amino acid sequence or a protein, the term "portion" (as in "a portion of an amino acid sequence") refers to fragments of that protein. The fragments may range in size from four amino acid residues to the entire amino acid sequence minus one amino acid. When used in relation to Tvu polymerases, the fragments may range in size from greater than or equal to about 300 amino acid residues, more preferably greater than or equal to about 400 amino acid residues, most preferably greater to or equal to about 500 amino acids to the entire amino acid sequence minus one amino acid. Particularly preferred fragments of Tvu polymerases retain one or more of the enzymatic activities associated with the wild-type Tvu polymerase (i.e., 5' exonuclease, 3' exonuclease and polymerization activity)

As used herein, the term "fusion protein" refers to a chimeric protein containing the protein of interest (e.g., Tvu DNA polymerases and fragments thereof) joined to an exogenous protein fragment (e.g., the fusion partner which consists of a non-Tvu polymerase protein). The fusion partner may enhance the solubility of Tvu polymerase protein as expressed in a host cell, may provide an affinity tag to allow purification of the recombinant fusion protein from the host cell or culture supernatant, or both. If desired, the fusion protein may be removed from the protein of interest (e.g., Tvu DNA polymerase or fragments thereof) by a variety of enzymatic or chemical means know to the art.

The term "5' to 3' exonuclease activity" refers to the presence of an activity in a protein that is capable of removing nucleotides from the 5' end of an oligonucleotide. 5' to 3' exonuclease activity may be measured using any of the assays provided herein or known in the art. The term "substantially free of 5' to 3' exonuclease activity" indicates that the protein has less than about 5% of the 5' to 3' exonuclease activity of wild-type Tvu, preferably less than about 3% of the 5' to 3' exonuclease activity of wild-type Tvu, and most preferably no detectable 5' to 3' exonuclease activity.

The term "3' to 5' exonuclease activity" refers to the presence of an activity in a protein that is capable of removing nucleotides from the 3' end of an oligonucleotide. The 3' to 5' exonuclease activity may be measured using any of the assays provided herein or known in the art. The term "substantially free of 3' to 5' exonuclease activity" indicates that the protein has less than about 5% of the 3' to 5' exonuclease activity of wild-type Tvu, preferably less than about 3% of the 3' to 5' exonuclease activity of wild-type Tvu, and most preferably no detectable 3' to 5' exonuclease activity.

The terms "DNA polymerase activity," "synthesis activity" and "polymerase activity" are used interchangeably and refer to the ability of a DNA polymerase to synthesize new DNA strands by the incorporation of deoxynucleoside triphosphates. The examples below provide assays for the measurement of DNA polymerase activity, although a number of such assays are known in the art. A protein capable of directing the synthesis of new DNA strands by the incorporation of deoxynucleoside triphosphates in a template-dependent manner is said to be "capable of DNA synthesis activity."

The term "reduced levels of 5' to 3' exonuclease" is used in reference to the level of 5' to 3' exonuclease activity displayed by the wild-type Tvu DNA polymerase (i.e., the polymerase of SEQ ID NO:2) and indicates that the mutant polymerase exhibits lower levels of 5' to 3' exonuclease than does the full-length or unmodified enzyme, preferably less than about 3% of the 5' to 3' exonuclease activity of the full-length or unmodified enzyme, and most preferably no detectable 5' to 3' exonuclease activity.

A polymerase which "lacks significant 5' to 3' exonuclease" is a polymerase which exhibits less than about 5% of the 5' to 3' exonuclease activity of wild-type polymerases, preferably less than about 3% of the 5' to 3' exonuclease activity of the wild-type enzyme, and most preferably no detectable 5' to 3' exonuclease activity.

The term "reverse transcriptase activity" and "reverse transcription" refers to the ability of an enzyme to synthesize a DNA strand (i.e., complementary DNA, cDNA) utilizing an RNA strand as a template. The term "substantially manganese ion independent," when used in reference to reverse transcriptase activity, refers to reverse transcriptase activity in a reaction mix that contains a low proportion (i.e., less than about 5% of the concentration) of manganese compared to magnesium.

The terms "cell," "cell line," "host cell," as used herein, are used interchangeably, and all such designations include progeny or potential progeny of these designations. The words "transformants" or "transformed cells" include the primary transformed cells derived from that cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The present invention provides Tvu polymerases expressed in either prokaryotic or eukaryotic host cells. Nucleic acid encoding the Tvu polymerase may be introduced into bacterial host cells by a number of means including transformation of bacterial cells made competent for transformation by treatment with calcium chloride or by electroporation. In embodiments in which Tvu polymerases are to be expressed in the host cells, nucleic acid encoding the Tvu polymerase may be introduced into eukaryotic host cells by any suitable means, including calcium phosphate co-precipitation, spheroplast fusion, electroporation and the like. When the eukaryotic host cell is a yeast cell, transformation may be accomplished by such methods as treatment of the host cells with lithium acetate or by electroporation.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Nucleic acids are known to contain different types of mutations. A "point" mutation refers to an alteration in the sequence of a nucleotide at a single base position from the wild type sequence. Mutations may also refer to insertion or deletion of one or more bases, so that the nucleic acid sequence differs from the wild-type sequence.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity). In this case, in the absence of non-specific binding, the probe will not hybridize to the second non-complementary target.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989. *Nucleic Acid Hybridization, A Practical Approach*, IRL Press, Washington D.C., 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

As used herein, the term "$T_m$" is used in reference to the "melting temperature". The melting temperature is the temperature at which 50% of a population of double-stranded nucleic acid molecules becomes dissociated into single strands. The equation for calculating the Tm of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C.+(number of G+C)×4° C.]. (C. R. Newton et al., *PCR*, 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m=81.5+0.41(\% G+C)$, when a nucleic acid is in aqueous solution at 1 M NaCl. (e.g., Anderson and Young, Quantitative Filter Hybridization, in *Nucleic Acid Hybridization*, 1985). Other more sophisticated computations exist in the art which take structural as well as sequence characteristics into account for the calculation of $T_m$. A calculated $T_m$ is merely an estimate; the optimum temperature is commonly determined empirically.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs which encode a multitude of proteins. However, isolated nucleic acid encoding a Tvu polymerase includes, by way of example, such nucleic acid in cells ordinarily expressing a Tvu polymerase where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and anti-sense strands (i.e., the oligonucleotide may be double-stranded).

As used herein, the term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional protein is produced.

As used herein, the term "promoter" means a recognition site on a DNA sequence or group of DNA sequences that provide an expression control element for a gene and to which RNA polymerase specifically binds and initiates RNA synthesis (transcription) of that gene.

As used herein, the term "recombinant DNA molecule" means a hybrid DNA sequence comprising at least two nucleotide sequences not normally found together in nature.

As used herein, the term "vector" is used in reference to nucleic acid molecules that transfer DNA segment(s) from one cell to another and capable of replication in a cell. Vectors may include plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in host cells and possibly other sequences, e.g. an optional operator sequence. A promoter is defined as a DNA sequence that directs RNA polymerase to bind to DNA and to initiate RNA synthesis. Eukaryotic expression vectors include a promoter, polyadenlyation signal and optionally an enhancer sequence.

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the term "a polynucleotide having a nucleotide sequence encoding a gene," means a nucleic acid sequence comprising the coding region of a gene, or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987). For example, the SV40 early gene enhancer is very active in a wide variety of cell types from many mammalian species and has been widely used for the expression of proteins in mammalian cells (Dijkema et al., EMBO J. 4:761, 1985). Two other examples of promoter/enhancer elements active in a broad range of mammalian cell types are those from the human elongation factor 1α gene (Uetsuki et al., J. Biol. Chem., 264:5791, 1989; Kim, et al., Gene 91:217, 1990; and Mizushima and Nagata, Nuc. Acids. Res., 18:5322, 1990) and the long terminal repeats of the Rous sarcoma virus (Gorman et al., Proc. Natl. Acad. Sci. USA 79:6777, 1982); and the human cytomegalovirus (Boshart, et al., Cell 41:521, 1985).

As used herein, the term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York, 1989, pp. 16.7-

16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (~100 copies/cell).

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules. A molecule that catalyzes chemical and biological reactions is referred to as "having enzyme activity" or "having catalytic activity."

As used herein, the term "polymerase" refers to an enzyme that synthesizes nucleic acid strands (e.g., RNA or DNA) from ribonucleoside triphosphates to deoxyribonucleoside triphosphates.

As used herein, the term "polymerase activity" refers to the ability of an enzyme to synthesize nucleic acid stands (e.g., RNA or DNA) from ribonucleoside triphosphates or deoxynucleoside triphosphates. DNA polymerases synthesize DNA, while RNA polymerases synthesize RNA.

As used herein, the term "surfactant" refers to any molecule having both a polar head group, that energetically prefers solvation by water, and a hydrophobic tail that is not well solvated by water. The term "cationic surfactant" refers to a surfactant with a cationic head group. The term "anionic surfactant" refers to a surfactant with an anionic head group.

As used herein, the terms "buffer" or "buffering agents" refer to materials that when added to a solution, cause the solution to resist changes in pH.

As used herein, the terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

As used herein, the term "divalent salt" refers to any salt in which a metal (e.g., Mg, Ca, or Sr) has a net 2+ charge in solution.

As used herein, the terms "chelator" or "chelating agent" refer to any materials having more than one atom with a lone pair of electrons that are available to bond to a metal ion.

As used herein, the term "solution" refers to an aqueous or non-aqueous mixture.

As used herein, the term "buffering solution" refers to a solution containing a buffering reagent.

As used herein, the term "reaction buffer" refers to a buffering solution in which an enzymatic reaction is performed.

As used herein, the term "storage buffer" refers to a buffering solution in which an enzyme is stored.

As used herein, the phrase "substantially free of manganese ions" refers to a solution that is characterized by absence of more than trace amounts of manganese. In functional terms, a solution that is "substantially free of manganese ions" can contain small or trace amounts of manganese ions so that the fidelity of DNA polymerases known to be sensitive to manganese (e.g., Taq DNA polymerase) is not decreased (e.g., the fidelity is the same as compared to the fidelity of the DNA polymerase in a solution completely free of manganese).

All amino acid residues identified herein are in the natural L-configuration. In keeping with standard polypeptide nomenclature, J. Biol. Chem., 243:3557-3559, 1969, abbreviations for amino acid residues are as shown in the following Table of Correspondence.

| TABLE OF CORRESPONDENCE | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

DESCRIPTION OF THE INVENTION

The present invention relates to reverse transcription of RNA templates, and in particular to reverse transcription by thermostable DNA polymerases. Extensive research has been conducted on the isolation of DNA polymerases from mesophilic organisms such as *E. coli*. (e.g., Bessman et al., J. Biol. Chem. 223:171, 1957; Buttin and Kornberg, J. Biol. Chem. 241:5419, 1966; and Joyce and Steitz, Trends Biochem. Sci., 12:288-292, 1987). Other mesophilic polymerases have also been studied, including, but not limited to *Bacillus licheniformis* (Stenesh and McGowan, Biochim. Biophys. Acta 475: 32-44, 1977; and Stenesh and Roe, Biochim. Biophys. Acta 272:156-166, 1972); *Bacillus subtilis* (Low et al., J. Biol. Chem., 251:1311, 1976; and Ott et al., J. Bacteriol., 165:951, 1986); *Salmonella typhimurium* (Harwood et al., J. Biol. Chem., 245:5614, 1970; and Hamilton and Grossman, Biochem., 13:1885, 1974), *Streptococcus pneumoniae* (Lopez et al., J. Biol. Chem., 264:4255, 1989); and *Micrococcus luteus* (Engler and Bessman, Cold Spring Harbor Symp., 43:929, 1979).

Somewhat less investigation has been made on the isolation and purification of DNA polymerases from thermophilic organisms. However, native (i.e, non-recombinant) and/or recombinant thermostable DNA polymerases have been purified from various organisms, as shown in Table 1 below. In addition to native forms, modified forms of thermostable DNA polymerases having reduced or absent 5' to 3' exonuclease activity have been expressed and purified from *Thermus aquaticus, T. maritima, Thermus* species sps17, *Thermus* species Z05, *T. thermophilus, B. stearothermophilus* (U.S. Pat. Nos. 5,747,298, 5,834,253, 5,874,282, and 5,830,714) and *T. africanus* (WO 92/06200).

Reverse transcription from many RNA templates by commonly used reverse transcriptases such as avian myeloblastosis virus (AMV) reverse transcriptase and Moloney murine leukemia virus (MMLV) reverse transcriptase is often limited by the secondary structure of the RNA template. Secondary structure in RNA results from hybridization between complementary regions within a given RNA molecule. Secondary structure causes poor synthesis of cDNA and premature termination of cDNA products because polymerases are unable to process through the secondary structure. Therefore, RNAs with secondary structure may be poorly represented in a cDNA library and detection of the presence of RNA with secondary structure in a sample by RT-PCR may be difficult. Furthermore, secondary structure in RNA may cause inconsistent results in techniques such as differential display PCR. Accordingly, it is advantageous to conduct reverse transcription reactions at increased temperatures so that secondary structure is removed or limited.

Several thermostable DNA polymerases (e.g., *T. thermophilus* DNA polymerase, *T. aquaticus* DNA polymerase [e.g., U.S. Pat. No. 5,322,170], and *A. thermophilum* DNA polymerase [e.g., WO 98/14588]) have been demonstrated to possess reverse transcriptase activity (See Table 1 for a listing of thermostable DNA polymerases).

TABLE 1

Polymerases Isolated From Thermophilic Organisms

| Organism | Citation |
| --- | --- |
| *Thermus aquaticus* | Kaledin et al., Biochem., 45: 494-501 (1980); Biokhimiya 45: 644-651 (1980). |
| | Chien et al., J. Bacteriol., 127: 1550 (1976). |
| | University of Cincinnati Master's thesis by A. Chien, "Purification and Characterization of DNA Polymerase from *Thermus aquaticus*," (1976). |
| | University of Cincinnati, Master's thesis by D. B. Edgar, "DNA Polymerase From an Extreme Thermophile: *Thermus aquaticus*," (1974). |
| | U.S. Pat. No. 4,889,818* |
| | U.S. Pat. No. 5,352,600* |
| | U.S. Pat. No. 5,079,352* |
| | European Patent Pub. No. 258,017* |
| | PCT Pub. No. WO 94/26766* |
| | PCT Pub. No. WO 92/06188* |
| | PCT Pub. No. WO 89/06691* |
| *Thermatoga maritima* | PCT Pub. No. WO 92/03556* |
| *Thermatoga neapolitana* | U.S. Pat. No. 5,912,155* |
| | U.S. Pat. No. 5,939,301* |
| | U.S. Pat. No. 6,001,645* |
| *Thermotoga* strain FjSS3-B.1 | Simpson et al., Biochem. Cell Biol., 68: 1292-1296 (1990). |
| *Thermosipho africanus* | PCT Pub. No. 92/06200* |
| | U.S. Pat. No. 5,968,799* |
| *Thermus thermophilus* | Myers and Gelfand, Biochem., 30: 7661 (1991). |
| | PCT Pub. No. WO 91/09950* |
| | PCT Pub. No. WO 91/09944* |
| | Bechtereva et al., Nucleic Acids Res., 17: 10507 (1989). |
| | Glukhov et al., Mol. Cell. Probes 4: 435-443 (1990). |
| | Carballeira et al., BioTech., 9: 276-281 (1990). |
| | Ruttiman et al., Eur. J. Biochem., 149: 41-46 (1985). |
| | Oshima et al., J. Biochem., 75: 179-183 (1974). |
| | Sakaguchi and Yajima, Fed. Proc., 33: 1492 (1974) (abstract). |
| *Thermus flavus* | Kaledin et al., Biochem., 46: 1247-1254 (1981); Biokhimiya 46: 1576-1584 (1981). |
| | PCT Pub. No. WO 94/26766* |
| *Thermus ruber* | Kaledin et al., Biochem., 47: 1515-1521 (1982); Biokhimiya 47: 1785-1791 (1982). |
| *Thermoplasma acidophilum* | Hamal et al., Eur. J. Biochem., 190: 517-521 (1990). |
| | Forterre et al., Can. J. Microbiol., 35: 228-233 (1989). |
| *Sulfolobus acidocaldarius* | Salhi et al., J. Mol. Biol., 209: 635-641 (1989). |
| | Salhi et al., Biochem. Biophys. Res. Comm., 167: 1341-1347 (1990). |
| | Rella et al., Ital. J. Biochem., 39: 83-99 (1990). |
| | Forterre et al., Can. J. Microbiol., 35: 228-233 (1989). |
| | Rossi et al., System. Appl. Microbiol., 7: 337-341 (1986). |
| | Klimczak et al., Nucleic Acids Res., 13: 5269-5282 (1985). |
| | Elie et al., Biochim. Biophys. Acta 951: 261-267 (1988). |
| *Bacillus caldotenax* | J. Biochem., 113: 401-410 (1993). |
| *Bacillus stearothermophilus* | Sellmann et al., J. Bacteriol., 174: 4350-4355 (1992). |
| | Stenesh and McGowan, Biochim. Biophys. Acta 475: 32-44 (1977). |
| | Stenesh and Roe, Biochim. Biophys. Acta 272: 156-166 (1972). |
| | Kaboev et al., J. Bacteriol., 145: 21-26 (1981). |

TABLE 1-continued

Polymerases Isolated From Thermophilic Organisms

| Organism | Citation |
| --- | --- |
| Methanobacterium thermoautotropicum | Klimczak et al., Biochem., 25: 4850-4855 (1986). |
| Thermococcus litoralis | Kong et al., J. Biol. Chem. 268: 1965 (1993) <br> U.S. Pat. No. 5,210,036* <br> U.S. Pat. No. 5,322,785* |
| Anaerocellum thermophilus | Ankenbauer et al., WO 98/14588* |
| Pyrococcus sp. KOD1 | U.S. Pat. No. 6,008,025* |
| Pyrococcus furiosus | Lundberg et al., Gene 108: 1 (1991) <br> PCT Pub. WO 92/09689* <br> U.S. Pat. No. 5,948,663* <br> U.S. Pat. No. 5,866,395* |

*Herein incorporated by reference.

These enzymes can be used at higher temperatures than retroviral reverse transcriptases so that much of the secondary structure of RNA molecules is removed. However, the reverse transcriptase activity of many of these polymerases is only observed in the presence of manganese ions. Reverse transcription reactions conducted in the presence of manganese are often suboptimal because the presence of manganese ions lowers the fidelity of the polymerase and can cause damage to polynucleotides. To date, only a small subset of thermostable DNA polymerases and mixtures have been shown to have reverse transcriptase activity in the presence of magnesium ions: A. thermophilum DNA polymerase (e.g., WO 98/14588, incorporated herein by reference); B. caldotenax DNA polymerase (e.g., U.S. Pat. No. 5,436,149, incorporated herein by reference); and the polymerase mixture marketed as C. THERM (Boehringer Mannheim).

In the present invention, thermostable stable polymerases were screened for their ability to reverse transcribe a RNA template in the presence of magnesium ions. While more than ten polymerases were screened, only three (i.e., T. vulgaris, B. stearothermophilus, and A. thermophilum DNA polymerases) demonstrated reverse transcriptase activity in the presence of magnesium ions. Under the conditions utilized herein, Tvu and Bst DNA polymerases demonstrated greater than 50-fold higher reverse transcriptase activity in the presence of $Mg^{2+}$ than native Taq DNA polymerase, sequencing-grade Taq DNA polymerase, Tth DNA polymerase, and Tne DNA polymerase.

Reverse transcription of a RNA template into cDNA is an integral part of many techniques used in molecular biology. Accordingly, the reverse transcription procedures, mixtures, and kits provided in the present invention find a wide variety of uses. For example, it is contemplated that the reverse transcription procedures and compositions of the present invention are utilized to produce cDNA inserts for cloning into cDNA library vectors (e.g., lambda gt10 [Huynh et al., In DNA Cloning Techniques: A Practical Approach, D. Glover, ed., IRL Press, Oxford, 49, 1985], lambda gt11 [Young and Davis, Proc. Nat'l. Acad. Sci., 80:1194, 1983], pBR322 [Watson, Gene 70:399-403, 1988], pUC19 [Yarnisch-Perron et al., Gene 33:103-119, 1985], and M13 [Messing et al., Nucl. Acids. Res. 9:309-321, 1981]). The present invention also finds use for identification of target RNAs in a sample via RT-PCR (e.g., U.S. Pat. No. 5,322,770, incorporated herein by reference). Additionally, the present invention finds use in providing cDNA templates for techniques such as differential display PCR (e.g., Liang and Pardee, Science 257(5072):967-71 (1992).

The following description of the invention is divided into: I. Thermostable DNA Polymerase Compositions; II. Use of Thermostable DNA Polymerases for Reverse Transcription; III. Use of Thermostable DNA polymerases for RT-PCR; and IV. Kits for Reverse Transcription.

I. Thermostable DNA Polymerase Compositions

In some embodiments of the present invention, compositions for performing reverse transcription and RT-PCR are provided. Those skilled in the art will recognize that the concentrations or amounts of many of these components is varied for particular circumstances. For example, the optimum primer and divalent salt concentrations are known to vary for different primers or primer pairs. Therefore, the concentrations and amounts of composition components listed below are meant to serve as guide to those skilled in the art, and are not intended to limit the scope of the invention.

A. DNA Polymerases

In some embodiments, the compositions include a thermostable DNA polymerase (e.g., Tvu DNA polymerase or Bst DNA polymerase (New England Biolabs, Beverley, Mass.). In some embodiments, the Tvu DNA polymerase is encoded by an amino acid sequence selected from SEQ ID NOs: 2, 4, and 6. In other embodiments, the Bst DNA polymerase is encoded by SEQ ID NO: 19. In other embodiments, the Bst DNA polymerase has reduced 5' or 3' exonuclease activity (SEQ ID NOs. 20 and 21; e.g., U.S. Pat. Nos. 5,747,298, 5,834,253, 5,874,282, and 5,830,714, incorporated herein by reference).

The present invention provides wild-type and mutant forms of Tvu DNA polymerases. In preferred embodiments, the mutant forms are substantially free of 5' to 3' exonuclease activity. Without being limited to any particular mutant, representative examples of mutant Tvu DNA polymerases are provided herein. M285 (SEQ ID NO: 4) begins at the methionine codon located at residue 285 of the wild type Tvu DNA polymerase and ends at the wild type termination codon. M285 is encoded by the nucleic acid sequence of SEQ ID NO: 3. T289M (SEQ ID NO: 6) begins at residue 289 of the wild type Tvu DNA polymerase which was mutated from a threonine to a methionine and ends at the wild type termination codon. T289M is encoded by the nucleic acid sequence of SEQ ID NO: 5. The modified Tvu polymerases of the present invention are advantageous in situations where the polymerization (i.e., synthetic) activity of the enzyme is desired but the presence of 5' to 3' exonuclease activity is not.

The present invention is not intended to be limited by the nature of the alteration (e.g., deletion, insertion, substitution) necessary to render the Tvu polymerase deficient in 5' to 3' exonuclease activity. Indeed, the present invention contemplates a variety of methods, including but not limited to proteolysis and genetic manipulation.

The present invention provides nucleic acids encoding Tvu DNA polymerase I (SEQ ID NO: 1). Other embodiments of the present invention provide polynucleotide sequences that are capable of hybridizing to SEQ ID NO: 1 under conditions of high stringency. In some embodiments, the hybridizing polynucleotide sequence encodes a protein that retains at least one biological activity of the naturally occurring Tvu DNA polymerase. In preferred embodiments, hybridization conditions are based on the melting temperature ($T_m$) of the nucleic acid binding complex and confer a defined "stringency" as explained above (e.g., Wahl, et al., Methods Enzymol., 152:399-407, 1987, incorporated herein by reference).

In other embodiments of the present invention, variants of Tvu DNA polymerase are provided (e.g. SEQ ID NOs: 3 and 5). In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

In still other embodiments, the nucleotide sequences of the present invention may be engineered in order to alter a Tvu DNA polymerase coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

In other embodiments, the present invention provides Tvu DNA polymerase polypeptide (e.g., SEQ ID NO: 2). Other embodiments of the present invention provide fragments, fusion proteins or functional equivalents of Tvu DNA polymerase (e.g., SEQ ID NOs: 4, 6). In still other embodiments of the present invention, nucleic acid sequences corresponding to Tvu DNA polymerase may be used to generate recombinant DNA molecules that direct the expression of Tvu DNA polymerase and variants in appropriate host cells. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host cell (e.g., by bacterial cells in culture). In other embodiments, the polypeptides of the invention may also include an initial methionine amino acid residue.

In one embodiment of the present invention, due to the inherent degeneracy of the genetic code, DNA sequences other than SEQ ID NO: 1 encoding substantially the same or a functionally equivalent amino acid sequence, may be used to clone and express Tvu DNA polymerase. In general, such polynucleotide sequences hybridize to SEQ ID NO: 1 under conditions of medium stringency as described above. As will be understood by those of skill in the art, it may be advantageous to produce Tvu DNA polymerase-encoding nucleotide sequences possessing non-naturally occurring codons. Therefore, in some preferred embodiments, codons preferred by a particular prokaryotic or eukaryotic host (Murray et al., Nuc Acids Res 17, 1989) are selected, for example, to increase the rate of Tvu DNA polymerase expression or to produce recombinant RNA transcripts having desirable properties, such as a longer half-life than transcripts produced from naturally occurring sequence.

1. Vectors for Production of Tvu DNA Polymerase

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1, 3, 5, 18 and 20). In some embodiments of the present invention, the constructs comprise a vector into which a sequence of the invention has been inserted, in a forward or reverse orientation. In still other embodiments, the heterologous structural sequence (e.g., SEQ ID NOs: 1, 3, 5, 18, and 20) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors that are replicable and viable in the host are known to those of skill in the art, and are commercially available. Any plasmid or vector may be used as long as it is replicable and viable in the host. In some preferred embodiments of the present invention, bacterial expression vectors comprise an origin of replication, a suitable promoter and optionally an enhancer, and also any necessary ribosome binding sites, polyadenylation sites, transcriptional termination sequences, and 5' flanking nontranscribed sequences.

In certain embodiments of the present invention, the Tvu DNA sequence in the expression vector is operatively linked to an appropriate expression control sequence(s) (e.g., a constitutive or inducible promoter) to direct mRNA synthesis. Promoters useful in the present invention include, but are not limited to, a retroviral LTR, SV40 promoter, CMV promoter, RSV promoter, E. coli lac or trp promoters, phage lambda $P_L$ and $P_R$ promoters, T3, SP6 and T7 promoters. In other embodiments of the present invention, recombinant expression vectors include origins of replication and selectable markers, (e.g., tetracycline or ampicillin resistance in E. coli, or neomycin phosphotransferase gene for selection in eukaryotic cells).

In other embodiments, the expression vector also contains a ribosome binding site for translation initiation, as well as a transcription terminator. In still other embodiments of the present invention, the vector may also include appropriate sequences for enhancing expression.

2. Host Cells and Systems for Production of Tvu DNA Polymerase

The present invention contemplates that the nucleic acid construct of the present invention be capable of expression in a suitable host. In particular, it is preferable that the expression system chosen utilizes a controlled promoter such that expression of the Tvu polymerase is prevented until expression is induced. In this manner, potential problems of toxicity of the expressed polymerases to the host cells (and particularly to bacterial host cells) are avoided. Those in the art know methods for attaching various promoters and 3' sequences to a gene sequence in order to achieve efficient and tightly controlled expression. The examples below disclose a number of suitable vectors and vector constructs. Of course, there are other suitable promoter/vector combinations. The choice of a particular vector is also a function of the type of host cell to be employed (i.e., prokaryotic or eukaryotic).

In some embodiments of the present invention, the host cell can be a prokaryotic cell (e.g., a bacterial cell). Specific examples of host cells include, but are not limited to, *E. coli, S. typhimurium, B. subtilis*, and various species within the genera *Pseudomonas, Streptomyces*, and *Staphylococcus*.

The constructs in host cells can be used in a conventional manner to produce the gene product encoded by the recombinant sequence. In some embodiments, introduction of the construct into the host cell can be accomplished by any suitable method known in the art (e.g., calcium phosphate transfection, DEAE-Dextran mediated transfection, or electroporation (e.g., Davis et al., *Basic Methods in Molecular Biology*, 1986, for a review). Alternatively, in some embodiments of the present invention, the polypeptides of the invention can be synthetically produced by conventional peptide synthesizers.

In some embodiments of the present invention, following transformation of a suitable host strain and growth of the host strain to an appropriate cell density, the selected promoter is induced by appropriate means (e.g., temperature shift or chemical induction), and the host cells are cultured for an additional period. In other embodiments of the present invention, the host cells are harvested (e.g., by centrifugation), disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega; this cell-free system is described in U.S. Pat. No. 5,324,637, herein incorporated by reference).

3. Purification of Tvu DNA Polymerase

The present invention also provides methods for recovering and purifying Tvu DNA polymerase from native and recombinant cell cultures including, but not limited to, ammonium sulfate precipitation, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed as one or more purification steps. In some embodiments, purification is performed as described in Example 1.

In other embodiments of the present invention, the nucleic acid construct containing DNA encoding the wild-type or a variant Tvu polymerase further comprises the addition of exogenous sequences (i.e., sequences not encoded by the Tvu polymerase coding region) to either the 5' or 3' end of the Tvu polymerase coding region to allow for ease in purification of the resulting polymerase protein (the resulting protein containing such an affinity tag is termed a "fusion protein"). Several commercially available expression vectors are available for attaching affinity tags (e.g., an exogenous sequence) to either the amino or carboxy-termini of a coding region. In general these affinity tags are short stretches of amino acids that do not alter the characteristics of the protein to be expressed (i.e., no change to enzymatic activities results).

For example, the pET expression system (Novagen) utilizes a vector containing the T7 promoter operably linked to a fusion protein with a short stretch of histidine residues at either end of the protein and a host cell that can be induced to express the T7 DNA polymerase (i.e., a DE3 host strain). The production of fusion proteins containing a histidine tract is not limited to the use of a particular expression vector and host strain. Several commercially available expression vectors and host strains can be used to express protein sequences as a fusion protein containing a histidine tract (e.g., the pQE series [pQE-8, 12, 16, 17, 18, 30, 31, 32, 40, 41, 42, 50, 51, 52, 60 and 70] of expression vectors (Qiagen) used with host strains M15[pREP4] [Qiagen] and SG13009[pREP4] [Qiagen]) can be used to express fusion proteins containing six histidine residues at the amino-terminus of the fusion protein). Additional expression systems which utilize other affinity tags are known to the art.

Once a suitable nucleic acid construct has been made, the Tvu DNA polymerase may be produced from the construct. The examples below and standard molecular biological teachings known in the art enable one to manipulate the construct by a variety of suitable methods. Once the desired Tvu polymerase has been expressed, the polymerase may be tested for DNA synthesis as described below.

4. Deletion Mutants of Tvu DNA Polymerase

The present invention further provides fragments of Tvu DNA polymerase (i.e., deletion mutants; e.g., SEQ ID NOs 4 and 6). In some embodiments of the present invention, when expression of a portion of Tvu DNA polymerase is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751-757, 1987) and *S. typhimurium*, and its in vitro activity has been demonstrated on recombinant proteins (Miller et al., Proc. Nat'l. Acad. Sci., 84:2718-1722, 1990). Therefore, removal of an N-terminal methionine, if desired, can be achieved either in vivo by expressing such recombinant polypeptides in a host producing MAP (e.g., *E. coli* or CM89 or *S. cerevisiae*), or in vitro by use of purified MAP.

In other embodiments of the present invention, Tvu DNA polymerases having a reduced level of 5' to 3' exonuclease compared to wild-type were produced by subcloning portions of Tvu DNA polymerase lacking the 5' to 3' exonuclease-encoding domain (Examples 11-12). In other embodiments, proteolysis is used to remove portion of Tvu polymerase responsible for 5' to 3' exonuclease activity. Following proteolytic digestion, the resulting fragments are separated by standard chomatographic techniques and assayed for the ability to synthesize DNA and to act as a 5' to 3' exonuclease.

5. Variants of Tvu DNA Polymerase

Still other embodiments of the present invention provide other mutant or variant forms of Tvu DNA polymerase. It is possible to modify the structure of a peptide having an activity (e.g., DNA synthesis activity) of Tvu DNA polymerase for such purposes as enhancing stability (e.g., in vitro shelf life, and/or resistance to proteolytic degradation in vivo) or reducing 5' to 3' exonuclease activity. Such modified peptides are considered functional equivalents of peptides having an activity of Tvu DNA polymerase as defined herein. A modified peptide can be produced in which the nucleotide sequence encoding the polypeptide has been altered, such as by substitution, deletion, or addition. In some preferred embodiments of the present invention, the alteration decreases the 5' to 3' exonuclease activity to a level low enough to provide an improved enzyme for a variety of applications such as PCR and chain termination sequencing (including thermal cycle sequencing) as discussed in the Examples below. In particularly preferred embodiments, these modifications do not significantly reduce the DNA synthesis activity of the modified enzyme. In other words, construct "X" can be evaluated according to the protocol described below in order to determine whether it is a member of the genus of modified Tvu polymerases of the present invention as defined functionally, rather than structurally.

Moreover, as described above, variant forms of Tvu DNA polymerase are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Tvu DNA polymerase containing conservative replacements. Conservative replacements are those that take place within a family of amino acids that are related in their side chains. Genetically encoded amino acids are can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes, e.g., replacement of a glycine with a tryptophan. Analogous minor variations can also include amino acid deletions or insertions, or both. Guidance in determining which amino acid residues can be substituted, inserted, or deleted without abolishing biological activity can be found using computer programs well known in the art, for example LASERGENE software (DNASTAR Inc., Madison, Wis.).

When a Tvu DNA polymerase enzyme of the present invention has an amino acid residue sequence that is not identical to that of SEQ ID NOs: 2, 4 or 6 because one or more conservative substitutions has been made, it is preferred that no more than 20 percent, and more preferably no more than 10 percent, and most preferably no more than 5 percent of the amino acid residues are substituted as compared to SEQ ID NOs: 2, 4 or 6.

A contemplated Tvu DNA polymerase can also have a length shorter than that of SEQ ID NO: 2 and maintain DNA synthesis activity. For example, the first 284 amino acids at the amino terminus can be deleted as in an enzymes of SEQ ID NO: 4 and 6. Such variants exhibit DNA synthesis activity as discussed elsewhere herein, including DNA synthesis activity at temperatures higher than about 50° C.

This invention further contemplates a method for generating sets of combinatorial mutants of the present Tvu DNA polymerase, as well as deletion mutants, and is especially useful for identifying potential variant sequences (i.e., homologs) with unique DNA synthetic activity. The purpose of screening such combinatorial libraries is to generate, for example, novel Tvu DNA polymerase homologs that possess novel activities.

In some embodiments of the combinatorial mutagenesis approach of the present invention, the amino acid sequences for a population of Tvu DNA polymerase homologs or other related proteins are aligned, preferably to promote the highest homology possible. Such a population of variants can include, for example, DNA polymerase homologs from one or more species, or Tvu DNA polymerase homologs from the same species but which differ due to mutation. Amino acids appearing at each position of the aligned sequences are selected to create a degenerate set of combinatorial sequences.

In a preferred embodiment of the present invention, the combinatorial Tvu DNA polymerase library is produced by way of a degenerate library of genes encoding a library of polypeptides including at least a portion of potential Tvu DNA polymerase-protein sequences. For example, a mixture of synthetic oligonucleotides are enzymatically ligated into gene sequences such that the degenerate set of potential Tvu DNA polymerase sequences are expressible as individual polypeptides, or alternatively, as a set of larger fusion proteins (e.g., for phage display) containing the set of Tvu DNA polymerase sequences therein.

There are many ways in which the library of potential Tvu DNA polymerase homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Tvu DNA polymerase sequences. The synthesis of degenerate oligonucleotides is well known in the art (e.g., Narang, S. A, Tetrahedron 39:3 9, 1983; Itakura et al., Recombinant DNA, Proc 3rd Cleveland Sympos. Macromol., Walton, ed., Elsevier, Amsterdam, pp 273-289, 1981; Itakura et al., Annu. Rev. Biochem. 53:323, 1984; Itakura et al., Science 198: 1056, 1984; and Ike et al., Nucleic Acid Res. 11:477 1983). Such techniques have been employed in the directed evolution of other proteins (e.g. Scott et al., Science 249:386-390, 1980; Roberts et al., Proc. Nat'l. Acad. Sci., 89:2429-2433, 1992; Devlin et al., Science 249: 404-406, 1990; Cwirla et al., Proc. Nat'l. Acad. Sci., 87: 6378-6382, 1990; as well as U.S. Pat. Nos. 5,223,409, 5,198,346, and 5,096,815, each of which is incorporated herein by reference).

A wide range of techniques are known in the art for screening gene products of combinatorial libraries generated by point mutations, and for screening cDNA libraries for gene products having a particular property of interest. Such techniques are generally adaptable for rapid screening of gene libraries generated by the combinatorial mutagenesis of Tvu DNA polymerase homologs. The most widely used techniques for screening large gene libraries typically comprise cloning the gene library into replicable expression vectors, transforming appropriate cells with the resulting library of vectors, and expressing the combinatorial genes under conditions such that detection of a desired activity facilitates relatively easy isolation of the vector encoding the gene whose product was detected. The illustrative assays described below are amenable to high through-put analysis as necessary to screen large numbers of degenerate sequences created by combinatorial mutagenesis techniques.

In some embodiments of the present invention, the gene library is expressed as a fusion protein on the surface of a viral particle. For example, foreign peptide sequences can be expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of viral replication. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (e.g., WO 90/02909; WO 92/09690; Marks et al., J. Biol. Chem., 267:16007-16010, 1992; Griffths et al., EMBO J., 12:725-734, 1993; Clackson et al., Nature, 352:624-628, 1991; and Barbas et al., Proc. Nat'l. Acad. Sci., 89:4457-4461, 1992).

In another embodiment of the present invention, the recombinant phage antibody system (e.g., RPAS, Pharmacia Catalog number 27-9400-01) is modified for use in expressing and screening Tvu polymerase combinatorial libraries. The pCANTAB 5 phagemid of the RPAS kit contains the gene encoding the phage gIII coat protein. In some embodiments of the present invention, the Tvu polymerase combinatorial gene library is cloned into the phagemid adjacent to the gIII signal sequence such that it will be expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate Tvu polymerase gene insert. The resulting recombinant phage contain phagemid DNA encoding a specific candidate Tvu polymerase-protein and display one or more copies of the corresponding fusion coat protein. In some embodiments of the present invention, the phage-displayed candidate proteins that are capable of, for example, binding nucleotides or nucleic acids, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning greatly enriches for Tvu polymerase homologs, which are then screened for further biological activities.

In light of the present disclosure, other forms of mutagenesis generally applicable will be apparent to those skilled in the art in addition to the aforementioned rational mutagenesis based on conserved versus non-conserved residues. For example, Tvu DNA polymerase homologs can be generated and screened using, for example, alanine scanning mutagenesis and the like (Ruf et al., Biochem., 33:1565-1572, 1994; Wang et al., J. Biol. Chem., 269:3095-3099, 1994; Balint et al. Gene 137:109-118, 1993; Grodberg et al., Eur. J. Biochem., 218:597-601, 1993; Nagashima et al., J. Biol. Chem., 268:2888-2892, 1993; Lowman et al., Biochem., 30:10832-10838, 1991; and Cunningham et al., Science, 244:1081-1085, 1989); linker scanning mutagenesis (Gustin et al., Virol., 193:653-660, 1993; Brown et al., Mol. Cell. Biol., 12:2644-2652, 1992; McKnight et al., Science, 232:316); or saturation mutagenesis (Meyers et al., Science, 232:613, 1986).

In some embodiments, the wild-type Tvu polymerase is cloned by isolating genomic DNA using molecular biological methods. The isolated genomic DNA is then cleaved into fragments (e.g., about 3 kb or larger) using restriction enzymes and the fragments are inserted into a suitable cloning vector such as a plasmid or bacteriophage vector. The vectors containing fragments of *T. vulgaris* genomic DNA are then transformed into a suitable *E. coli* host. Clones containing DNA encoding the Tvu polymerase may be isolated using functional assays (e.g., presence of thermostable polymerase in lysates of transformed cells) or by hybridization using a probe derived from a region of conservation among DNA polymerases derived from thermostable organisms. Alternatively, the *T. vulgaris* genomic DNA may be used as the target in PCR with primers selected from regions of high sequence conservation among the genes encoding thermostable DNA polymerases. Although such a PCR may not amplify the entire coding region of the Tvu polymerase I gene, the full-length Tvu gene can be isolated by using the amplified fragment as a probe to screen a genomic library containing *T. vulgaris* DNA.

Once the full-length Tvu polymerase gene is obtained, the region encoding the 5' to 3' exonuclease may be altered by a variety of means to reduce or eliminate these activities. Suitable deletion and site-directed mutagenesis procedures are known in the art.

In some embodiments of the present invention, deletion of amino acids from the protein is accomplished either by deletion in the encoding genetic material, or by introduction of a translational stop codon by mutation or frame shift. In other embodiments, proteolytic treatment of the protein molecule is performed to remove portions of the protein. In still further embodiments, deletion mutants are constructed by restriction digesting the wild-type sequence and introducing a new start site by annealing an appropriately designed oligomer to the digested fragment encoding the desired activity (e.g., Example 11).

6. Chemical Synthesis of Tvu DNA Polymerase

In an alternate embodiment of the invention, the coding sequence of Tvu DNA polymerase is synthesized, whole or in part, using chemical methods well known in the art (e.g., Caruthers et al., Nuc. Acids Res. Symp. Ser., 7:215-233, 1980; Crea and Horn, Nuc. Acids Res., 9:2331, 1980; Matteucci and Caruthers, Tetrahedron Lett., 21:719, 1980; and Chow and Kempe, Nuc. Acids Res., 9:2807-2817, 1981). In other embodiments of the present invention, the protein itself is produced using chemical methods to synthesize either a full-length Tvu DNA polymerase amino acid sequence or a portion thereof. For example, peptides can be synthesized by solid phase techniques, cleaved from the resin, and purified by preparative high performance liquid chromatography (e.g., Creighton, *Proteins Structures and Molecular Principles*, W H Freeman and Co, New York N.Y. 1983, for a review). In other embodiments of the present invention, the composition of the synthetic peptides is confirmed by amino acid analysis or sequencing (e.g., Creighton, supra).

Direct peptide synthesis can be performed using various solid-phase techniques (Roberge et al., Science 269:202-204, 1995) and automated synthesis may be achieved, for example, using ABI 431A Peptide Synthesizer (Perkin Elmer) in accordance with the instructions provided by the manufacturer. Additionally, the amino acid sequence of Tvu DNA polymerase, or any part thereof, may be altered during direct synthesis and/or combined using chemical methods with other sequences to produce a variant polypeptide.

B. Other Components

The present invention also provides compositions for performing various reactions (e.g., reverse transcription, polymerase chain reaction, sequencing, first strand cDNA synthesis, and second strand cDNA synthesis) with Tvu and Bst polymerases. In other embodiments, the composition further comprises an additional thermostable polymerase (e.g., Taq DNA polymerase, Tne DNA polymerase, Pfu DNA polymerase, and the like). In some embodiments, the compositions include a purified RNA template (e.g., mRNA, rRNA, and mixtures thereof). In other embodiments, the compositions include a buffering agent (e.g., Tris-HCl) at a concentration of about 5 mM to 100 mM, preferably about 10 mM. In further embodiments, the pH of the buffer is from about 6.0 to 10.0, preferably about 7.0 to 9.0. In still further embodiments, the composition includes a monovalent salt (e.g., NaCl or KCl at a concentration of about 10 mM to 100 mM, preferably about 50 mM). In still further embodiments, the composition includes a divalent salt. In some embodiments, the divalent salt is $MgCl_2$ at a concentration of about 0.5 mM to 25 mM, preferably about 1.5 mM to about 10 mM. In other embodiments, the divalent salt is $MnCl_2$ at a concentration of about 0.1 mM to about 10 mM, preferably about 0.6 mM. In still other embodiments, the composition is substantially manganese ion free. In further embodiments, the composition includes deoxynucleotide phosphates (dNTPs) at a concentration of about 0.5 to 5 mM each, preferably about 0.2 mM each. In still further embodiments, the composition includes one or more primers, preferably at a concentration of about 0.1 to 5 µM. In other embodiments, the compositions includes additives that serve to increase the stability of the components of the reaction (e.g., a cationic or non-ionic surfactant) or to increase the efficiency of amplification (e.g., formamide or betaine).

II. Use of Thermostable DNA Polymerases for Reverse Transcription

The present invention contemplates the use of Tvu and Bst DNA polymerase for reverse transcription reactions. Accordingly, in some embodiments of the present invention, thermostable DNA polymerases having reverse transcriptase activity are provided. In some embodiments, the thermostable DNA polymerase is selected from Tvu DNA polymerase and Bst DNA polymerase. In further embodiments, the reverse transcriptase activity is exhibited in the presence of magnesium or manganese ions. In other embodiments, the polymerase exhibits reverse transcriptase activity in the presence of magnesium ions and the substantial absence of manganese ions.

In some embodiments of the present invention, where Tvu polymerase is utilized to reverse transcribe RNA, the reverse transcription reaction is conducted at about 50° C. to 80° C., preferably about 60° C. to 75° C. In embodiments where Bst reverse transcriptase is utilized for reverse transcription, the reaction is conducted at 50° C. to 75° C., preferably at about 60° C. to 70° C.

In still further embodiments, reverse transcription of an RNA molecule by Tvu or Bst DNA polymerase results in the production of a cDNA molecule that is substantially complementary to the RNA molecule. In other embodiments, the Tvu or Bst DNA polymerase then catalyzes the synthesis of a second strand DNA complementary to the cDNA molecule to form a double stranded DNA molecule. In still further embodiments of the present invention, the Tvu polymerase catalyzes the amplification of the double stranded DNA molecule in a PCR as described above. In some embodiments, PCR is conducted in the same reaction mix as the reverse transcriptase reaction (i.e., a single pot reaction is performed). While Tvu DNA polymerase and Bst DNA polymerase are suitable for use in some single pot reactions, the data presented in the Examples indicate that the inclusion of an additional DNA polymerase is preferable for most amplification procedures due to the lower temperature optimums for Tvu DNA polymerase and Bst DNA polymerase than for other polymerases such as Taq, Pfu and the like. Therefore, in some embodiments, the reaction mixture further comprises an additional thermostable polymerase (e.g., Taq DNA polymerase, Tne DNA polymerase, Pfu DNA polymerase, and the like). In other embodiments, PCR is performed in a separate reaction mix on an aliquot removed from the reverse transcription reaction (i.e., a two pot reaction is performed).

III. Use of Thermostable DNA Polymerases for RT-PCR

The DNA polymerases of the present invention are useful for RT-PCR because the reverse transcription reaction may be conducted in a magnesium-containing buffer that is compatible with efficient amplification. The present invention contemplates single-reaction RT-PCR wherein reverse transcription and amplification are performed in a single, continuous procedure. The RT-PCR reactions of the present invention serve as the basis for many techniques, including, but not limited to diagnostic techniques for analyzing mRNA expression, synthesis of cDNA libraries, rapid amplification of cDNA ends (i.e., RACE) and other amplification-based techniques known in the art. Any type of RNA may be reverse transcribed and amplified by the methods and reagents of the present invention, including, but not limited to RNA, rRNA, and mRNA. The RNA may be from any source, including, but not limited to, bacteria, viruses, fungi, protozoa, yeast, plants, animals, blood, tissues, and in vitro synthesized nucleic acids.

The wild-type and modified Tvu and Bst DNA polymerases of the present invention provide suitable enzymes for use in the PCR. The PCR process is described in U.S. Pat. Nos. 4,683,195 and 4,683,202, the disclosures of which are incorporated herein by reference. In some embodiments, at least one specific nucleic acid sequence contained in a nucleic acid or mixture of nucleic acids is amplified to produce double stranded DNA. Primers, template, nucleoside triphosphates, the appropriate buffer and reaction conditions, and polymerase are used in the PCR process, which involves denaturation of target DNA, hybridization of primers and synthesis of complementary strands. The extension product of each primer becomes a template for the production of the desired nucleic acid sequence. If the polymerase employed in the PCR is a thermostable enzyme, then polymerase need not be added after each denaturation step because heat will not destroy the polymerase activity. Use of such enzymes as Tvu or Bst DNA polymerase allows repetitive heating/cooling cycles without the requirement of fresh enzyme at each cooling step. This represents a major advantage over the use of mesophilic enzymes (e.g., Klenow), as fresh enzyme must be added to each individual reaction tube at every cooling step. The use of Taq in PCR is disclosed in U.S. Pat. No. 4,965,188, EP Publ. No. 258,017, and PCT Publ. No. 89/06691, each of which is herein incorporated by reference.

RT-PCR may be divided into two main steps, reverse transcription of RNA to form a cDNA and amplification of the cDNA. In most prior art RT-PCR methods, these two main steps are separate, with one enzyme being used for reverse transcription, and a different DNA polymerase being used for amplification. In most cases, even when the same enzyme is used for reverse transcription and amplification, some purification of the reverse transcription step product was necessary because of the incompatibility of the buffers used for reverse transcription and amplification.

In some embodiments of the present invention, the reverse transcription and amplification steps of RT-PCR are conducted in the same buffer. In further embodiments, reverse transcription of an RNA into a cDNA, second strand synthesis of a copy of the cDNA, and amplification of the cDNA are conducted in a continuous process in the same reaction mix. In some preferred embodiments, the single pot reaction mixture further comprises an additional thermostable polymerase (e.g., Taq DNA polymerase, Tne DNA polymerase, Pfu DNA polymerase, and the like). In some embodiments, the buffer comprises magnesium and/or manganese ions. In other embodiments, the buffer comprises magnesium ions. In other embodiments, the buffer is substantially free of manganese ions. In still other embodiments, the reverse transcription step is performed at an elevated temperature as described above. In some embodiments of the present invention, primers for reverse transcription also serve as primers for amplification. In other embodiments, the primer or primers used for reverse transcription are different than the primers used for amplification. In some embodiments, more than one RNA in a mixture of RNAs may be amplified or detected by RT-PCR. In other embodiments, multiple RNAs in a mixture of RNAs may be amplified in a multiplex procedure (e.g., U.S. Pat. No. 5,843,660, incorporated herein by reference). In still further embodiments of the present invention, the reverse transcription reaction is performed with Tvu or Bst DNA polymerase, while the amplification step is performed with another thermostable DNA polymerase (e.g., Tth DNA polymerase, Taq DNA polymerase, or Tne DNA polymerase). In still other embodiments, the reverse transcription reaction is performed with one enzyme (e.g., MMLV or AMV), while the amplification reaction is performed with Tvu or Bst DNA polymerase.

IV. Kits for Reverse Transcription.

In other embodiments of the present invention, kits are provided for performing reverse transcription. It is contemplated that the kits of the present invention find use for methods including, but not limited to, reverse transcribing template RNA for the construction of cDNA libraries, for the reverse transcription of RNA for differential display PCR, and RT-PCR identification of target RNA in a sample suspected of containing the target RNA. In some embodiments, the reverse transcription kit comprises the essential reagents required for the method of reverse transcription. For example, in some embodiments, the kit includes a vessel containing a polymerase selected from *T. vulgaris* and *B. stearothermophilus* polymerase. In some embodiments, the kit further comprises a container containing an additional thermostable polymerase (e.g., Taq DNA polymerase, Tne DNA polymerase, Pfu DNA polymerase, and the like). In some embodiments, the concentration of polymerase ranges from about 0.1 to 100 u/µl; in other embodiments, the concentration is about 5 u/µl. In some embodiments, kits for reverse transcription also include a vessel containing a reaction buffer. Preferably, these reagents are free of contaminating RNase activity. In other embodiments of the present invention, reaction buffers comprise a buffering reagent in a concentration of about 5 to 15 mM (preferably about 10 mM Tris-HCl at a pH of about 7.5 to 9.0 at 25° C.), a monovalent salt in a concentration of about 20 to 100 mM (preferably about 50 mM NaCl or KCl), a divalent cation in a concentration of about 1.0 to 10.0 mM (preferably MgCl$_2$), dNTPs in a concentration of about 0.05 to 1.0 mM each (preferably about 0.2 mM each), and a surfactant in a concentration of about 0.001 to 1.0% by volume (preferably about 0.01% to 0.1%). In some embodiments, a purified RNA standard set is provided in order to allow quality control and for comparison to experimental samples. In some embodiments, the kit is packaged in a single enclosure including instructions for performing the assay methods (e.g., reverse transcription or RT-PCR). In some embodiments, the reagents are provided in containers and are of a strength suitable for direct use or use after dilution.

EXAMPLES

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); fmol (femtomole); HPLC (high pressure liquid chromatography); DTT (dithiothreitol); DMF (N,N dimethyl formamide); DNA (deoxyribonucleic acid); p (plasmid); µl (microliters); ml (milliliters); µg (micrograms); pmoles (picomoles); mg (milligrams); MOPS (3-[N-Morpholino]propanesulfonic acid); M (molar); mM (milliMolar); µM (microMolar); nm (nanometers); kd (kilodaltons); OD (optical density); EDTA (ethylene diamine tetra-acetic acid); FITC (fluorescein isothiocyanate); SDS (sodium dodecyl sulfate); NaPO$_4$ (sodium phosphate); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); SDS-PAGE (sodium dodecyl sulfate polyacrylamide gel electrophoresis); Tween (polyoxyethylene-sorbitan); Boehringer Mannheim or BM (Boehringer Mannheim, Indianapolis, Ind.); Epicentre (Epicentre Technologies, Madison, Wis.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Promega (Promega Corp., Madison, Wis.); Qiagen (Qiagen Inc., Chatsworth, Calif.); Spectra (Spectra, Houston, Tex.); Stratagene (Stratagene Cloning Systems, La Jolla, Calif.); USB (U.S. Biochemical, Cleveland, Ohio); and Tomah (Tomah Products Inc., Tomah, Wis.).

Example 1

Purification of Tvu DNA Polymerase

This example describes the purification of native *T. vulgaris* (Tvu) DNA polymerase. Tvu cells were obtained from the ATCC (Accession Number 43649). This purified polymerase was then used in the experiments represented in Examples 2 through 10. One milliliter from the frozen seed vial was thawed and inoculated into 1 liter Luria broth. The medium was supplemented with 10 ml of 20% glucose. The culture was grown for 15 hours on a shaker at 55° C. and 250 rpm. Five hundred milliliters of this culture were added to 17.5 liters medium in a 20-liter fermenter. The culture was grown at 55° C. The culture growth was monitored spectrophotometrically at 580 nm and measured based on wet weight of cell pellets from 40 ml of broth. After 4.75 hours, the contents were chilled and harvested using a CEPA tubular bowl centrifuge. The net yield of cell paste was 69.0 g. The cell paste was stored in a freezer at −85° C., until purification of Tvu DNA polymerase was performed.

Thirty grams of cell paste were suspended in ice cold 150 ml 0.25 M NaCl TEDGT buffer (50 mM Tris-HCl at pH 7.3, 1 mM EDTA, 1 mM DTT, 10% Glycerol, and 0.1% Tween 20) containing 2.5 mM PMSF, and lysed by sonication on ice. Then 11.5 ml of 5% PEI was added to the lysate to precipitate the DNA. The following purification steps were performed at 4° C. Centrifugation (15,000 rpm in a Beckman JA18 rotor for 15 minutes) was used to separate the supernatant from the precipitate. The supernatant was then collected, and ammonium sulfate was added to a final saturation of 65% to precipitate the DNA polymerase. Centrifugation (15,000 rpm in a Beckman JA18 rotor for 20 minutes) was used to separate the ammonium sulfate precipitate from the supernatant. The precipitate was collected, suspended in TEDGT buffer and dialyzed against TEDGT buffer to remove the ammonium sulfate.

The dialyzed solution was then loaded onto a Heparin-Agarose column (SPL 1905-0004) equilibrated with TEDGT buffer. After washing the column with TEDGT buffer, elution was performed by applying a linear gradient of 0 to 1 M NaCl TEDGT buffer. The fractions were collected, and assayed for DNA polymerase activity as described in Example 2. Fractions with DNA polymerase activity were pooled. The presence of endonucleases was determined by incubating the equivalent of 1/64, 1/16, 1/8, 1/4, 1/2, and 1 µl of the pooled fractions with 1 µg lambda DNA (Promega, D150) in buffer E (Promega, R005A) for one hour at 74° C. Agarose gel analysis of the digest showed no restriction enzyme activity. The pooled fractions were dialyzed against TEDGT buffer, then loaded onto a TEDGT buffer equilibrated Cibacron Blue column (Sigma, C-1535). After washing the column with TEDGT buffer, elution was performed with a linear gradient of 0 to 1 M NaCl TEDGT buffer. The eluate was collected in fractions, and each fraction was assayed for DNA polymerase activity.

Fractions that contained DNA polymerase activity were pooled, dialyzed against TEDGT buffer, and loaded onto a TEDGT buffer equilibrated DEAE-Sepharose column (Sigma DCL-6B-100). After washing the column with TEDGT buffer, elution was performed with a linear gradient of 0 to 1 M TEDGT buffer. The eluate was collected in fractions, and assayed for DNA polymerase activity. The fraction that showed the highest DNA polymerase activity was dialyzed against TEDGT buffer before it was loaded onto a TEDGT equilibrated DNA-Agarose column (Promega). After washing the column with TEDGT buffer, elution was performed with a linear gradient of 0 to 1 M NaCl TEDGT buffer. The eluate was collected in fractions, and assayed for DNA polymerase activity. Endonuclease and nickase activities were assayed by incubating 5 µl of fractions with the highest DNA polymerase activity with 1 µg of PhiX174 DNA digested with Hae III restriction enzyme (Promega, G176A) or pBR322 plasmid DNA (Promega D151A) in buffer E (Promega R005A) for 3⅓ hours at 70° C. Fractions that showed highest level of DNA polymerase activity and no substantial endonuclease or nickase activity were pooled to yield a 3 ml solution. Sixty microliters 10% Tween 20 and 60 µl 10% NP40 detergents were added, and dialyzed against the storage buffer (20 mM Tris-HCl pH 8.0, 100 mM KCl, 0.1 mM EDTA, 1 mM DTT, 50% glycerol, 0.5% NP-40, and 0.5% Tween 20), diluted with the storage buffer to a concentration of 5 units (as defined in Example 2) per microliter and stored at −20° C.

This experiment demonstrated that the Tvu DNA polymerase was purified to greater than 95% pure as indicated by the substantial absence of nuclease contamination, and a predominant band at about 97 kD when compared to Mark 12 size markers (Novex, LC5677) on a 4-20% Tris-Glycine gel (Novex EC6025).

Example 2

DNA Polymerization Activity Assay

Activity of native, thermostable Tvu DNA polymerase purified as described in Example 1 was assayed by incorporation of radiolabeled dTTP into nicked and gapped (i.e., activated) calf thymus DNA prepared as described below. One unit of thermostable DNA polymerase is defined as the amount of enzyme required to catalyze the incorporation of 10 nmol of dNTP into an acid-insoluble form in 30 minutes at 74° C. The reaction conditions comprised: 50 mM Tris-HCl (pH 9.0 at 25° C.), 50 mM NaCl, 10 mM $MgCl_2$, 12 µg activated calf thymus DNA, 0.2 mM dATP, 0.2 mM dGTP, 0.2 mM dCTP, 0.2 mM dTTP (Promega, U1240), and 1 µCi of $^3$HdTTP (Amersham, #TRK.424) per 50 µl reaction.

The reaction components were assembled at room temperature. Samples suspected of containing polymerase activity were added (5 µl containing 0.05 to 0.5 units) and the tube was incubated at 74° C. for 30 minutes. Then, 50 µl aliquots were removed at 6, 9, 12, and 15 minutes and placed in separate tubes on ice. The $^3$H-dTTP incorporation was determined by measuring TCA precipitation counts by the following procedure. To each 50 µl aliquot, 500 µl 10% cold TCA solution was added and the tubes were incubated on ice for 10 minutes before the contents of each tube were filtered onto a separate GF/A filter (Whatman, 1820 024). The filters were washed with 5 ml 5% cold TCA solution three times, and once with acetone. The filters were dried under a heat lamp, put into a scintillation vial, and then counted in a liquid scintillation counter in scintillation fluid (Beckman, 158735). A no-enzyme negative control was also performed using 50 µl DNA polymerase activity assay mix and washed as above. The total counts of each reaction were determined using 5 µl of DNA polymerase activity assay mix directly.

Activated calf thymus DNA was prepared by dissolving 1 g calf thymus DNA (#D-151, Sigma) in 400 ml TM buffer (10 mM Tris-HCl (pH 7.3), 5 mM $MgCl_2$). Four hundred microliters of a solution containing 40 unites of RQ1-DNase (Promega) in TM buffer was added to the DNA solution and incubated at 37° C. for 10 minutes. The DNase digestion was stopped by heating the DNA solution at 68° C. for 30 minutes. The activated calf thymus DNA was stored at −20° C. until used. The activated calf thymus DNA was heated to 74° C. for 10 minutes and then cooled to room temperature before use.

Example 3

Comparison of RT Activity of Thermostable DNA Polymerases in the Presence of $Mg^{2+}$ or $Mn^{2+}$ Ions This example describes the determination of the reverse transcriptase activity of several different DNA polymerases in the presence of either $Mg^{2+}$ or $Mn^{2+}$ ions. In these experiments, a reverse transcription (RT) reaction mix was used. The final concentration of each component in a reaction was: 10 mM Tris-HCl (pH 8.3), 90 mM KCl, 0.5 mM dTTP (Promega, U123A), 0.25 mM polyriboadenylate, 0.025 mM oligodeoxythymidylate (Supertechs 111020A), and 0.25 μCi 3HdTTP (Amersham Life Science, catalog #TRK.424) in 50 μl reaction volume.

Each 45 μl aliquot of the RT reaction mix was mixed with 2 μl (10 units) of one of the DNA polymerases, and 1 μl of either 50 mM $MnCl_2$ or 50 mM $MgCl_2$. The solutions were then incubated at 70° C. for 15 minutes. Reactions were stopped by placing them on ice. native Taq, sequencing grade Taq (sTaq), and Tth were from Promega (M166, M203, M210 respectively), Tne was purified as described in U.S. Pat. No. 6,001,645 incorporated herein by reference. The negative control was performed as described but without addition of any enzyme.

The $^3$HdTTP incorporation was determined by measuring TCA precipitation counts as follows. Each RT reaction was TCA precipitated by adding 10 μl calf thymus DNA (1 mg/ml), 500 μl 10% cold TCA solution, and then allowed to sit on ice for 10 minutes before it was filtered onto GF/C filter (Whatman, 1822024). The filter was washed with 5 ml 5% cold TCA solution three times, and once with acetone. The filter was dried under a heat lamp, and then counted in a liquid scintillation counter in scintillation fluid (Beckman, 158735). The results (corrected for background) are presented in Table 2.

TABLE 2

Reverse Transcriptase Activity

| Enzyme | $MnCl_2$ (mM) | $MgCl_2$ (mM) | $^3$H-dTTP Incorporation (CPA) |
|---|---|---|---|
| native Tvu | 1 | — | 35654 |
| native Tvu | — | 1 | 10502 |
| Taq | 1 | — | 11110 |
| Taq | — | 1 | 70 |
| sTaq⁺ | 1 | — | 9920 |
| sTaq⁺ | — | 1 | 192 |
| Tth | 1 | — | 11201 |

TABLE 2-continued

Reverse Transcriptase Activity

| Enzyme | $MnCl_2$ (mM) | $MgCl_2$ (mM) | $^3$H-dTTP Incorporation (CPA) |
|---|---|---|---|
| Tth* | 1 | — | 19988 |
| Tth* | — | 1 | 160 |
| Tne | 1 | — | 14456 |
| Tne | — | 1 | 114 |

*Reaction was done in 0.05% Tomah E-18-15 detergent
⁺Sequencing grade Taq

This experiment demonstrated that: 1) the DNA polymerases tested had high RT activity in the presence of $Mn^{2+}$; 2) addition of 0.05% Tomah E-18-15 detergent (e.g., U.S. patent application Ser. No. 09/338,174, incorporated herein by reference) increased Tth RT activity by 80% in $Mn^{2+}$ buffer; and 3) of the polymerases tested, only Tvu DNA polymerase has significant reverse transcriptase activity in the presence of $Mg^{2+}$ ions. As indicated by the data, the reverse transcriptase activity of Tvu DNA polymerase is approximately 150 times higher than native Taq DNA polymerase, approximately 52 times higher than sequencing-grade Taq DNA polymerase, approximately 66 times higher than Tth DNA polymerase, and approximately 92 times higher than Tne DNA polymerase in the presence of 1 mM $MgCl_2$.

Example 4

Reverse Transcriptase Activity of Tvu DNA Polymerase Tested Over a Range of Magnesium Concentrations This example describes the determination of the magnesium ion concentration at which Tvu DNA polymerase has the highest reverse transcriptase activity. A reverse transcription (RT) reaction mix was prepared as described in Example 3 above, except that 10 mM KCl (i.e., instead of 90 mM KCl) was used in the 10×RT buffer. The mix components and their concentrations are indicated in Table 3.

TABLE 3

Reverse Transcriptase Reactions

| Component | Amount | | | | | | | | |
|---|---|---|---|---|---|---|---|---|---|
| 50 mM $MgCl_2$ (μl) | 1 | 1.5 | 2 | 2.5 | 0 | 0 | 0 | 0 | 0 |
| 100 mM $MgCl_2$ (μl) | 0 | 0 | 0 | 0 | 1.5 | 1.75 | 2 | 2.5 | 0 |
| 5 u/μl Tvu (μl) | 2 | 2 | 2 | 2 | 2 | 2 | 2 | 2 | 0 |
| RT reaction mix (μl) | 45 | 45 | 45 | 45 | 45 | 45 | 45 | 45 | 45 |
| $Mg^{2+}$ Concentration in Each Reaction (mM) | | | | | | | | | |
| | 1.0 | 1.5 | 2.0 | 2.5 | 3.0 | 3.5 | 4.0 | 5.0 | 0 |

Each reaction was incubated at 70° C. for 20 minutes. Reactions were stopped by placing them on ice. The $^3$HdTTP incorporation was determined by measuring TCA precipitation counts as described in Example 3. The results are presented in Table 4 (all values shown were corrected for background).

TABLE 4

Reverse Transcriptase Assay

| MgCl$_2$ (mM) | $^3$HdTTP Incorporation (CPA) |
|---|---|
| 1.0 | 14464 |
| 1.5 | 22787 |
| 2.0 | 25427 |
| 3.0 | 32395 |
| 3.5 | 25580 |
| 4.0 | 27472 |
| 5.0 | 26487 |

This experiment demonstrates that the reverse transcriptase activity of Tvu DNA polymerase increased at levels from 1 to 3 mM Mg$^{2+}$, was maximum at 3 mM Mg$^{2+}$, and then decreased when the Mg$^{2+}$ concentration was increased above 3 mM.

Example 5

Reverse Transcriptase Activity of Tvu DNA Polymerase Tested Over a Range of Manganese Ion Concentrations This experiments describes the determination of the optimum Mn$^{2+}$ concentration for reverse transcriptase activity. A reverse transcription (RT) reaction mix was prepared as described in Example 3, except that Tomah E-18-15 detergent was added to a final concentration of 0.01%, and Tvu DNA polymerase was added to a final concentration of 0.07 units per µl of RT reaction mix. The mix components are indicated in Table 5.

TABLE 5

Reverse Transcription Reactions

| Component | Amount | | | | | | |
|---|---|---|---|---|---|---|---|
| 25 mM MnCl$_2$ (µl) | 0 | 0 | 1.2 | 1.4 | 1.6 | 1.8 | 2.0 |
| 10 mM MnCl$_2$ (µl) | 2 | 2.5 | 0 | 0 | 0 | 0 | 0 |
| RT reaction mix (µl) | 45 | 45 | 45 | 45 | 45 | 45 | 45 |
| Mn$^{2+}$ Concentration in Each Reaction (mM) | | | | | | | |
| | 0.4 | 0.5 | 0.6 | 0.7 | 0.8 | 0.9 | 1.0 |

Each reaction was incubated at 74° C. for 20 minutes. Reactions were stopped by placing them on ice. The $^3$HdTTP incorporation was determined by measuring TCA precipitation counts as described in Example 3. The results are shown in Table 6 (all values shown were corrected for background).

TABLE 6

Reverse Transcriptase Activity

| MnCl$_2$ (mM) | $^3$HdTTP incorporation (CPA) |
|---|---|
| 0.4 | 7670 |
| 0.5 | 8258 |
| 0.6 | 9200 |
| 0.7 | 8718 |

TABLE 6-continued

Reverse Transcriptase Activity

| MnCl$_2$ (mM) | $^3$HdTTP incorporation (CPA) |
|---|---|
| 0.8 | 7600 |
| 0.9 | 7616 |
| 1.0 | 7610 |

This experiment demonstrates that the reverse transcriptase activity of Tvu DNA polymerase increased as the level of Mn$^{2+}$ in the reaction increased from 0.4 to 0.6 mM, was maximum at 0.6 mM Mn$^{2+}$, and decreased when Mn$^{2+}$ concentration was increased above 0.6 mM.

Example 6

Tvu and Bst Reverse Transcriptase Activity in Mg$^{2+}$ Buffer

This example compares the reverse transcriptase (RT) activity of Tvu DNA polymerase with that of Bst DNA polymerase (NEB, 275L). In these experiments, a RT reaction mix was prepared with the final concentration of each component of the mix in a reaction: 50 mM Tris-HCl (pH 8.3), 40 mM KCl, 0.5 mM dTTP (Promega, U123A), 7 mM MgCl$_2$, 10 mM DTT, 0.25 mM polyriboadenylate, 0.025 mM oligodeoxythymidylate (Supertechs, #111020A), and 0.25 Ci$^3$ HdTTP (Amersham, TRK.424) in a 50 µl reaction.

A 45 µl aliquot of the RT reaction mix was mixed with 1.25 units enzyme. The solution was then incubated at 70° C. for 15 minutes for the Tvu DNA polymerase, and 65° C. for 15 minutes for the Bst DNA polymerase. The reactions were stopped by placing them on ice. The experiment was repeated for differing amounts of enzyme. A negative control was performed without any enzymes.

The results are presented in Table 7 (all values shown were corrected for background).

TABLE 7

Reverse Transcriptase Activity

| Enzyme Units | $^3$HdTTP Incorporation (CPM) |
|---|---|
| Tvu DNA Polymerase at 74° C. | |
| 1.25 | 2054 |
| 2.5 | 2890 |
| 5 | 15786 |
| Bst DNA Polymerase at 65° C. | |
| 1.25 | 26374 |
| 2.5 | 34492 |
| 5 | 39602 |
| 8 | 52757 |

This example demonstrates that Bst DNA polymerase has reverse transcriptase activity in the presence of Mg$^+$.

Example 7

Thermostability of Tvu DNA Polymerase

This example was performed to determine the thermostability of Tvu DNA polymerase. Tvu DNA polymerase (0.08 units) was added to 55 µl of DNA polymerase activity assay mix described in Example 2. The solution was incubated at 70° C. for 10 minutes. The reaction was terminated by placing the tube on ice. The $^3$H-dTTP incorporation was determined by measuring TCA precipitation counts (See Example 2). The experiment was repeated using incubation temperatures of 72, 74, 76, 78, and 80° C. The results are presented in Table 8 (all values were corrected for background).

TABLE 8

Thermostability

| Temperature (° C.) | $^3$H-dTTP Incorporation (CPM) |
|---|---|
| 70 | 7458 |
| 72 | 6556 |
| 74 | 3834 |
| 76 | 1202 |
| 78 | 790 |
| 80 | 596 |

This experiment demonstrates that Tvu DNA polymerase activity decreases as the temperature increases above 70° C. and that the optimal temperature for Tvu DNA polymerase activity is about 70° C. or lower.

Example 8

Comparison of Bst Reverse Transcriptase Activity in the Presence of $Mg^{2+}$ or $Mn^{2+}$ In this example, the reverse transcriptase activity of Bst DNA polymerase in reaction mixes comprising either $Mg^{2+}$ or $Mn^{2+}$ was compared. A reverse transcription (RT) reaction mix was prepared as in Example 3, except that Tomah E-18-15 detergent was added to the mix to a final concentration of 0.1%. A 45 µl aliquot of the RT reaction mix was mixed with 1 µl (8 units) enzyme, and 1 µl of either 50 mM $MnCl_2$ or 100 mM $MgCl_2$, and 3 µl 1% Tomah E-18-15 detergent. The solutions were then incubated at 65° C. for 20 minutes. Reactions were stopped by placing them on ice. A negative control was performed as described, with the absence of any enzyme. The $^3$HdTTP incorporation was determined by measuring TCA precipitation counts as described in Example 3. The results are presented in Table 8 (all values shown were corrected for background).

TABLE 9

Reverse Transcriptase Activity

| $MgCl_2$ (mM) | $MnCl_2$ (mM) | $^3$HdTTP Incorporation (CPM) |
|---|---|---|
| — | 1 | 69476 |
| 2 | — | 49560 |

This example demonstrates that Bst DNA polymerase has reverse transcriptase activity in the presence of both $Mg^{2+}$ and $Mn^{2+}$ ions.

Example 9

Tvu and Bst Reverse Transcriptase Activity at High Temperature

This example was performed to determine the optimum temperature for the reverse transcriptase activity of Tvu and Bst DNA polymerase. A 25 ill solution, containing 2.5 units Tvu or Bst DNA polymerase, 2 mM $MgCl_2$, and IX RT reaction mix (See Example 3) was made. The solution was incubated at 65° C. for 10 minutes. The reaction was then terminated by placing it on ice. The $^3$HdTTP incorporation was determined by measuring TCA precipitation counts as described in Example 3. The experiment was repeated using incubation temperatures of 68, 70, 72, 74, 76, and 78° C. The results obtained are presented in Table 10 (results were corrected to remove background).

TABLE 10

Reverse Transcriptase Activity at High Temperature

| Temperature (° C.) | $^3$HdTTP Incorporation (CPM) |
|---|---|
| Tvu DNA Polymerase | |
| 65 | 1756 |
| 68 | 1906 |
| 70 | 1458 |
| 72 | 1432 |
| 74 | 620 |
| 76 | 560 |
| 78 | 530 |
| Bst DNA Polymerase | |
| 65 | 3356 |
| 68 | 2364 |
| 70 | 1294 |
| 72 | 1258 |
| 74 | 1298 |
| 76 | 1186 |
| 78 | 1360 |

This experiment demonstrates that Tvu DNA polymerase reverse transcriptase activity increases as the reaction temperature rises from 65° C. to 68° C., is maximum at 68° C., and then decreases at temperatures above 74° C. This suggests that the optimal temperature for the reverse transcriptase activity of Tvu DNA polymerase is approximately 68° C. The Bst DNA polymerase reverse transcriptase activity was maximum at 65° C., and these data suggest that the optimal temperature for Bst reverse transcriptase activity is at or below about 65° C.

Example 10

Tvu and Bst DNA Polymerase PCR

To demonstrate that Tvu DNA polymerases can be used to perform PCR, the following experiment was performed. A 49 µl solution, containing PCR buffer, dNTP (Promega U1240), template DNA, primer A, primer B (DNAs described below), and additives (Betaine for Bst, Formamide for Tvu) was made. The solution was incubated in a thermocycler at 95° C. for 2 minutes. The solution was then cooled to and incubated at 65° C. for 2 minutes. During this time, 1 µl of Bst (8 u/µl) or Tvu DNA polymerase (5 u/µl) was added to the solution to bring the final concentration of each component to the following: 10 mM Tris-HCl (pH7.5), 50 mM NaCl, 10 mM $MgCl_2$, 1.5 mM dNTP, 10 ng template DNA, 1 µM primer A, 1 µM primer B, and 1M Betaine for Bst or 0.5% Formamide for Tvu. The solution was incubated for 35 cycles (75° C. for 15 seconds, and 65° C. for 2 minutes). The final extension reaction was performed at 65° C. for 5 minutes. The reaction was then stored at 4° C. Ten µl of the reaction were then loaded onto a 20% TBE gel (Novex, EC6315). The gel was run at 230 volts for 60 minutes and stained with ethidium bromide. A 36 bp band was detected for both DNA polymerase reactions. This example demonstrates that both Bst and Tvu DNA polymerases are capable of performing PCR under the conditions described in this example.

In these experiments, Primer A (Promega, 9078) had the following sequence: 5'-GACGTCGCATGCTCCT-3' (SEQ ID NO:7); while Primer B (Promega, 9080) had the following sequence: sequence 5'-ACCGAATTCCTCGAGTC-3' (SEQ ID NO:8). Template DNA was made by digesting plasmid pGEM-7fz+ (Promega, p225A) with restriction enzymes ApaI and KpnI.

Example 11

Cloning Recombinant Tvu DNA Polymerases—Wild-type and Mutant Forms

Cloning of Gene Encoding Wild-Type Tvu DNA Polymerase

Genomic DNA was isolated from Tvu and used to clone the full-length Tvu DNA polymerase into an expression vector. Two mutant recombinant Tvu DNA polymerases were then constructed, both of which have deleted the 5' to 3' exonuclease-encoding domain.

Genomic DNA was isolated from Tvu by resuspending Tvu cells grown overnight in Luria Broth in TE (10 mM Tris, 1 mM EDTA) and vortexing vigorously. The cell solution was then combined with 0.1 mm glass/zircon beads and beaten at 5000 rpm for 2 cycles of 20 seconds each. The cells were then fully dispersed and appeared to be lysed. The liquid was transfered to a fresh tube and extracted twice with phenol and once with chloroform. Each time the aqueous phase was transferred to a clean tube. The aqueous phase was then treated with RNase I and ethanol precipitated. The DNA was spooled and washed in 70% ethanol before drying. The dried DNA pellet was then resuspended in TE to a final concentration of 3 μg/μl.

The DNA polymerase domain was amplified from the Tvu genomic DNA by PCR. The following components were combined:

| | |
|---|---|
| Tvu genomic DNA (predenatured at 98° C., 2 minutes) | 1 μl |
| Primer JH47 (500 picomoles) | 1 μl |
| Primer JH49 (500 picomoles) | 1 μl |
| 10X Taq buffer with 15 mM MgCl$_2$ (Promega, | 5 μl |
| 10 mM dNTPs | 1 μl |
| Nanopure water | 40 μl |

The sequence of the degenerate primers used are conserved in DNA polymerases and are listed below:

```
JH47
TAGAGCGGCCGCGAYCCIAAYYTICARAAYAT    (SEQ ID NO:9)

JH49
CTGCGGCCGCCTAIIACIAIYTCRTCRTGIAC    (SEQ ID NO:10)
```

Y indicates a pyrimidine (T or C)

I indicates inosine which anneals with any of the four conventional bases

R indicates a purine (A or G)

The PCR cycling profile was: 96° C., 1 min (94° C., 15 sec; 32° C., 30 sec; 72° C., 1 min)×25 cycles, 72° C. 1 minute. A 600 base pair fragment was produced as expected. The PCR product was purified with Wizard PCR Purification System (Promega, A7170) according to manufacturer's instructions. Twenty-five nanograms of the fragment was ligated to 50 ng T-vector (Promega, A3600) according to manufacturer's instructions. Four microliters of the ligation was transformed into competent JM109 cells. Clones were selected, digested with the Pvu II restriction enzyme and demonstrated to contain the 600 base pair PCR product. The product was sequenced by dideoxy sequencing. When the resulting amino acid sequence encoded by this polynucleotide was compared to the amino acid sequence of E. coli PolA and Taq DNA polymerase, it demonstrated about 50% homology to both, indicating that the cloned PCR product originated from the DNA polymerase gene of Tvu.

Oligonucleotide 11300 (5'-GCGCGAAGAACGGCTG-CAGGC-3', SEQ ID NO: 11) which is within the 600 bp PCR fragment was labelled with $^{33}$P-ATP using T4 polynucleotide kinase and used as a probe for a Southern blot. The Southern blot had Tvu genomic DNA digested with one of seven different restriction enzymes (BamH I, Acc65 I, Apa I, EcoR I, Hind III, Spe I, Xba I, Xho I) per lane. The prehybridization conditions were 65° C., 1.5 hours in 3 ml of 1×SSPE, 10% PEG-8000, 7% SDS, 250 μg/ml denatured Herring Sperm DNA. Hybridization conditions were the same solution as used for the prehybridization with the addition of the radiolabeled probe purified on a G-25 column and reaction at 50° C. for four hours. The washes were 15 to 30 minutes each, 200 ml of 0.3×SSC, 0.1% SDS at 25° C., repeated, followed by three washes of 200 ml of 0.3×SSC, 0.1% SDS at 50° C. The blot was then exposed to X-OMAT film for 2 days at 22° C. There was one band of about 3 kb detectable in the Hind III digested lane and one band larger than 10 kb detectable in the Xho I digested lane.

Tvu genomic DNA was digested with Hind III restriction enzyme and run into a 0.4% TAE agarose gel. The region near the 3 kb position was cut out of the gel, purified with Wizard PCR Purification System (Promega, A7170). The purified 3 kb fragment was ligated into pZERO-2 (Invitrogen) and transformed into TOP10 cells (LTI). Ninety-six clones were picked and each grown in 200 ul LB media containing 30 ug/ml kanamycin, shaking overnight at 37° C. The cultures were dot blotted using oligonucleotide 11300 described above as the probe and prehybridization and hybridization conditions also described above. The washes were two 150 ml washes of 0.5×SSC, 0.1% SDS at 25° C., 15-30 minutes each, followed by three 150 ml washes of 0.5×SSC, 0.1% SDS at 50° C., 15-30 minutes each. The blot was then exposed to X-OMAT film for two hours and developed. Two colonies produced a strong signal. They were grown and plasmid isolated therefrom. The cloned fragments in the plasmids were sequenced and indicated that the Hind III restriction enzyme site was 183 base pairs upstream of the QNIP conserved region indicating about one third of the DNA polymerase gene (the C-terminus) was present in the clone.

To clone upstream of the Hind III site in the gene, a second PCR amplification was designed to amplify the region upstream of the Hind III site. Again, a degenerate primer (JH31) was used that contained conserved sequence present in DNA polymerases. The second primer (11299) was chosen from within the previously cloned Hind III fragment of Tvu DNA polymerase. The following PCR reaction was assembled:

| | |
|---|---|
| Tvu genomic DNA | 1 μl |
| JH31 primer 400 pmoles | 4 μl |
| 11299 primer 50 pmoles | 5 μl |
| 10 mM dNTPs | 1 μl |
| 10× Taq buffer | 5 μl |
| 50 mM MgSO$_4$ | 2 μl |
| Taq polymerase | 1 μl |
| Water/enhancer | 31 μl |

```
JH31    TTCAACCIIAACTCIIIIIAICAGCT    (SEQ ID NO:12)

11299   CGGCTCCGACGGCACGAACG          (SEQ ID NO:13)
```

The PCR cycling conditions were 96° C., 1 minute (94° C., 15 sec; 37° C., 30 sec; 72° C., 1 minute)×25, 72° C., 1 minute. The PCR reaction was run on a 1.2% TBE/agarose gel. The resulting 350 bp band was as expected and was purified using Wizard PCR Purification System (Promega, A7170). The fragment was ligated into a T-vector and transformed into JM109 cells. Positive clones were sequenced. The sequence downstream from the Hind III site was identical to the previous clone. The sequence upstream of the Hind III site encoded amino acids homologous to other DNA polymerases.

New Tvu genomic DNA was isolated as previously described, except that cells were lysed with proteinase K, in order to obtain DNA that was less sheared than the present stock. An oligonucleotide (11761) was prepared using sequence upstream of the Hind III site obtained as described above. This oligonucleotide sequence is listed below.

```
11761   TCAACACCGGGAGCTGCAGCTTGTCA    (SEQ ID NO:14)
```

Tvu genomic DNA was digested with Hind III or Hind III plus another restriction enzyme (Acc I, BamH I, Bgl II, EcoR I, Spe I, Xba I, Xho I, Xho II) and each digested sample run on a lane of a 0.6% TBE/agarose gel. The DNA in the gel was transferred to a nylon membrane by Southern blot procedure. The 11761 oligonucleotide was end labelled with $^{33}$P-gamma-ATP using T4 polynucleotide kinase and purified over a NAP-5 column (Pharmacia) according to manufacturer's instructions. Prehybridization, Hybridization, and Wash conditions were as previously described. The membrane was then exposed to X-OMAT film for several days and developed. There was a 4 kb band in all of the lanes except for the Hind III+EcoR I digest lane in which the band was slightly smaller. These results indicate that there is a Hind III restriction enzyme site located about 4 kb upstream of the Hind III site previously localized to the coding sequence of Tvu DNA polymerase.

Tvu genomic DNA was digested with Hind III and run into a 0.6% TBE/agarose gel. The agarose at the 4 kb position was cut out of the gel and the DNA isolated. The resulting DNA was ligated into pZERO-2 (Invitrogen) at the Hind III site and transformed into TOP 10 cells. Clones were screened by dot blot as described above using the 11761 radiolabeled oligonucleotide as the probe. A positive clone was grown, the plasmid purified, and the insert containing the remainder of the Tvu DNA polymerase gene was sequenced.

The two Hind III fragments were cloned in correct order into Litmus 29 plasmid (New England Biolabs) and resequenced across fragment junctions. This full length clone of Tvu DNA polymerase in Litmus 29 plasmid is named L29b. The resulting open reading frame nucleotide sequence is SEQ ID NO: 1.

Mutant Tvu DNA Polymerase Construction—T289M

The construction of T289M mutant of Tvu DNA polymerase resulted in a plasmid containing an IPTG-inducible mammalian promoter directing expression of the Tvu DNA fragment beginning at the nucleotides encoding amino acid 289 of the wild type enzyme, mutated to encode a methionine residue instead of a threonine, and ending at the termination codon of the wild type enzyme.

The JHEX25 vector (Promega) was digested with Nco I and Acc65 I restriction enzymes and the large linear band isolated from an agarose gel. The L29b vector, described above, was digested with Sgf I and Acc65 I restriction enzymes and the 1.8 kb band isolated from an agarose gel. The Sgf I cut site in L29b is located 912 base pairs downstream from the polymerase start codon and the Acc65 I cut site in L29b is located 69 base pairs downstream from the polymerase termination codon.

Oligonucleotides 12144 and 12145 were designed such that when they are annealed to each other an Sgf I overhang exists on one end and an Nco I overhang exists on the other end. The ATG within the Nco I site creates the new, non-native start site for the T289M DNA polymerase. The oligonucleotides were annealed by combining in a tube 2 pmols/µl of each in TNE (10 mM Tris, 5 mM NaCl, 1 mM EDTA), placing the tube in a 9600 thermocycler and slowly decreasing the temperature from 80° C. to 25° C. over a period of 40 minutes.

The purified Sgf I/Acc65 I fragment of L29b was ligated to 2 pmols of annealed 12144/12145 oligonucleotides using T4 DNA ligase at room temperature for about two hours. Four microliters of the ligation reaction was then transformed into JM109 cells and plated onto LB plates containing tetracycline. Colonies were screened by isolating plasmid and digesting with Nco I and Acc65 I restriction enzymes and further confirmed to be correct by dideoxy sequencing across the sequence encoding the DNA polymerase. The plasmid was named TvuK-25. The nucleotide sequence encoding the T289M polymerase is shown in FIG. 5, SEQ ID NO: 5. The amino acid sequence of T289M polymerase is shown in FIG. 6, SEQ ID NO: 6.

```
12144                                  (SEQ ID NO:15)
CATGGATGAAGGTGAGAAGCCACTGGCCGGGATGGACTTTGCGAT;
and 12145                                  (SEQ ID NO:16)
CGCAAAGTCCATCCCGGCCAGTGGCTTCTCACCTTCATC
```

Mutant Tvu DNA Polymerase Construction—M285

The construction of the M285 mutant of Tvu DNA polymerase resulted in a plasmid containing an IPTG-inducible mammalian promoter directing expression of the Tvu DNA fragment beginning at the nucleotides encoding the methionine amino acid at position 285 of the wild type enzyme and ending at the termination codon of the wild type enzyme.

The TvuK-25 plasmid described above was digested with Dra I and Sgf I restriction enzymes. The large linear band was isolated from an agarose gel. Oligonucleotides 12230 and 12231 were designed such that when they are annealed to each other an Sgf I overhang exists on one end and a Dra I overhang exists on the other end. The oligonucleotides were annealed by combining in a tube 2 pmols/µl of each in TNE (10 mM Tris, 5 mM NaCl, 1 mM EDTA), placing the tube in a 9600 thermocycler and slowly decreasing the temperature from 80° C. to 25° C. over a period of 40 minutes.

The purified Sgf I/Dra I fragment of TvuK-25 was ligated to 2 pmols of annealed 12230/12231 oligonucleotides using T4 DNA ligase at room temperature for about two hours. Four microliters of the ligation reaction was then transformed into JM109 cells and plated onto LB plates containing tetracycline. Colonies were screened by isolating plasmid and digesting with either Dra I or AccB7 I restriction enzymes and further confirmed to be correct by dideoxy sequencing across the sequence encoding the DNA polymerase.

The nucleotide sequence encoding the M285 polymerase is shown in FIG. 3, SEQ ID NO: 3. The amino acid sequence of M285 polymerase is shown in FIG. 4, SEQ ID NO: 4.

```
12230                                              (SEQ ID NO:17)
AAACCATGGCAGTTCAAACCGATGAAGCCGAGAAACCACTGGCTGG
GATGGACTTTGCGAT;
and 12231                                              (SEQ ID NO:18)
CGCAAAGTCCATCCCAGCCAGTGGTTTCTCGCCTTCATCGG
TTTGAACTGCCATGGTTT
```

Example 12

Expression and Purification of Recombinant Tvu DNA Polymerases

The recombinant Tvu DNA polymerases, both full-length and mutant, were expressed and purified as described herein. For the full-length clone, a liter of Terrific Broth containing 100 ug/ml ampicillin was grown at 37° C. to saturation with E. coli transformed with the vector capable of expressing recombinant full-length Tvu DNA polymerase (described in Example 11). The cells were harvested by centrifugation at 9,000 rpm for 5 minutes.

For the full-length recombinant Tvu DNA polymerase, 20 g cell paste was combined with 200 ml of 0.25 M NaCl TEDG (50 mM Tris-HCl at pH 7.3, 1 mM EDTA, 1 mM DTT, and 10% Glycerol) containing 2.5 mM PMSF. The solution was sonicated at 100% output three times for two minutes each at 10° C. The solution (40 ml aliquots) was then heat treated at 65° C. for 5 minutes and then cooled to 4° C. Then 4 ml of 5% PEI was added to the lysate to precipitate the DNA. The following purification steps were performed at 4° C. Centrifugation (12,000 rpm in a Beckman JA18 rotor for 90 minutes) was used to separate the supernatant from the precipitate. The supernatant was then collected, and ammonium sulfate was added to a final saturation of 65% to precipitate the DNA polymerase. Centrifugation (15,000 rpm in a Beckman JA18 rotor for 30 minutes) was used to separate the ammonium sulfate precipitate from the supernatant. The precipitate was collected, suspended in TEDG buffer and dialyzed against TEDG buffer containing 2.5 mM PMSF overnight to remove the ammonium sulfate.

The dialyzed solution was then loaded onto a Heparin-Agarose column (SPL 1905-0004) equilibrated with TEDG buffer. After washing the column with TEDG buffer, elution was performed by applying a linear gradient of 0 to 0.6 M NaCl TEDG buffer. The fractions were collected, and assayed for DNA polymerase activity as described in Example 2. The presence of endonucleases was determined by incubating 2 μl of fractions with 1 μg lambda DNA (Promega, D150) or pBR322 plasmid DNA in activity assay buffer for 17 hours at 70° C. Agarose gel analysis of the digest showed no evidence of nuclease contamination. Fractions with DNA polymerase activity were pooled. The pooled fractions were dialyzed against TEDG buffer, then loaded onto a TEDG buffer equilibrated Cibacron Blue column (Sigma, C-1535). After washing the column with 0.05 M NaCl/TEDG buffer, elution was performed with a linear gradient of 0.05 to 0.75 M NaCl/TEDG buffer. The eluate was collected in fractions, and sample fractions were assayed for DNA polymerase activity and retested for nuclease contamination. No such contamination was detected. The fractions with DNA polymerase activity were pooled and Tomah-34 detergent added to a final concentration of 0.2% (e.g., U.S. patent application Ser. No. 09/338,174, incorporated herein by reference). The polymerase solution was then dialyzed overnight against the storage buffer (50% glycercol, 20 mM Tris, pH 8.0 at 25° C., 100 mM KCl, 0.1 mM EDTA, 1 mM DTT, 0.5% Toman-34).

The mutant Tvu DNA polymerases (M285 and T289M) encoded by IPTG-inducible plasmids. For growth of these mutant plasmids, 3 liters of Terrific Broth containing 10 ug/ml tetracycline were seeded separately with 50 ml overnight seedstocks of E. coli containing either mutant plasmid. The cultures were grown to about A600=1.5 OD shaking at 37° C. Then the culture growth temperature was adjusted to 25° C. and IPTG was added to a final concentration of 1 mM. The culture was allowed to grow overnight, shaking at 25° C. and the cells were then harvested by centrifugation at 9,000 rpm for 5 minutes. The purification procedure is then the same as that described above for the full-length rTvu DNA polymerase.

This experiment demonstrated that the recombinant Tvu DNA polymerases were purified to greater than 95% as indicated by a predominant band at about 97 kD for the full-length polymerase and 66 kD for the mutant polymerases when compared to Mark 12 size markers (Novex) on a 4-20% Tris-Glycine gel (Novex EC6025).

Example 13

Use of Recombinant Tvu DNA Polymerases in Reverse Transcription Reaction

Reverse transcription activity in the presence of magnesium ions was measured for the full-length and mutant recombinant Tvu DNA polymerase enzymes purified as described in Example 12.

In these experiments, a reverse transcription (RT) reaction mix was used. The final concentration of each component in a reaction was: 10 mM Tris-HCl (pH 8.3), 50 mM KCl, 0.5 mM dTTP (Promega, U123A), 0.25 mM polyriboadenylate, 0.025 mM oligodeoxythymidylate (Supertechs 111020A), and 0.25 μCi $^3$HdTTP (Amersham, TRK.424) in 50 μl reaction volume.

Each 45 μl aliquot of the RT reaction mix was mixed with 2 μl (10 units) or 1 μl (5 units) of one of the DNA polymerases and water to a final volume of 50 μl. The solutions were then incubated at 74° C. for 20 minutes. Reactions were stopped by placing them on ice. The negative control was performed as described but without addition of any enzyme.

The $^3$HdTTP incorporation was determined by measuring TCA precipitation counts as follows. Each RT reaction was TCA precipitated by adding 10 μl calf thymus DNA (1 mg/ml), 500 μl 10% cold TCA solution, and then allowed to sit on ice for 10 minutes before it was filtered onto GF/C filter (Whatman, 1822024). The filter was washed with 5 ml 5% cold TCA solution three times, and once with acetone. The filter was dried under a heat lamp, and then counted in a liquid scintillation counter in scintillation fluid (Beckman, 158735). The results (corrected for background) are presented in Table 10.

TABLE 10

Reverse Transcription Activity of Recombinant Tvu DNA Polymerase

| Enzyme | Amount of Enzyme | cpm |
|---|---|---|
| Full Length rTvu DNA pol. | 5 units | 12,560 |
| Full Length rTvu DNA pol. | 10 units | 18,794 |
| M285 | 5 units | 13,202 |
| M285 | 10 units | 19,390 |

TABLE 10-continued

Reverse Transcription Activity of Recombinant Tvu DNA Polymerase

| Enzyme | Amount of Enzyme | cpm |
|---|---|---|
| T289M | 5 units | 8,434 |
| T289M | 10 units | 16,264 |

The results demonstrate that all recombinant Tvu DNA polymerases tested have reverse transcriptase activity at 74° C., and 10 units produced more activity than 5 units as expected.

Example 14 nTvu Reverse Transcriptase Functions in a Single-Step RT-PCR Reaction

This experiment describes the use of nTvu DNA polymerase in a single step RT-PCR reaction. A 30 µl solution, containing 10 mM Tris-HCl (pH8.3), 50 mM KCl, 0.2 mM dNTP, 0.3 µM primer C (Promega, A109B), 0.3 µM primer D (Promega, A110B), 1.5 mM $MgCl_2$, 5 units Tvu DNA polymerase, 5 units Taq DNA polymerase, and $10^{-12}$ moles Kanamycin mRNA (Promega, C138A), was prepared on ice. The solution was then incubated at 70° C. for 20 minutes in a thermocycler before the start of PCR: 95° C. for 1 minute, followed by 35 cycles (94° C. for 15 seconds, 60° C. for one minute), and ended with a final extension at 60° C. for 5 minutes. Following this step, the products were stored at 4° C. The experiment was repeated for $10^{-13}$, $10^{-14}$, $10^{-15}$, $10^{-16}$, $10^{-17}$, $10^{-18}$, $10^{-19}$, $10^{-20}$, $10^{-21}$ moles of kanamycin mRNA. The negative control experiment was performed without mRNA template. Ten µl of each reaction were loaded onto a 20% TBE gel and treated as in Example 10. A band of correct size was detectable in all lanes.

In these experiments, Primer C (Promega, A109B) had the following sequence 5'-GCC ATT CTC ACC GGA TTC AGT CCG T-3' (SEQ ID NO:23). Primer D (Promega, A110B) had the following sequence 5'-AGC CGC CGT CCC GTC AAG TCA G-3' (SEQ ID NO:24).

This experiment demonstrates that the reverse transcriptase activity of Tvu DNA polymerase is capable of performing RT under the RT-PCR conditions described in this Example and treated as in Example 10. A band of correct size was detectable in all lanes.

Example 15

Tvu and Bst DNA Polymerases Can Act as Reverse Transcriptases in Reverse Transcriptase Assays This experiment describes the use of Tvu and Bst DNA polymerases in RT-PCR assays. For these experiments, a 50 µl solution, containing 10 mM Tris-HCl (pH8.3), 50 mM KCl, 0.2 mM dNTP, 0.3 µM primer C (Promega, A109B), 0.3 µM primer D (Promega, A110B), 1.5 mM $MgCl_2$, either 5 units Tvu, or 5 units Bst DNA polymerase, and 0.5 µg Kanamycin RNA (Promega, C138A), was prepared on ice. A negative control experiment was carried out without mRNA template. The solution was incubated for 20 minutes at either 70° C. for Tvu, or 65° C. for Bst. Then, 5 units Taq DNA polymerase were added before the start of PCR, which was carried out at 95° C. for 1 minutes, followed by 35 cycles (94° C. for 15 seconds, 60° C. for 1 minute), and ended with a final extension at 60° C. for 5 minutes. Following this step, the products were stored at 4° C. Ten µl of each PCR reaction were loaded onto a 20% TBE gel and processed as in Example 10. The PCR product was purified using a Qiaquick PCR purification kit (Qiagene, 28104). DNA concentration was estimated using the READIT DNA quantitation method (See, e.g., U.S. application Ser. No. 09/042,287, incorporated herein by reference). Both strands of PCR products were sequenced, and were found to be completely complementary, indicating no mutations were introduced during the reaction. This example demonstrates that the reverse transcriptase activity of Tvu and Bst DNA polymerases is capable of performing RT function faithfully.

Example 16

Comparison of the Reverse Transcriptase Activity of Tli, and Pwo DNA Polymerases in $Mg^{2+}$ or $Mn^+$ Buffer This example demonstrates the lack of reverse transcriptase activity of Tli and Pwo DNA polymerases in the presence of $Mg^{2+}$ ions. In these experiments, a 45 µl aliquot of the RT reaction mix (See Example 3) was mixed with 2 µl (10 units) enzyme, and 1 µl either 50 mM $MnCl_2$ or 100 mM $MgCl_2$, and 1 µl 2.5% Tomah E-18-15 detergent. The solutions were then incubated at 70° C. for 20 minutes. Reactions were stopped by placing them on ice. Tli DNA Polymerase (Promega M7101), and Pwo DNA Polymerase (Boehringer Mannheim 1644955) were utilized in these experiments. The negative control experiment was performed without any enzymes. The $^3$HdTTP incorporation was determined by measuring TCA precipitation counts as described in Example 3. The results are presented in Table 11 (all values were corrected for background).

TABLE 11

Reverse Transcriptase Activity

| Enzyme | $MnCl_2$ (mM) | $MgCl_2$ (mM) | $^3$HdTTP Incorporation (CPM) |
|---|---|---|---|
| Tli | 1 | — | 867 |
| Tli | — | 2 | 3 |
| Pwo | 1 | 0 | 7145 |
| Pwo | — | 2 | 24 |

This example demonstrates that the reverse transcriptase activity of Tli and Pwo DNA polymerases is significant in the presence of $Mn^{2+}$ buffer, but much lower in the presence of $Mg^{2+}$ buffer.

Example 17

RT-PCR using Tvu and Taq DNA Polymerase Mixtures

Multiple mixtures of Tvu and Taq DNA polymerases were used, at multiple pHs, to demonstrate that RT-PCR can be performed in a one-pot reaction in the presence of magnesium and the substantial absence of manganese ions.

Kanamycin mRNA (Promega C1381) was used as the nucleic acid substrate in the RT-PCR reactions. The reactions were assembled as detailed in the table below.

|  | Reaction number: | | | | |
|---|---|---|---|---|---|
|  | 1 | 2 | 3 | 4 | 5 |
| Reaction mix (µl) | 43 | 43 | 43 | 43 | 43 |
| Water | 4 | 4 | 4 | 4 | 5 |
| nTaq | 1 | 1 | 1 | 1 | 1 |
| mRNA (0.5 mg/ml) | 1 | 1 | 1 | 1 | 1 |
| nTvu (full-length) | 1 | 0 | 0 | 0 | 0 |
| rTvu (full-length) | 0 | 1 | 0 | 0 | 0 |
| M285 Tvu | 0 | 0 | 1 | 0 | 0 |
| T289M Tvu | 0 | 0 | 0 | 1 | 0 |

The Taq and Tvu DNA polymerases were all at a concentration of 5 units per microliter. nTaq and nTvu are native enzymes, rTvu is the recombinant enzyme. Reaction 5 is the negative control reacton. One set of reactions was at pH 8.3, another set of reactions was at pH 9.0. The reaction mixture was: 5 µl 10× buffer (500 mM KCl, 100 mM Tris pH 8.3 or 9.0); 5 µl 2 mM dNTP, 1 µl Primer I (Promega, A109B); 1 µl Primer 2 (Promega, A110B); 5 µl 25 mM MgCl$_2$; 26 µl water.

The PCR cycling program used was 70° C. for 20 minutes to allow for reverse transcription, followed by 95° C. for 1 minute, (94° C. for 15 seconds, 68° C. for 1 minute)×30; 68° C. for 5 minutes, 4° C. soak. An aliquot of the RT-PCR reaction was then run on a 20% TBE gel and ethidium bromide stained to visualize the 300 bp product.

All of the Tvu DNA polymerase enzyme-containing reactions produced robust RT-PCR product when coupled with nTaq DNA polymerase in the above reaction. The RT reaction was run at either 70° C. or 78° C. and both produced nearly equal amounts of RT-PCR product. Likewise, pH 8.3 and pH 9.0 were both efficient and produced nearly equal amounts of RT-PCR product. The mutant and full-length Tvu DNA polymerases produced nearly equal amounts of RT-PCR product.

A 1:10 serial dilution of the mRNA template was performed and the reaction as described above was run using 2 µl of each dilution when using a Tvu DNA polymerase. RT-PCR product of 300 bp was detectable even when using an mRNA dilution containing 1 copy in the 2 µl aliquot. M285 Tvu produced a RT-PCR product of 300 bp at four logs less serial dilution than did rTvu. The other forms of Tvu were not tested in an RT-PCR reaction in the absence of Taq DNA polymerase. The negative control reactions containing no Tvu DNA polymerase produced no detectable RT-PCR product.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A method comprising:
   a) providing:
      i) a *Bacillus stearothermophilus* polymerase,
      ii) a sample suspected of containing RNA,
      iii) at least one primer, and
      iv) a reaction buffer comprising magnesium ions, wherein said reaction buffer is substantially free of manganese ions; and
   b) combining said polymerase, said sample suspected of containing RNA, said at least one primer, and said reaction buffer to form a reaction mixture; and
   c) reacting said reaction mixture under conditions such that said polymerase reverse transcribes said RNA to produce cDNA.

2. The method of claim 1, wherein said reacting step is performed at about 50 degrees Celsius to about 80 degrees Celsius.

3. The method of claim 2, wherein said reacting step is performed at about 60 degrees Celsius to about 75 degrees Celsius.

4. The method of claim 1, wherein said primer is selected from oligod(T) and random primers.

5. The method of claim 1, wherein said *Bacillus stearothermophilus* DNA polymerase is encoded by the amino acid sequence selected from the group consisting of SEQ ID NO: 19 and SEQ ID NO: 21.

6. The method of claim 1, further comprising step
   d) amplifying said cDNA.

* * * * *

SEQUENCE LISTING

<160> NUMBER OF SEQ ID NOS: 24

<210> SEQ ID NO 1
<211> LENGTH: 2631
<212> TYPE: DNA
<213> ORGANISM: Thermoactinomyces vulgaris

<400> SEQUENCE: 1

```
ttgaaaaaca agctcgtctt aattgacggc aacagcgtgg cgtaccgcgc cttttttcgcg      60 ttgccgcttt tgcataacga taaagggatt catacgaacg cagtctacgg gtttacgatg     120
atgttaaaca aaattttggc ggaagagcag ccgacccaca ttctcgtggc gtttgacgcc     180
gggaaaacga cgttccgcca tgaaacgttc caagactata aaggcgggcg gcagcagacg     240
ccgccggaac tgtcggaaca gtttccgctg ctgcgcgaat tgctcaaggc gtaccgcatc     300
cccgcctatg agctcgacca ttacgaagcg gacgatatta tcggaacgat ggcggcgcgg     360
gctgagcggg aagggtttgc agtgaaagtc atttccggcg accgcgattt aacccagctt     420
gcttccccgc aagtgacggt ggagattacg aaaaaaggga ttaccgacat cgagtcgtac     480
acgccggaga cggtcgcgga aaaatacggc ctcacccccgg agcaaattgt cgacttgaaa     540
ggattgatgg gcgacaaatc cgacaacatc cccgcgtgc ccggcatcgg ggaaaaaaca     600
gccgtcaagc tgctcaagca attcggcacg gtcgaaaacg tactggcatc gatcgatgag     660
atcaaagggg agaagctgaa agaaaatttg cgccaatacc gggatttggc gcttttaagc     720
aaacagctgg ccgccattcg ccgcgacgcc ccagttgagc tgacgctcga tgacattgtc     780
tacaaaggag aagaccggga aaaagtggtc gccttattta aggagctcgg gttccagtcg     840
tttctcgaca agatggccgt ccaaacggat gaaggcgaga agccgctcgc cgggatggac     900
```

```
tttgcgatcg ccgacggcgt cacggacgaa atgctcgccg acaaggcggc cctcgtcgtg      960
gaggrggtgg gcgacaacta tcaccatgcc ccgattgtcg ggatcgcctt ggccaacgaa     1020
cgcgggcggt ttttcctgcg cccggagacg cgctcgccg atccgaaatt tctcgcttgg     1080
cttggcgatg agacgaagaa aaaaacgatg tttgattcaa agcgggcggc cgtcgcgtta     1140
aaatggaaag gaatcgaact gcgcggcgtc gtgttcgatc tgttgctggc cgcttacttg     1200
ctcgatccgg cgcaggcggc gggcgacgtt gccgcggtgg cgaaaatgca tcagtacgag     1260
gcggtgcggt cggatgaggc ggtctatgga aaaggagcga agcggacggt tcctgatgaa     1320
ccgacgcttg ccgagcatct cgcccgcaag gcggcggcca tttgggcgct tgaagagccg     1380
ttgatggacg aactgcgccg caacgaacaa gatcggctgc tgaccgagct cgaacagccg     1440
ctggctggca ttttggccaa tatggaattt actggagtga agtggacac gaagcggctt      1500
gaacagatgg gggcggagct caccgagcag ctgcaggcgg tcgagcggcg catttacgaa     1560
ctcgccggcc aagagttcaa cattaactcg ccgaaacagc tcgggacggt tttatttgac     1620
aagctgcagc tcccggtgtt gaaaaagaca aaaccggct attcgacttc agccgatgtg      1680
cttgagaagc ttgcaccgca ccatgaaatc gtcgaacata ttttgcatta ccgccaactc     1740
ggcaagctgc agtcaacgta tattgaaggg ctgctgaaag tggtgcaccc cgtgacgggc     1800
aaagtgcaca cgatgttcaa tcaggcgttg acgcaaaccg ggcgcctcag ctccgtcgaa     1860
ccgaatttgc aaaacattcc gattcggctt gaggaagggc ggaaaatccg ccaggcgttc     1920
gtgccgtcgg agccggactg gctcatcttt gcggccgact attcgcaaat cgagctgcgc     1980
gtcctcgccc atatcgcgga agatgacaat ttgattgaag cgttccggcg cgggttggac     2040
atccatacga aaacagccat ggacattttc catgtgagcg aagaagacgt gacagccaac     2100
atgcgccgcc aagcgaaggc cgtcaatttt ggcatcgtgt acggcattag tgattacggt     2160
ctggcgcaaa acttgaacat tacgcgcaaa gaagcggctg aatttattga gcgatatttt     2220
gccagttttc caggtgtaaa gcaatatatg gacaacactg tgcaagaagc gaaacaaaaa     2280
gggtatgtga cgacgctgct gcatcggcgc cgctatttgc ccgatattac aagccgcaac     2340
ttcaacgtcc gcagcttcgc cgagcggacg gcgatgaaca caccgattca agggagcgcc     2400
gctgatatta ttaaaaaagc gatgatcgat ctaagcgtga ggctgcgcga agaacggctg     2460
caggcgcgcc tgttgctgca agtgcatgac gaactcattt tggaggcgcc gaaagaggaa     2520
atcgagcggc tgtgccgcct cgttccagag gtgatggagc aagccgtcgc actccgcgtg     2580
ccgctgaaag tcgattacca ttacggtccg acgtggtacg acgccaaata a             2631
```

<210> SEQ ID NO 2
<211> LENGTH: 876
<212> TYPE: PRT
<213> ORGANISM: Thermoactinomyces vulgaris

<400> SEQUENCE: 2

```
Leu Lys Asn Lys Leu Val Leu Ile Asp Gly Asn Ser Val Ala Tyr Arg
  1               5                  10                  15

Ala Phe Phe Ala Leu Pro Leu Leu His Asn Asp Lys Gly Ile His Thr
                 20                  25                  30

Asn Ala Val Tyr Gly Phe Thr Met Met Leu Asn Lys Ile Leu Ala Glu
         35                  40                  45

Glu Gln Pro Thr His Ile Leu Val Ala Phe Asp Ala Gly Lys Thr Thr
     50                  55                  60
```

-continued

Phe Arg His Glu Thr Phe Gln Asp Tyr Lys Gly Gly Arg Gln Gln Thr
 65                  70                  75                  80

Pro Pro Glu Leu Ser Glu Gln Phe Pro Leu Leu Arg Glu Leu Leu Lys
             85                  90                  95

Ala Tyr Arg Ile Pro Ala Tyr Glu Leu Asp His Tyr Glu Ala Asp Asp
            100                 105                 110

Ile Ile Gly Thr Met Ala Ala Arg Ala Glu Arg Glu Gly Phe Ala Val
            115                 120                 125

Lys Val Ile Ser Gly Asp Arg Asp Leu Thr Gln Leu Ala Ser Pro Gln
            130                 135                 140

Val Thr Val Glu Ile Thr Lys Lys Gly Ile Thr Asp Ile Glu Ser Tyr
145                 150                 155                 160

Thr Pro Glu Thr Val Ala Glu Lys Tyr Gly Leu Thr Pro Glu Gln Ile
            165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
            195                 200                 205

Gly Thr Val Glu Asn Val Leu Ala Ser Ile Asp Glu Ile Lys Gly Glu
            210                 215                 220

Lys Leu Lys Glu Asn Leu Arg Gln Tyr Arg Asp Leu Ala Leu Leu Ser
225                 230                 235                 240

Lys Gln Leu Ala Ala Ile Arg Arg Asp Ala Pro Val Glu Leu Thr Leu
            245                 250                 255

Asp Asp Ile Val Tyr Lys Gly Glu Asp Arg Glu Lys Val Val Ala Leu
            260                 265                 270

Phe Lys Glu Leu Gly Phe Gln Ser Phe Leu Asp Lys Met Ala Val Gln
            275                 280                 285

Thr Asp Glu Gly Glu Lys Pro Leu Ala Gly Met Asp Phe Ala Ile Ala
            290                 295                 300

Asp Gly Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
            325                 330                 335

Leu Ala Asn Glu Arg Gly Arg Phe Phe Leu Arg Pro Glu Thr Ala Leu
            340                 345                 350

Ala Asp Pro Lys Phe Leu Ala Trp Leu Gly Asp Glu Thr Lys Lys Lys
            355                 360                 365

Thr Met Phe Asp Ser Lys Arg Ala Ala Val Ala Leu Lys Trp Lys Gly
            370                 375                 380

Ile Glu Leu Arg Gly Val Val Phe Asp Leu Leu Leu Ala Ala Tyr Leu
385                 390                 395                 400

Leu Asp Pro Ala Gln Ala Ala Gly Asp Val Ala Ala Val Ala Lys Met
            405                 410                 415

His Gln Tyr Glu Ala Val Arg Ser Asp Glu Ala Val Tyr Gly Lys Gly
            420                 425                 430

Ala Lys Arg Thr Val Pro Asp Glu Pro Thr Leu Ala Glu His Leu Ala
            435                 440                 445

Arg Lys Ala Ala Ala Ile Trp Ala Leu Glu Glu Pro Leu Met Asp Glu
            450                 455                 460

Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp

```
                          485                 490                 495
Thr Lys Arg Leu Glu Gln Met Gly Ala Glu Leu Thr Glu Gln Leu Gln
            500                 505                 510

Ala Val Glu Arg Arg Ile Tyr Glu Leu Ala Gly Gln Glu Phe Asn Ile
            515                 520                 525

Asn Ser Pro Lys Gln Leu Gly Thr Val Leu Phe Asp Lys Leu Gln Leu
        530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
                565                 570                 575

Tyr Arg Gln Leu Gly Lys Leu Gln Ser Thr Tyr Ile Glu Gly Leu Leu
            580                 585                 590

Lys Val Val His Pro Val Thr Gly Lys Val His Thr Met Phe Asn Gln
            595                 600                 605

Ala Leu Thr Gln Thr Gly Arg Leu Ser Ser Val Glu Pro Asn Leu Gln
        610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
            660                 665                 670

Glu Ala Phe Arg Arg Gly Leu Asp Ile His Thr Lys Thr Ala Met Asp
            675                 680                 685

Ile Phe His Val Ser Glu Glu Asp Val Thr Ala Asn Met Arg Arg Gln
        690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
            740                 745                 750

Thr Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815

Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
        835                 840                 845

Pro Glu Val Met Glu Gln Ala Val Ala Leu Arg Val Pro Leu Lys Val
        850                 855                 860

Asp Tyr His Tyr Gly Pro Thr Trp Tyr Asp Ala Lys
865                 870                 875

<210> SEQ ID NO 3
<211> LENGTH: 1779
<212> TYPE: DNA
<213> ORGANISM: Thermoactinomyces vulgaris
```

<400> SEQUENCE: 3

```
atggccgtcc aaacggatga aggcgagaag ccgctcgccg ggatggactt tgcgatcgcc      60
gacggcgtca cggacgaaat gctcgccgac aaggcggccc tcgtcgtgga ggtggtgggc     120
gacaactatc accatgcccc gattgtcggg atcgccttgg ccaacgaacg cgggcggttt     180
ttcctgcgcc cggagacggc gctcgccgat ccgaaatttc tcgcttggct tggcgatgag     240
acgaagaaaa aaacgatgtt tgattcaaag cgggcggccg tcgcgttaaa atggaaagga     300
atcgaactgc gcgcgtcgt gttcgatctg ttgctggccg cttacttgct cgatccggcg      360
caggcggcgg gcgacgttgc cgcggtggcg aaaatgcatc agtacgaggc ggtgcggtcg     420
gatgaggcgg tctatggaaa aggagcgaag cggacggttc ctgatgaacc gacgcttgcc     480
gagcatctcg cccgcaaggc ggcggccatt tgggcgcttg aagagccgtt gatggacgaa     540
ctgcgccgca cgaacaaga tcggctgctg accgagctcg aacagccgct ggctggcatt     600
ttggccaata tggaatttac tggagtgaaa gtggacacga agcggcttga acagatgggg     660
gcggagctca ccgagcagct gcaggcggtc gagcggcgca tttacgaact cgccggccaa     720
gagttcaaca ttaactcgcc gaaacagctc gggacggttt tatttgacaa gctgcagctc     780
ccggtgttga aaagacaaa aaccggctat tcgacttcag ccgatgtgct tgagaagctt     840
gcaccgcacc atgaaatcgt cgaacatatt ttgcattacc gccaactcgg caagctgcag     900
tcaacgtata ttgaagggct gctgaaagtg gtgcaccccg tgacgggcaa agtgcacacg     960
atgttcaatc aggcgttgac gcaaaccggg cgcctcagct ccgtcgaacc gaatttgcaa    1020
acattccga ttcggcttga ggaagggcgg aaaatccgcc aggcgttcgt gccgtcggag     1080
ccggactggc tcatctttgc ggccgactat tcgcaaatcg agctgcgcgt cctcgcccat    1140
atcgcggaag atgacaattt gattgaagcg ttccggcgcg ggttggacat ccatacgaaa    1200
acagccatgg acatttttcca tgtgagcgaa gaagacgtga cagccaacat cgccgccaa    1260
gcgaaggccg tcaattttgg catcgtgtac ggcattagtg attacggtct ggcgcaaaac    1320
ttgaacatta cgcgcaaaga gcggctgaa tttattgagc gatattttgc cagttttcca    1380
ggtgtaaagc aatatatgga caacactgtg caagaagcga acaaaaagg gtatgtgacg     1440
acgctgctgc atcggcgccg ctatttgccc gatattacaa ccgcaactt caacgtccgc    1500
agcttcgccg agcggacggc gatgaacaca ccgattcaag ggagcgccgc tgatattatt    1560
aaaaaagcga tgatcgatct aagcgtgagg ctgcgcgaag aacggctgca ggcgcgcctg    1620
ttgctgcaag tgcatgacga actcattttg gaggcgccga agaggaaat cgagcggctg    1680
tgccgcctcg ttccagaggt gatggagcaa gccgtcgcac tccgcgtgcc gctgaaagtc    1740
gattaccatt acggtccgac gtggtacgac gccaaataa                         1779
```

<210> SEQ ID NO 4
<211> LENGTH: 592
<212> TYPE: PRT
<213> ORGANISM: Thermoactinomyces vulgaris

<400> SEQUENCE: 4

```
Met Ala Val Gln Thr Asp Glu Gly Glu Lys Pro Leu Ala Gly Met Asp
  1               5                  10                  15

Phe Ala Ile Ala Asp Gly Val Thr Asp Glu Met Leu Ala Asp Lys Ala
             20                  25                  30

Ala Leu Val Val Glu Val Val Gly Asp Asn Tyr His His Ala Pro Ile
         35                  40                  45
```

-continued

```
Val Gly Ile Ala Leu Ala Asn Glu Arg Gly Arg Phe Leu Arg Pro
 50                  55                  60
Glu Thr Ala Leu Ala Asp Pro Lys Phe Leu Ala Trp Leu Gly Asp Glu
 65                  70                  75                  80
Thr Lys Lys Lys Thr Met Phe Asp Ser Lys Arg Ala Ala Val Ala Leu
                 85                  90                  95
Lys Trp Lys Gly Ile Glu Leu Arg Gly Val Val Phe Asp Leu Leu
                100                 105                 110
Ala Ala Tyr Leu Leu Asp Pro Ala Gln Ala Ala Gly Asp Val Ala Ala
            115                 120                 125
Val Ala Lys Met His Gln Tyr Glu Ala Val Arg Ser Asp Glu Ala Val
130                 135                 140
Tyr Gly Lys Gly Ala Lys Arg Thr Val Pro Asp Glu Pro Thr Leu Ala
145                 150                 155                 160
Glu His Leu Ala Arg Lys Ala Ala Ile Trp Ala Leu Glu Glu Pro
                165                 170                 175
Leu Met Asp Glu Leu Arg Arg Asn Glu Gln Asp Arg Leu Leu Thr Glu
                180                 185                 190
Leu Glu Gln Pro Leu Ala Gly Ile Leu Ala Asn Met Glu Phe Thr Gly
            195                 200                 205
Val Lys Val Asp Thr Lys Arg Leu Glu Gln Met Gly Ala Glu Leu Thr
            210                 215                 220
Glu Gln Leu Gln Ala Val Glu Arg Arg Ile Tyr Glu Leu Ala Gly Gln
225                 230                 235                 240
Glu Phe Asn Ile Asn Ser Pro Lys Gln Leu Gly Thr Val Leu Phe Asp
                245                 250                 255
Lys Leu Gln Leu Pro Val Leu Lys Lys Thr Lys Thr Gly Tyr Ser Thr
                260                 265                 270
Ser Ala Asp Val Leu Glu Lys Leu Ala Pro His His Glu Ile Val Glu
            275                 280                 285
His Ile Leu His Tyr Arg Gln Leu Gly Lys Leu Gln Ser Thr Tyr Ile
            290                 295                 300
Glu Gly Leu Leu Lys Val Val His Pro Val Thr Gly Lys Val His Thr
305                 310                 315                 320
Met Phe Asn Gln Ala Leu Thr Gln Thr Gly Arg Leu Ser Ser Val Glu
                325                 330                 335
Pro Asn Leu Gln Asn Ile Pro Ile Arg Leu Glu Glu Gly Arg Lys Ile
            340                 345                 350
Arg Gln Ala Phe Val Pro Ser Glu Pro Asp Trp Leu Ile Phe Ala Ala
            355                 360                 365
Asp Tyr Ser Gln Ile Glu Leu Arg Val Leu Ala His Ile Ala Glu Asp
            370                 375                 380
Asp Asn Leu Ile Glu Ala Phe Arg Arg Gly Leu Asp Ile His Thr Lys
385                 390                 395                 400
Thr Ala Met Asp Ile Phe His Val Ser Glu Glu Asp Val Thr Ala Asn
                405                 410                 415
Met Arg Arg Gln Ala Lys Ala Val Asn Phe Gly Ile Val Tyr Gly Ile
            420                 425                 430
Ser Asp Tyr Gly Leu Ala Gln Asn Leu Asn Ile Thr Arg Lys Glu Ala
            435                 440                 445
Ala Glu Phe Ile Glu Arg Tyr Phe Ala Ser Phe Pro Gly Val Lys Gln
450                 455                 460
```

-continued

| Tyr | Met | Asp | Asn | Thr | Val | Gln | Glu | Ala | Lys | Gln | Lys | Gly | Tyr | Val | Thr |
| 465 | | | | 470 | | | | | 475 | | | | | 480 | |

| Thr | Leu | Leu | His | Arg | Arg | Arg | Tyr | Leu | Pro | Asp | Ile | Thr | Ser | Arg | Asn |
| | | | | 485 | | | | | 490 | | | | | 495 | |

| Phe | Asn | Val | Arg | Ser | Phe | Ala | Glu | Arg | Thr | Ala | Met | Asn | Thr | Pro | Ile |
| | | | 500 | | | | | 505 | | | | | 510 | | |

| Gln | Gly | Ser | Ala | Ala | Asp | Ile | Ile | Lys | Lys | Ala | Met | Ile | Asp | Leu | Ser |
| | | | 515 | | | | | 520 | | | | | 525 | | |

| Val | Arg | Leu | Arg | Glu | Glu | Arg | Leu | Gln | Ala | Arg | Leu | Leu | Leu | Gln | Val |
| | | 530 | | | | | 535 | | | | | 540 | | | |

| His | Asp | Glu | Leu | Ile | Leu | Glu | Ala | Pro | Lys | Glu | Ile | Glu | Arg | Leu |
| 545 | | | | 550 | | | | | 555 | | | | | 560 |

| Cys | Arg | Leu | Val | Pro | Glu | Val | Met | Glu | Gln | Ala | Val | Ala | Leu | Arg | Val |
| | | | | 565 | | | | | 570 | | | | | 575 | |

| Pro | Leu | Lys | Val | Asp | Tyr | His | Tyr | Gly | Pro | Thr | Trp | Tyr | Asp | Ala | Lys |
| | | | 580 | | | | | 585 | | | | | 590 | | |

<210> SEQ ID NO 5
<211> LENGTH: 1767
<212> TYPE: DNA
<213> ORGANISM: Thermoactinomyces vulgaris

<400> SEQUENCE: 5

```
atggatgaag gcgagaagcc gctcgccggg atggactttg cgatcgccga cggcgtcacg      60
gacgaaatgc tcgccgacaa ggcggccctc gtcgtggagg tggtgggcga caactatcac     120
catgccccga ttgtcgggat cgccttggcc aacgaacgcg gcggttttt cctgcgcccg      180
gagacggcgc tcgccgatcc gaaatttctc gcttggcttg cgatgagac gaagaaaaaa      240
acgatgtttg attcaaagcg ggcggccgtc gcgttaaaat ggaaaggaat cgaactgcgc     300
ggcgtcgtgt cgatctgtt gctggccgct tacttgctcg atccggcgca ggcggcgggc      360
gacgttgccg cggtggcgaa aatgcatcag tacgaggcgg tgcggtcgga tgaggcggtc     420
tatggaaaag gagcgaagcg gacggttcct gatgaaccga cgcttgccga gcatctcgcc     480
cgcaaggcgg cggccatttg ggcgcttgaa gagccgttga tggacgaact cgccgcaac     540
gaacaagatc ggctgctgac cgagctcgaa cagccgctgg ctggcatttt ggccaatatg     600
gaatttactg gagtgaaagt ggacacgaag cggcttgaac agatggggc ggagctcacc     660
gagcagctgc aggcggtcga gcggcgcatt tacgaactcg ccggccaaga gttcaacatt     720
aactcgccga acagctcgg gacggtttta tttgacaagc tgcagctccc ggtgttgaaa      780
aagacaaaaa ccggctattc gacttcagcc gatgtgcttg agaagcttgc accgcaccat     840
gaaatcgtcg aacatatttt gcattaccgc caactcggca agctgcagtc aacgtatatt     900
gaagggctgc tgaaagtggt gcaccccgtg acgggcaaag tgcacacgat gttcaatcag     960
gcgttgacgc aaaccggcg cctcagctcc gtcgaaccga atttgcaaaa cattccgatt    1020
cggcttgagg aagggcggaa aatccgccag gcgttcgtgc cgtcggagcc ggactggctc    1080
atctttgcgg ccgactattc gcaaatcgag ctgcgcgtcc tcgcccatat gcggaagat    1140
gacaattga ttgaagcgtt ccggcgcggg ttggacatcc atacgaaaac agccatggac    1200
atttccatg tgagcgaaga gacgtgaca gccaacatgc cgcgcaagc gaaggccgtc      1260
aatttttggca tcgtgtacgg cattagtgat tacggtctgg cgcaaaactt gaacattacg    1320
cgcaaagaag cggctgaatt tattgagcga tattttgcca gttttccagg tgtaaagcaa    1380
tatatggaca acactgtgca agaagcgaaa caaaaagggt atgtgacgac gctgctgcat    1440
```

-continued

```
cggcgccgct atttgcccga tattacaagc cgcaacttca acgtccgcag cttcgccgag    1500
cggacggcga tgaacacacc gattcaaggg agcgccgctg atattattaa aaaagcgatg    1560
atcgatctaa gcgtgaggct gcgcgaagaa cggctgcagg cgcgcctgtt gctgcaagtg    1620
catgacgaac tcattttgga ggcgccgaaa gaggaaatcg agcggctgtg ccgcctcgtt    1680
ccagaggtga tggagcaagc cgtcgcactc cgcgtgccgc tgaaagtcga ttaccattac    1740
ggtccgacgt ggtacgacgc caaataa                                        1767
```

<210> SEQ ID NO 6
<211> LENGTH: 588
<212> TYPE: PRT
<213> ORGANISM: Thermoactinomyces vulgaris

<400> SEQUENCE: 6

```
Thr Asp Glu Gly Glu Lys Pro Leu Ala Gly Met Asp Phe Ala Ile Ala
  1               5                  10                  15

Asp Gly Val Thr Asp Glu Met Leu Ala Asp Lys Ala Ala Leu Val Val
             20                  25                  30

Glu Val Val Gly Asp Asn Tyr His His Ala Pro Ile Val Gly Ile Ala
         35                  40                  45

Leu Ala Asn Glu Arg Gly Arg Phe Phe Leu Arg Pro Glu Thr Ala Leu
     50                  55                  60

Ala Asp Pro Lys Phe Leu Ala Trp Leu Gly Asp Glu Thr Lys Lys Lys
 65                  70                  75                  80

Thr Met Phe Asp Ser Lys Arg Ala Ala Val Ala Leu Lys Trp Lys Gly
                 85                  90                  95

Ile Glu Leu Arg Gly Val Val Phe Asp Leu Leu Leu Ala Ala Tyr Leu
            100                 105                 110

Leu Asp Pro Ala Gln Ala Ala Gly Asp Val Ala Ala Val Ala Lys Met
        115                 120                 125

His Gln Tyr Glu Ala Val Arg Ser Asp Glu Ala Val Tyr Gly Lys Gly
    130                 135                 140

Ala Lys Arg Thr Val Pro Asp Glu Pro Thr Leu Ala Glu His Leu Ala
145                 150                 155                 160

Arg Lys Ala Ala Ala Ile Trp Ala Leu Glu Glu Pro Leu Met Asp Glu
                165                 170                 175

Leu Arg Arg Asn Glu Gln Asp Arg Leu Leu Thr Glu Leu Glu Gln Pro
            180                 185                 190

Leu Ala Gly Ile Leu Ala Asn Met Glu Phe Thr Gly Val Lys Val Asp
        195                 200                 205

Thr Lys Arg Leu Glu Gln Met Gly Ala Glu Leu Thr Glu Gln Leu Gln
    210                 215                 220

Ala Val Glu Arg Arg Ile Tyr Glu Leu Ala Gly Gln Glu Phe Asn Ile
225                 230                 235                 240

Asn Ser Pro Lys Gln Leu Gly Thr Val Leu Phe Asp Lys Leu Gln Leu
                245                 250                 255

Pro Val Leu Lys Lys Thr Lys Thr Gly Tyr Ser Thr Ser Ala Asp Val
            260                 265                 270

Leu Glu Lys Leu Ala Pro His His Glu Ile Val Glu His Ile Leu His
        275                 280                 285

Tyr Arg Gln Leu Gly Lys Leu Gln Ser Thr Tyr Ile Glu Gly Leu Leu
    290                 295                 300

Lys Val Val His Pro Val Thr Gly Lys Val His Thr Met Phe Asn Gln
```

```
                305                 310                 315                 320
Ala Leu Thr Gln Thr Gly Arg Leu Ser Ser Val Glu Pro Asn Leu Gln
                325                 330                 335

Asn Ile Pro Ile Arg Leu Glu Glu Gly Arg Lys Ile Arg Gln Ala Phe
                340                 345                 350

Val Pro Ser Glu Pro Asp Trp Leu Ile Phe Ala Ala Asp Tyr Ser Gln
                355                 360                 365

Ile Glu Leu Arg Val Leu Ala His Ile Ala Glu Asp Asn Leu Ile
        370                 375                 380

Glu Ala Phe Arg Arg Gly Leu Asp Ile His Thr Lys Thr Ala Met Asp
385                 390                 395                 400

Ile Phe His Val Ser Glu Glu Asp Val Thr Ala Asn Met Arg Arg Gln
                405                 410                 415

Ala Lys Ala Val Asn Phe Gly Ile Val Tyr Gly Ile Ser Asp Tyr Gly
                420                 425                 430

Leu Ala Gln Asn Leu Asn Ile Thr Arg Lys Glu Ala Ala Glu Phe Ile
                435                 440                 445

Glu Arg Tyr Phe Ala Ser Phe Pro Gly Val Lys Gln Tyr Met Asp Asn
        450                 455                 460

Thr Val Gln Glu Ala Lys Gln Lys Gly Tyr Val Thr Thr Leu Leu His
465                 470                 475                 480

Arg Arg Arg Tyr Leu Pro Asp Ile Thr Ser Arg Asn Phe Asn Val Arg
                485                 490                 495

Ser Phe Ala Glu Arg Thr Ala Met Asn Thr Pro Ile Gln Gly Ser Ala
                500                 505                 510

Ala Asp Ile Ile Lys Lys Ala Met Ile Asp Leu Ser Val Arg Leu Arg
                515                 520                 525

Glu Glu Arg Leu Gln Ala Arg Leu Leu Leu Gln Val His Asp Glu Leu
        530                 535                 540

Ile Leu Glu Ala Pro Lys Glu Glu Ile Glu Arg Leu Cys Arg Leu Val
545                 550                 555                 560

Pro Glu Val Met Glu Gln Ala Val Ala Leu Arg Val Pro Leu Lys Val
                565                 570                 575

Asp Tyr His Tyr Gly Pro Thr Trp Tyr Asp Ala Lys
                580                 585

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:  Synthetic

<400> SEQUENCE: 7
gacgtcgcat gctcct                                                       16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 8
accgaattcc tcgagtc                                                      17

<210> SEQ ID NO 9
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (24)
<223> OTHER INFORMATION: i

<400> SEQUENCE: 9
tagagcggcc gcgayccnaa yytncaraay at                                    32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (14)..(15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (20)
<223> OTHER INFORMATION: i
<220> FEATURE:
<221> NAME/KEY: modified_base
<222> LOCATION: (30)
<223> OTHER INFORMATION: i

<400> SEQUENCE: 10
ctgcggccgc ctannacnan ytcrtcrtgn ac                                    32

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 11
gcgcgaagaa cggctgcagg c                                                21

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (8)..(9)
<223> OTHER INFORMATION: i
<220> FEATURE:
<221> NAME/KEY: modified_base
<222> LOCATION: (15)..(19)
<223> OTHER INFORMATION: i
<220> FEATURE:
<221> NAME/KEY: modified_base
<222> LOCATION: (21)
<223> OTHER INFORMATION: i

<400> SEQUENCE: 12
```
ttcaaccnna actcnnnnna ncagct                                26

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
cggctccgac ggcacgaacg                                       20

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 14
tcaacaccgg gagctgcagc ttgtca                                26

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic

<400> SEQUENCE: 15
catggatgaa ggtgagaagc cactggccgg gatggacttt gcgat           45

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 16
cgcaaagtcc atcccggcca gtggcttctc accttcatc                  39

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence: Synthetic

<400> SEQUENCE: 17
aaaccatggc agttcaaacc gatgaaggcg agaaaccact ggctgggatg gactttgcga    60
t                                                                    61

<210> SEQ ID NO 18
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 18
cgcaaagtcc atcccagcca gtggtttctc gccttcatcg gtttgaactg ccatggttt     59

<210> SEQ ID NO 19

<211> LENGTH: 2631
<212> TYPE: DNA
<213> ORGANISM: Bacillus stearothermophilus

<400> SEQUENCE: 19

| | | | | | |
|---|---|---|---|---|---|
| atgaagaaga | agctagtact | aattgatggc | aacagtgtgg | cataccgcgc | cttttttgcc | 60 |
| ttgccactt | tgcataacga | caaaggcatt | catacgaatg | cggtttacgg | gtttacgatg | 120 |
| atgttgaaca | aaattttggc | ggaagaacaa | ccgacccatt | tacttgtagc | gtttgacgcc | 180 |
| ggaaaaacga | cgttccggca | tgaaacgttt | caagagtata | aaggcggacg | gcaacaaact | 240 |
| cccccggaac | tgtccgagca | gtttccgctg | ttgcgcgagc | tattaaaagc | gtaccgcatt | 300 |
| cccgcttatg | aacttgatca | ttacgaagcg | gacgatatta | tcgggacgct | cgctgcccgc | 360 |
| gctgagcaag | aagggtttga | agtgaaaatc | atttccggcg | accgcgattt | aacccagctc | 420 |
| gcctcccgtc | atgtgacggt | cgatattacg | aaaaaaggga | ttaccgacat | tgagccgtat | 480 |
| acgccagaga | ccgttcgcga | aaatacggc | ctgactccgg | agcaaatagt | ggatttaaaa | 540 |
| ggattgatgg | gcgataaatc | cgacaacatc | ccgggcgtgc | ccggcatcgg | gaaaaaacg | 600 |
| gcggtcaagc | tgctgaagca | atttggtacg | gtggaaaatg | tgctcgcatc | gattgatgag | 660 |
| gtgaaagggg | aaaaactgaa | agaaaacttg | cgccaacacc | gggatttagc | tctcttgagc | 720 |
| aaacagctgg | cgtccatttg | ccgcgacgcc | ccggttgagc | tgtcgttaga | tgacattgtc | 780 |
| tacgaaggac | aagaccgcga | aaaagtcatc | gcgttattta | agaactcgg | gtttcagtcg | 840 |
| ttcttggaaa | aaatggccgc | gccggcagcc | gaaggggaga | accgcttga | ggagatggag | 900 |
| tttgccatcg | ttgacgtcat | taccgaagag | atgcttgccg | acaaggcagc | gcttgtcgtt | 960 |
| gaggtgatgg | aagaaaacta | ccacgatgcc | ccgattgtcg | aatcgcact | agtgaacgag | 1020 |
| catgggcgat | tttttatgcg | cccggagacc | gcgctggctg | attcgcaatt | tttagcatgg | 1080 |
| cttgccgatg | aaacgaagaa | aaaaagcatg | tttgacgcca | agcgggcagt | cgttgcctta | 1140 |
| aagtggaaag | gaattgagct | tcgcggcgtc | gcctttgatt | tattgctcgc | tgcctatttg | 1200 |
| ctcaatccgg | ctcaagatgc | cggcgatatc | gctgcggtgg | cgaaaatgaa | acaatatgaa | 1260 |
| gcggtgcggt | cggatgaagc | ggtctatggc | aaaggcgtca | agcggtcgct | gccggacgaa | 1320 |
| cagacgcttg | ctgagcatct | cgttcgcaaa | gcggcagcca | tttgggcgct | tgagcagccg | 1380 |
| tttatggacg | atttgcggaa | caacgaacaa | gatcaattat | taacgaagct | tgagcagccg | 1440 |
| ctggcggcga | ttttggctga | aatggaattc | actggggtga | acgtggatac | aaagcggctt | 1500 |
| gaacagatgg | gttcggagct | cgccgaacaa | ctgcgtgcca | tcgagcagcg | catttacgag | 1560 |
| ctagccggcc | aagagttcaa | cattaactca | ccaaaacagc | tcggagtcat | tttatttgaa | 1620 |
| aagctgcagc | taccggtgct | gaagaagacg | aaaacaggct | attcgacttc | ggctgatgtg | 1680 |
| cttgagaagc | ttgcgccgca | tcatgaaatc | gtcgaaaaca | ttttgcatta | ccgccagctt | 1740 |
| ggcaaactgc | aatcaacgta | tattgaagga | ttgttgaaag | ttgtgcgccc | tgataccggc | 1800 |
| aaagtgcata | cgatgttcaa | ccaagcgctg | acgcaaactg | ggcggctcag | ctcggccgag | 1860 |
| ccgaacttgc | aaaacattcc | gattcggctc | gaagagggc | ggaaaatccg | ccaagcgttc | 1920 |
| gtcccgtcag | agccggactg | gctcattttc | gccgccgatt | actcacaaat | tgaattgcgc | 1980 |
| gtcctcgccc | atatcgccga | tgacgacaat | ctaattgaag | cgttccaacg | cgatttggat | 2040 |
| attcacacaa | aaacggcgat | ggacattttc | catgtgagcg | aagaggaagt | cacggccaac | 2100 |
| atgcgccgcc | aggcaaaggc | cgttaacttc | ggtatcgttt | acggaattag | cgattacgga | 2160 |
| ttggcgcaaa | acttgaacat | tacgcgcaaa | gaagctgccg | aatttatcga | acgttacttc | 2220 |

-continued

```
gccagctttc cgggcgtaaa gcagtatatg gaaaacattg tgcaagaagc gaaacagaaa    2280
ggatatgtga caacgctgtt gcatcggcgc cgctatttgc ctgatattac aagccgcaat    2340
ttcaacgtcc gcagttttgc agagcggacg gccatgaaca cgccaattca aggaagcgcc    2400
gctgacatta ttaaaaaagc gatgattgat ttagcggcac ggctgaaaga gagcagctt    2460 caggctcgtc ttttgctgca agtgcatgac gagctcattt tggaagcgcc aaaagaggaa    2520
attgagcgat tatgtgagct tgttccggaa gtgatggagc aggccgttac gctccgcgtg    2580
ccgctgaaag tcgactacca ttacggccca acatggtatg atgccaaata a             2631
```

<210> SEQ ID NO 20
<211> LENGTH: 876
<212> TYPE: PRT
<213> ORGANISM: Bacillus stearothermophilus

<400> SEQUENCE: 20

```
Met Lys Lys Leu Val Leu Ile Asp Gly Asn Ser Val Ala Tyr Arg
 1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45

Glu Gln Pro Thr His Leu Leu Val Ala Phe Asp Ala Gly Lys Thr Thr
        50                  55                  60

Phe Arg His Glu Thr Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Lys
                85                  90                  95

Ala Tyr Arg Ile Pro Ala Tyr Glu Leu Asp His Tyr Glu Ala Asp Asp
            100                 105                 110

Ile Ile Gly Thr Leu Ala Ala Arg Ala Glu Gln Glu Gly Phe Glu Val
        115                 120                 125

Lys Ile Ile Ser Gly Asp Arg Asp Leu Thr Gln Leu Ala Ser Arg His
    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
        195                 200                 205

Gly Thr Val Glu Asn Val Leu Ala Ser Ile Asp Glu Val Lys Gly Glu
    210                 215                 220

Lys Leu Lys Glu Asn Leu Arg Gln His Arg Asp Leu Ala Leu Leu Ser
225                 230                 235                 240

Lys Gln Leu Ala Ser Ile Cys Arg Asp Ala Pro Val Glu Leu Ser Leu
                245                 250                 255

Asp Asp Ile Val Tyr Glu Gly Gln Asp Arg Glu Lys Val Ile Ala Leu
            260                 265                 270

Phe Lys Glu Leu Gly Phe Gln Ser Phe Leu Glu Lys Met Ala Ala Pro
        275                 280                 285

Ala Ala Glu Gly Glu Lys Pro Leu Glu Glu Met Glu Phe Ala Ile Val
    290                 295                 300
```

-continued

```
Asp Val Ile Thr Glu Glu Met Leu Ala Asp Lys Ala Ala Leu Val Val
305                 310                 315                 320

Glu Val Met Glu Glu Asn Tyr His Asp Ala Pro Ile Val Gly Ile Ala
                325                 330                 335

Leu Val Asn Glu His Gly Arg Phe Phe Met Arg Pro Glu Thr Ala Leu
            340                 345                 350

Ala Asp Ser Gln Phe Leu Ala Trp Leu Ala Asp Glu Thr Lys Lys Lys
        355                 360                 365

Ser Met Phe Asp Ala Lys Arg Ala Val Val Ala Leu Lys Trp Lys Gly
    370                 375                 380

Ile Glu Leu Arg Gly Val Ala Phe Asp Leu Leu Ala Ala Tyr Leu
385                 390                 395                 400

Leu Asn Pro Ala Gln Asp Ala Gly Asp Ile Ala Ala Val Ala Lys Met
                405                 410                 415

Lys Gln Tyr Glu Ala Val Arg Ser Asp Glu Ala Val Tyr Gly Lys Gly
            420                 425                 430

Val Lys Arg Ser Leu Pro Asp Glu Gln Thr Leu Ala Glu His Leu Val
        435                 440                 445

Arg Lys Ala Ala Ala Ile Trp Ala Leu Glu Gln Pro Phe Met Asp Asp
    450                 455                 460

Leu Arg Asn Asn Glu Gln Asp Gln Leu Leu Thr Lys Leu Glu Gln Pro
465                 470                 475                 480

Leu Ala Ala Ile Leu Ala Glu Met Glu Phe Thr Gly Val Asn Val Asp
                485                 490                 495

Thr Lys Arg Leu Glu Gln Met Gly Ser Glu Leu Ala Glu Gln Leu Arg
            500                 505                 510

Ala Ile Glu Gln Arg Ile Tyr Glu Leu Ala Gly Gln Glu Phe Asn Ile
        515                 520                 525

Asn Ser Pro Lys Gln Leu Gly Val Ile Leu Phe Glu Lys Leu Gln Leu
    530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu Asn Ile Leu His
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Gly Lys Val His Thr Met Phe Asn Gln
        595                 600                 605

Ala Leu Thr Gln Thr Gly Arg Leu Ser Ser Ala Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Asp Asp Asp Asn Leu Ile
            660                 665                 670

Glu Ala Phe Gln Arg Asp Leu Asp Ile His Thr Lys Thr Ala Met Asp
        675                 680                 685

Ile Phe His Val Ser Glu Glu Val Thr Ala Asn Met Arg Arg Gln
    690                 695                 700

Ala Lys Ala Val Asn Phe Gly Ile Val Tyr Gly Ile Ser Asp Tyr Gly
705                 710                 715                 720
```

-continued

```
Leu Ala Gln Asn Leu Asn Ile Thr Arg Lys Glu Ala Ala Glu Phe Ile
                725                 730                 735
Glu Arg Tyr Phe Ala Ser Phe Pro Gly Val Lys Gln Tyr Met Glu Asn
            740                 745                 750
Ile Val Gln Glu Ala Lys Gln Lys Gly Tyr Val Thr Thr Leu Leu His
        755                 760                 765
Arg Arg Arg Tyr Leu Pro Asp Ile Thr Ser Arg Asn Phe Asn Val Arg
    770                 775                 780
Ser Phe Ala Glu Arg Thr Ala Met Asn Thr Pro Ile Gln Gly Ser Ala
785                 790                 795                 800
Ala Asp Ile Ile Lys Lys Ala Met Ile Asp Leu Ala Ala Arg Leu Lys
                805                 810                 815
Glu Glu Gln Leu Gln Ala Arg Leu Leu Leu Gln Val His Asp Glu Leu
            820                 825                 830
Ile Leu Glu Ala Pro Lys Glu Glu Ile Glu Arg Leu Cys Glu Leu Val
        835                 840                 845
Pro Glu Val Met Glu Gln Ala Val Thr Leu Arg Val Pro Leu Lys Val
    850                 855                 860
Asp Tyr His Tyr Gly Pro Thr Trp Tyr Asp Ala Lys
865                 870                 875

<210> SEQ ID NO 21
<211> LENGTH: 1764
<212> TYPE: DNA
<213> ORGANISM: Bacillus stearothermophilus

<400> SEQUENCE: 21
gccgaagggg agaaaccgct tgaggagatg gagtttgcca tcgttgacgt cattaccgaa      60
gagatgcttg ccgacaaggc agcgcttgtc gttgaggtga tggaagaaaa ctaccacgat     120
gccccgattg tcggaatcgc actagtgaac gagcatgggc gatttttat gcgcccggag      180 accgcgctgg ctgattcgca atttttagca tggcttgccg atgaaacgaa gaaaaaaagc    240
atgtttgacg ccaagcgggc agtcgttgcc ttaaagtgga aaggaattga gcttcgcggc    300
gtcgcctttg atttattgct cgctgcctat ttgctcaatc cggctcaaga tgccggcgat    360
atcgctgcgg tggcgaaaat gaaacaatat gaagcggtgc ggtcggatga agcggtctat    420
ggcaaaggcg tcaagcggtc gctgccggac gaacagacgc ttgctgagca tctcgttcgc    480
aaagcggcag ccatttgggc gcttgagcag ccgtttatgg acgatttgcg gaacaacgaa    540
caagatcaat tattaacgaa gcttgagcac gcgctggcgg cgattttggc tgaaatggaa    600
ttcactgggg tgaacgtgga tacaaagcgg cttgaacaga tgggttcgga gctcgccgaa    660
caactgcgtg ccatcgagca gcgcatttac gagctagccg ccaagagtt caacattaac    720 tcaccaaaac agctcggagt cattttattt gaaaagctgc agctaccggt gctgaagaag    780
acgaaaacag gctattcgac ttcggctgat gtgcttgaga gcttgcgcc gcatcatgaa    840 atcgtcgaaa acattttgca ttaccgccag cttggcaaac tgcaatcaac gtatattgaa    900
ggattgttga agttgtgcg ccctgatacc ggcaaagtgc atacgatgtt caaccaagcg    960
ctgacgcaaa ctgggcggct cagctcggcc gagccgaact tgcaaaacat tccgattcgg   1020
ctcgaagagg ggcggaaaat ccgccaagcg ttcgtcccgt cagagccgga ctggctcatt   1080
ttcgccgccg attactcaca aattgaattg cgcgtcctcg cccatatcgc cgatgacgac   1140
aatctaattg aagcgttcca acgcgatttg gatattcaca caaaaacggc gatggacatt   1200
ttccagttga gcgaagagga agtcacggcc aacatgcgcc gccaggcaaa ggccgttaac   1260
```

```
ttcggtatcg tttacggaat tagcgattac ggattggcgc aaaacttgaa cattacgcgc    1320
aaagaagctg ccgaatttat cgaacgttac ttcgccagct ttccgggcgt aaagcagtat    1380
atggaaaaca tagtgcaaga agcgaaacag aaaggatatg tgacaacgct gttgcatcgg    1440
cgccgctatt tgcctgatat tacaagccgc aatttcaacg tccgcagttt tgcagagcgg    1500
acggccatga acacgccaat tcaaggaagc gccgctgaca ttattaaaaa agcgatgatt    1560
gatttagcgg cacggctgaa agaagagcag cttcaggctc gtcttttgct gcaagtgcat    1620
gacgagctca ttttggaagc gccaaaagag gaaattgagc gattatgtga gcttgttccg    1680
gaagtgatgg agcaggccgt tacgctccgc gtgccgctga agtcgacta ccattacggc    1740 ccaacatggt atgatgccaa ataa                                           1764
```

<210> SEQ ID NO 22
<211> LENGTH: 587
<212> TYPE: PRT
<213> ORGANISM: Bacillus stearothermophilus

<400> SEQUENCE: 22

```
Ala Glu Gly Glu Lys Pro Leu Glu Glu Met Glu Phe Ala Ile Val Asp
  1               5                  10                  15

Val Ile Thr Glu Glu Met Leu Ala Asp Lys Ala Ala Leu Val Val Glu
                 20                  25                  30

Val Met Glu Glu Asn Tyr His Asp Ala Pro Ile Val Gly Ile Ala Leu
             35                  40                  45

Val Asn Glu His Gly Arg Phe Phe Met Arg Pro Glu Thr Ala Leu Ala
         50                  55                  60

Asp Ser Gln Phe Leu Ala Trp Leu Ala Asp Glu Thr Lys Lys Lys Ser
 65                  70                  75                  80

Met Phe Asp Ala Lys Arg Ala Val Val Ala Leu Lys Trp Lys Gly Ile
                 85                  90                  95

Glu Leu Arg Gly Val Ala Phe Asp Leu Leu Leu Ala Ala Tyr Leu Leu
            100                 105                 110

Asn Pro Ala Gln Asp Ala Gly Asp Ile Ala Ala Val Ala Lys Met Lys
        115                 120                 125

Gln Tyr Glu Ala Val Arg Ser Asp Glu Ala Val Tyr Gly Lys Gly Val
    130                 135                 140

Lys Arg Ser Leu Pro Asp Glu Gln Thr Leu Ala Glu His Leu Val Arg
145                 150                 155                 160

Lys Ala Ala Ala Ile Trp Ala Leu Glu Gln Pro Phe Met Asp Asp Leu
                165                 170                 175

Arg Asn Asn Glu Gln Asp Gln Leu Leu Thr Lys Leu Glu His Ala Leu
            180                 185                 190

Ala Ala Ile Leu Ala Glu Met Glu Phe Thr Gly Val Asn Val Asp Thr
        195                 200                 205

Lys Arg Leu Glu Gln Met Gly Ser Glu Leu Ala Glu Gln Leu Arg Ala
    210                 215                 220

Ile Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                245                 250                 255

Val Leu Lys Lys Thr Lys Thr Gly Tyr Ser Thr Ser Ala Asp Val Leu
            260                 265                 270

Glu Lys Leu Ala Pro His His Glu Ile Val Glu Asn Ile Leu His Tyr
```

-continued

```
                275                 280                 285
Arg Gln Leu Gly Lys Leu Gln Ser Thr Tyr Ile Glu Gly Leu Leu Lys
            290                 295                 300
Val Val Arg Pro Asp Thr Gly Lys Val His Thr Met Phe Asn Gln Ala
305                 310                 315                 320
Leu Thr Gln Thr Gly Arg Leu Ser Ser Ala Glu Pro Asn Leu Gln Asn
                325                 330                 335
Ile Pro Ile Arg Leu Glu Glu Gly Arg Lys Ile Arg Gln Ala Phe Val
            340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Asp Asp Asn Leu Ile Glu
    370                 375                 380
Ala Phe Gln Arg Asp Leu Asp Ile His Thr Lys Thr Ala Met Asp Ile
385                 390                 395                 400
Phe Gln Leu Ser Glu Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
            420                 425                 430
Ala Gln Asn Leu Asn Ile Thr Arg Lys Glu Ala Ala Glu Phe Ile Glu
        435                 440                 445
Arg Tyr Phe Ala Ser Phe Pro Gly Val Lys Gln Tyr Met Glu Asn Ile
    450                 455                 460
Val Gln Glu Ala Lys Gln Lys Gly Tyr Val Thr Thr Leu Leu His Arg
465                 470                 475                 480
Arg Arg Tyr Leu Pro Asp Ile Thr Ser Arg Asn Phe Asn Val Arg Ser
                485                 490                 495
Phe Ala Glu Arg Thr Ala Met Asn Thr Pro Ile Gln Gly Ser Ala Ala
            500                 505                 510
Asp Ile Ile Lys Lys Ala Met Ile Asp Leu Ala Ala Arg Leu Lys Glu
        515                 520                 525
Glu Gln Leu Gln Ala Arg Leu Leu Leu Gln Val His Asp Glu Leu Ile
    530                 535                 540
Leu Glu Ala Pro Lys Glu Glu Ile Glu Arg Leu Cys Glu Leu Val Pro
545                 550                 555                 560
Glu Val Met Glu Gln Ala Val Thr Leu Arg Val Pro Leu Lys Val Asp
                565                 570                 575
Tyr His Tyr Gly Pro Thr Trp Tyr Asp Ala Lys
            580                 585

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 23
gccattctca ccggattcag tccgt                                         25

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 24
agccgccgtc ccgtcaagtc ag                                            22
```